(12) United States Patent
Ammann

(10) Patent No.: US 11,786,358 B2
(45) Date of Patent: Oct. 17, 2023

(54) APPARATUS AND METHOD FOR ANATOMIC ACL RECONSTRUCTION

(71) Applicant: AnatomACL, LLC, Boulder, CO (US)

(72) Inventor: Kelly G. Ammann, Boulder, CO (US)

(73) Assignee: AnatomACL, LLC, Boulder, CO (US)

(*) Notice: Subject to any disclaimer, the term of this patent is extended or adjusted under 35 U.S.C. 154(b) by 0 days.

(21) Appl. No.: 15/926,454

(22) Filed: Mar. 20, 2018

(65) Prior Publication Data

US 2019/0029803 A1 Jan. 31, 2019

Related U.S. Application Data

(63) Continuation of application No. 14/754,445, filed on Jun. 29, 2015, now Pat. No. 9,918,828, which is a continuation-in-part of application No. 14/397,370, filed as application No. PCT/US2013/024145 on Jan. 31, 2013, now Pat. No. 10,939,992, said application No. 14/754,445 is a continuation-in-part of application No. 13/528,680, filed on Jun. 20, 2012, now Pat. No. 9,089,416, said application No. 14/397,370 is a continuation-in-part of application
(Continued)

(51) Int. Cl.
| | | |
|---|---|---|
| *A61F 2/08* | (2006.01) | |
| *A61B 17/16* | (2006.01) | |
| *A61B 17/04* | (2006.01) | |
| *A61B 17/17* | (2006.01) | |

(52) U.S. Cl.
CPC ........ *A61F 2/0811* (2013.01); *A61B 17/1604* (2013.01); *A61F 2/08* (2013.01); *A61F 2/0805* (2013.01); *A61B 17/0485* (2013.01); *A61B 17/1637* (2013.01); *A61B 17/17* (2013.01); *A61B 17/1714* (2013.01); *A61F 2002/0829* (2013.01); *A61F 2002/0841* (2013.01); *A61F 2002/0858* (2013.01); *A61F 2002/0882* (2013.01); *A61F 2220/0033* (2013.01)

(58) Field of Classification Search
CPC combination set(s) only.
See application file for complete search history.

(56) References Cited

U.S. PATENT DOCUMENTS

| | | |
|---|---|---|
| 5,282,802 A | 2/1994 | Mahoney, III |
| 6,123,711 A | 9/2000 | Winters |
| 6,214,007 B1 | 4/2001 | Anderson |

(Continued)

FOREIGN PATENT DOCUMENTS

| | | |
|---|---|---|
| EP | 1297794 | 4/2003 |
| WO | WO 2007/109280 | 9/2007 |

(Continued)

*Primary Examiner* — Yashita Sharma
(74) *Attorney, Agent, or Firm* — Pandiscio & Pandiscio

(57) ABSTRACT

A graft fixation device comprising: a graft separator comprising a distal end, a proximal end, a cavity disposed between the distal end and the proximal end, and at least one guide rib disposed radially outboard of the cavity and extending between the distal end and the proximal end; and an interference screw rotatably mountable within the cavity, the interference screw comprising a distal end, a proximal end, and a screw thread disposed intermediate thereof, the screw thread disposed radially outboard of at least a portion of the graft separator and radially inboard of the at least one rib.

11 Claims, 51 Drawing Sheets

Related U.S. Application Data

No. 13/528,680, filed on Jun. 20, 2012, now Pat. No. 9,089,416.

(60) Provisional application No. 62/175,733, filed on Jun. 15, 2015, provisional application No. 62/137,888, filed on Mar. 25, 2015, provisional application No. 62/129,860, filed on Mar. 8, 2015, provisional application No. 62/018,327, filed on Jun. 27, 2014, provisional application No. 61/638,848, filed on Apr. 26, 2012, provisional application No. 61/498,663, filed on Jun. 20, 2011.

(56) References Cited

U.S. PATENT DOCUMENTS

| | | | |
|---|---|---|---|
| 6,833,005 | B1 | 12/2004 | Mantas et al. |
| 7,235,078 | B2 | 6/2007 | West, Jr. |
| 10,022,215 | B2 | 7/2018 | Ammann |
| 2002/0156476 | A1 | 10/2002 | Wilford |
| 2003/0040795 | A1 | 2/2003 | Elson et al. |
| 2004/0153076 | A1* | 8/2004 | Singhatat ............ A61B 17/1675 623/13.14 |
| 2006/0052787 | A1 | 3/2006 | Re et al. |
| 2006/0095130 | A1 | 5/2006 | Caborn et al. |
| 2006/0189991 | A1 | 8/2006 | Bickley |
| 2006/0276789 | A1 | 12/2006 | Jackson |
| 2007/0233071 | A1 | 10/2007 | Dewey et al. |
| 2009/0287259 | A1 | 11/2009 | Trenhaile et al. |
| 2009/0319043 | A1 | 12/2009 | McDevitt et al. |
| 2010/0069958 | A1 | 3/2010 | Sullivan et al. |
| 2011/0282449 | A1 | 11/2011 | Montgomery et al. |
| 2013/0079780 | A1 | 3/2013 | Wagner et al. |

FOREIGN PATENT DOCUMENTS

| | | |
|---|---|---|
| WO | WO 2007/110863 | 10/2007 |
| WO | WO 2010/045207 | 4/2010 |
| WO | WO 2013/162663 | 10/2013 |

\* cited by examiner

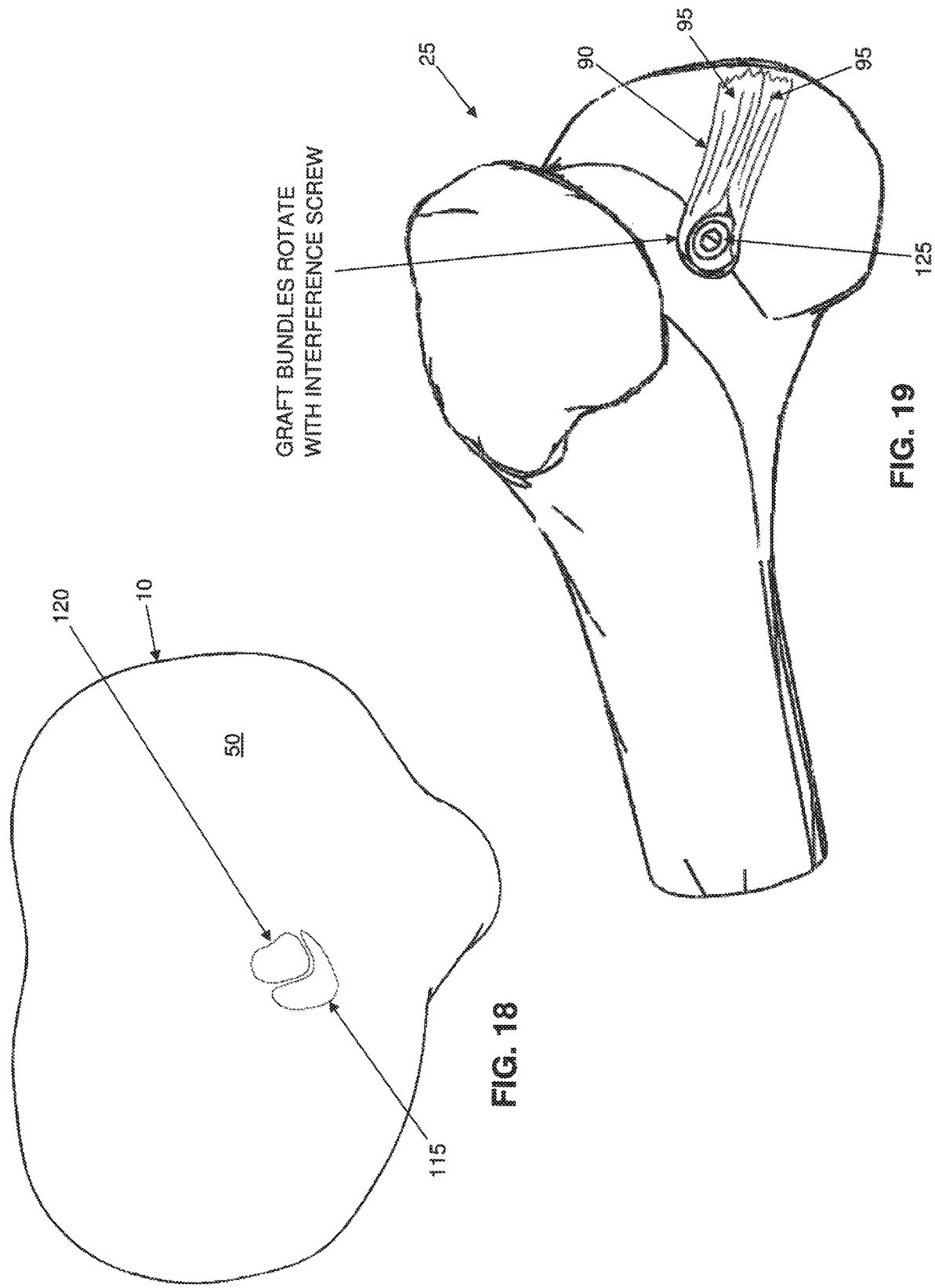

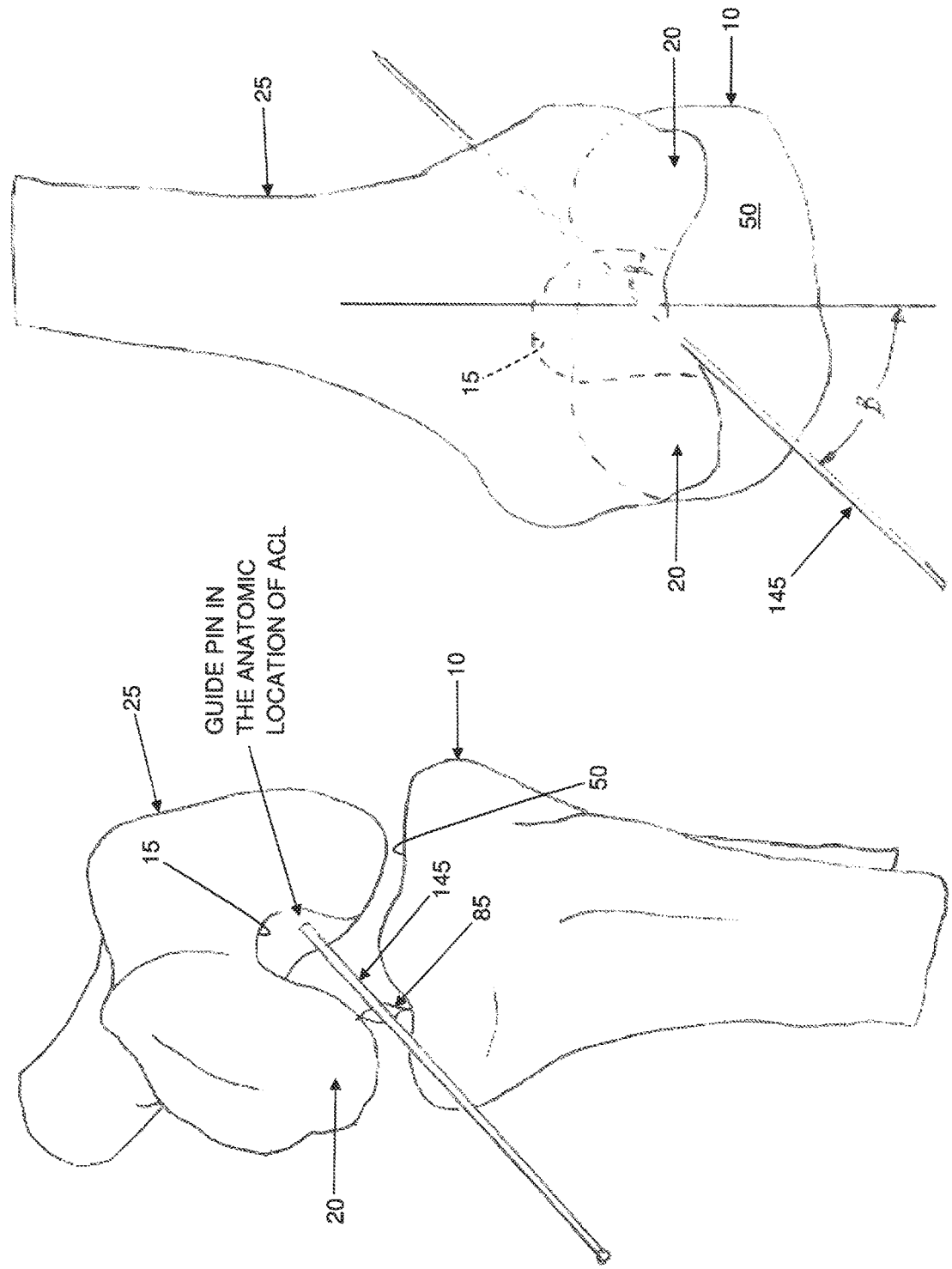

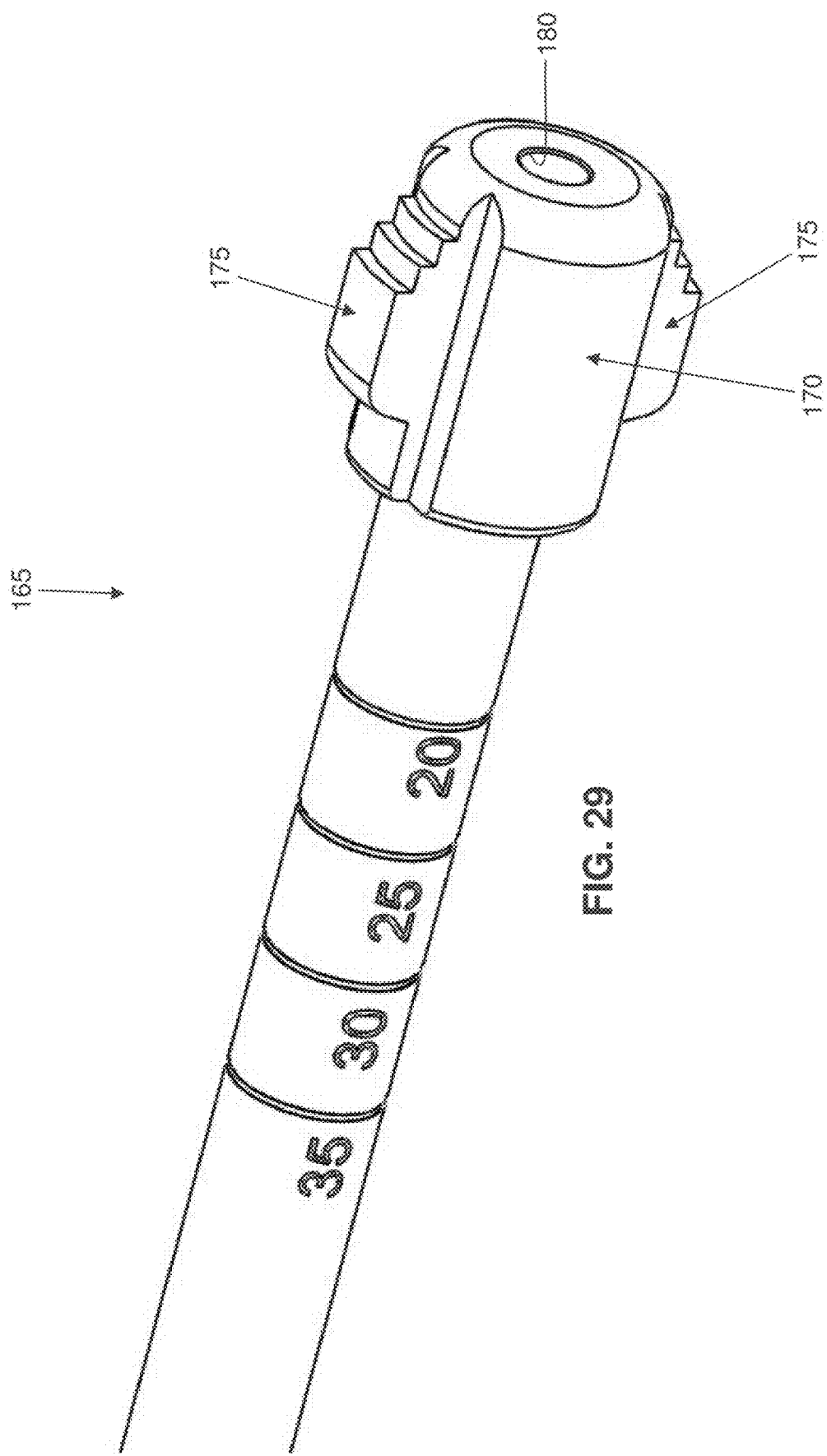

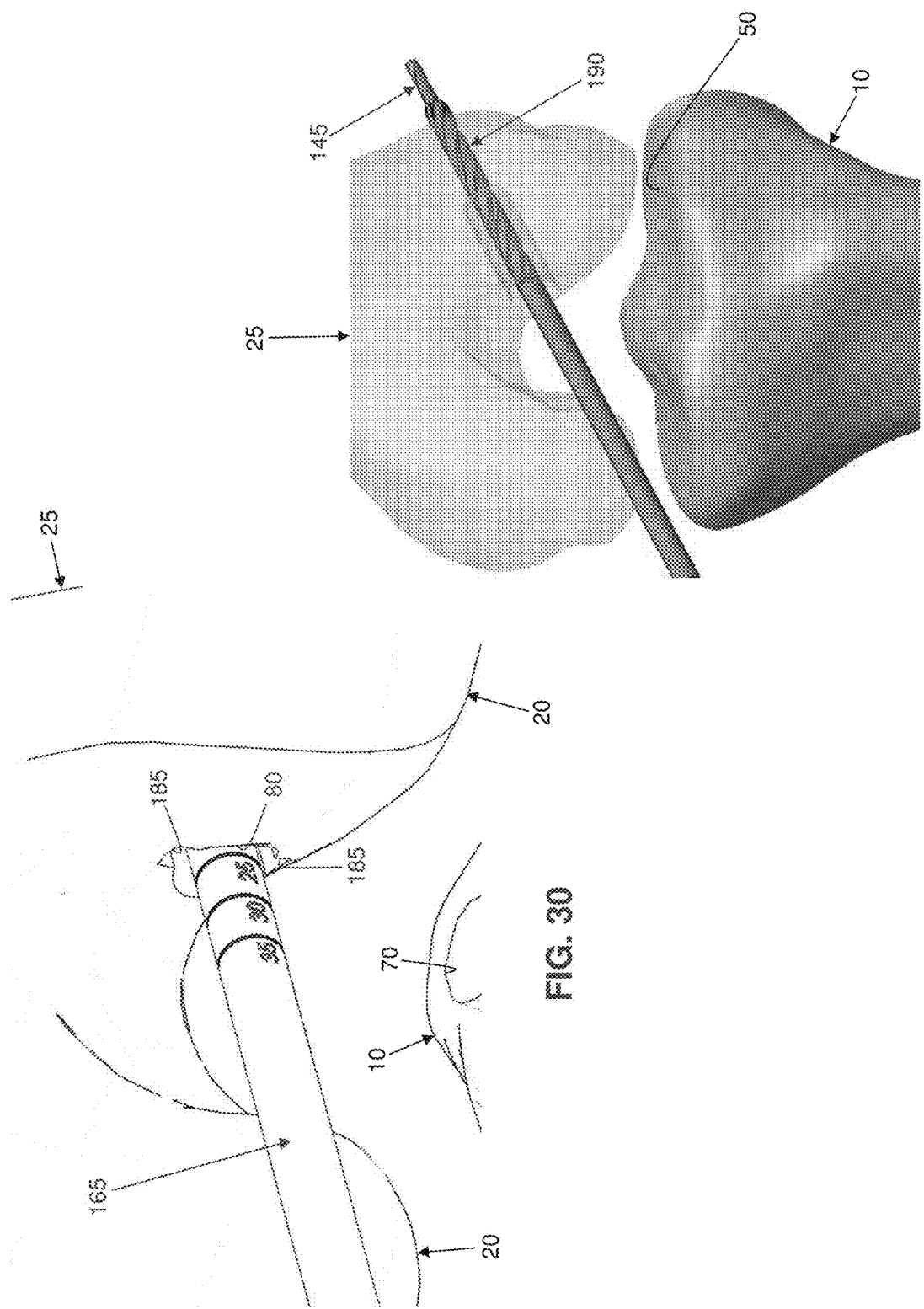

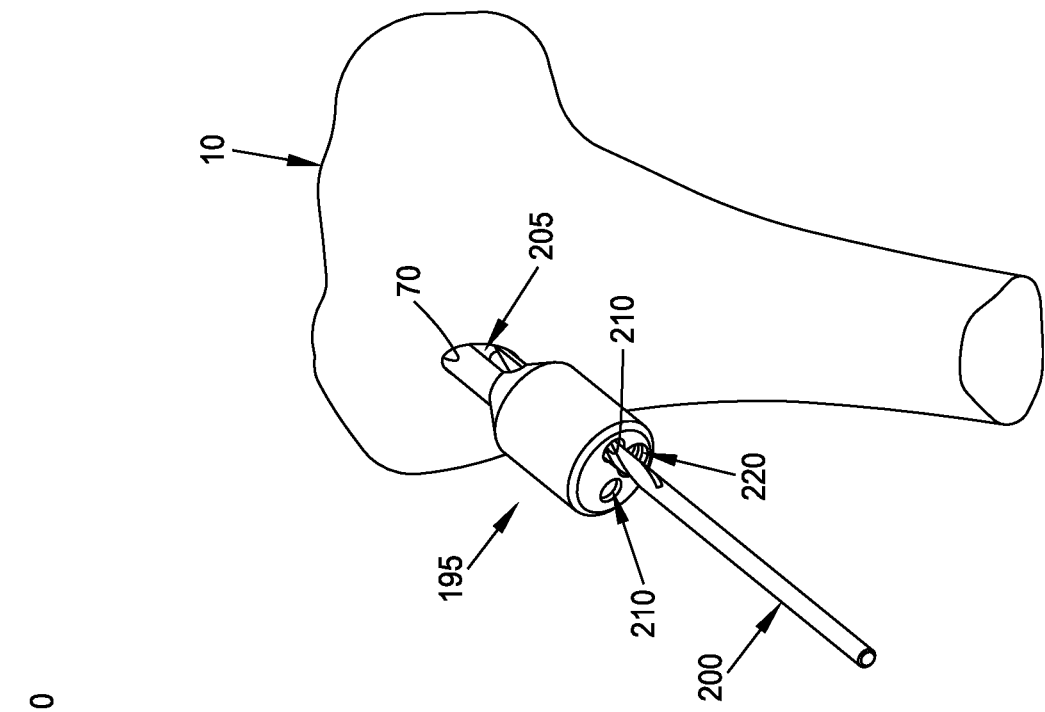
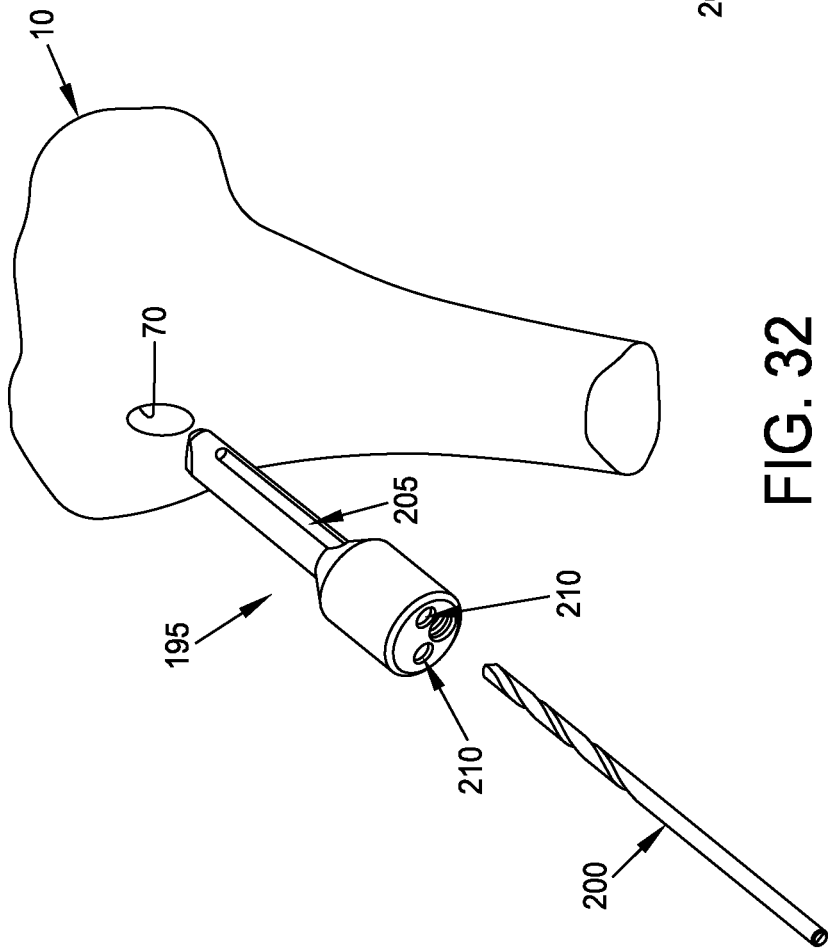
FIG. 32
FIG. 33

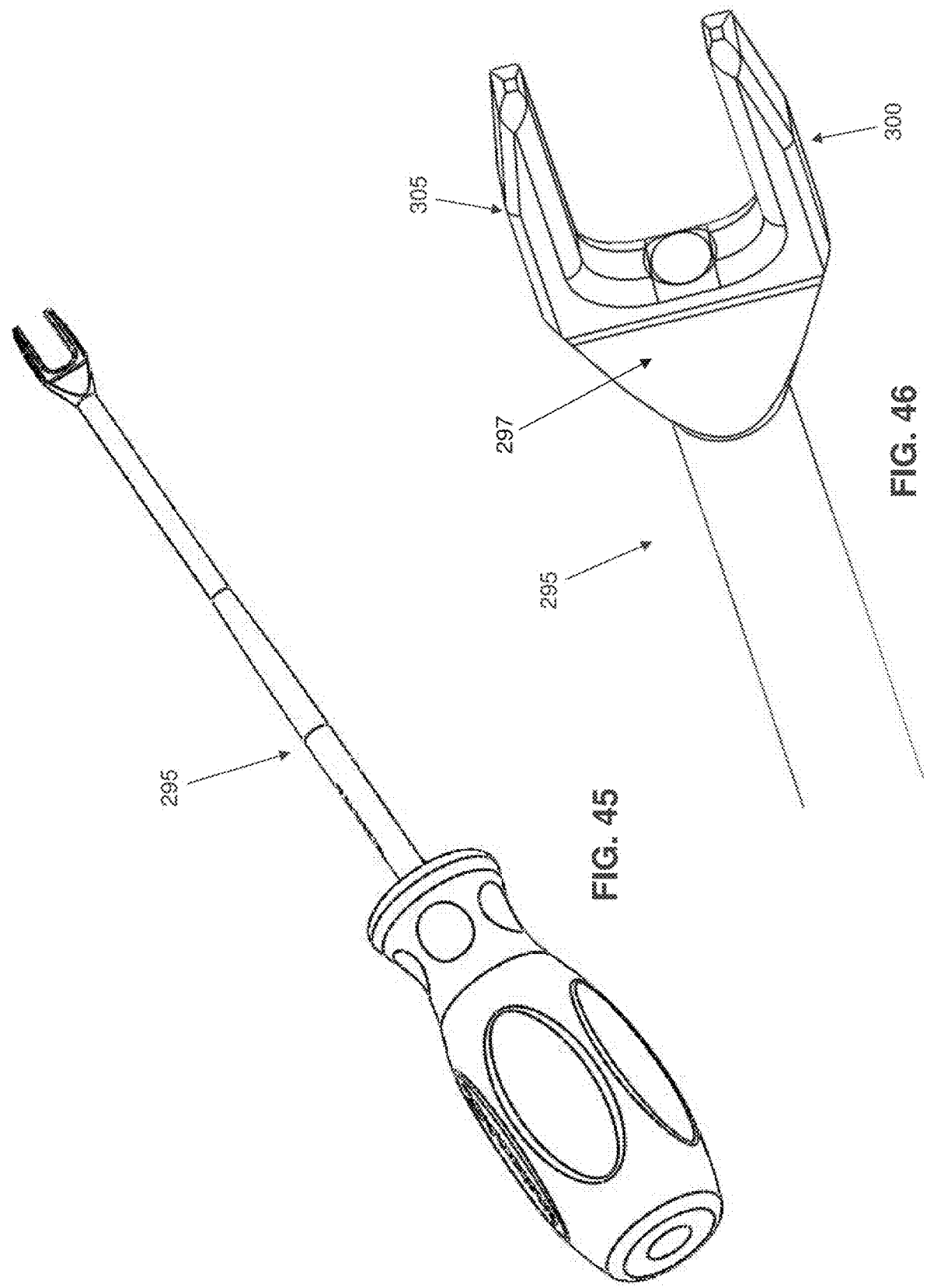

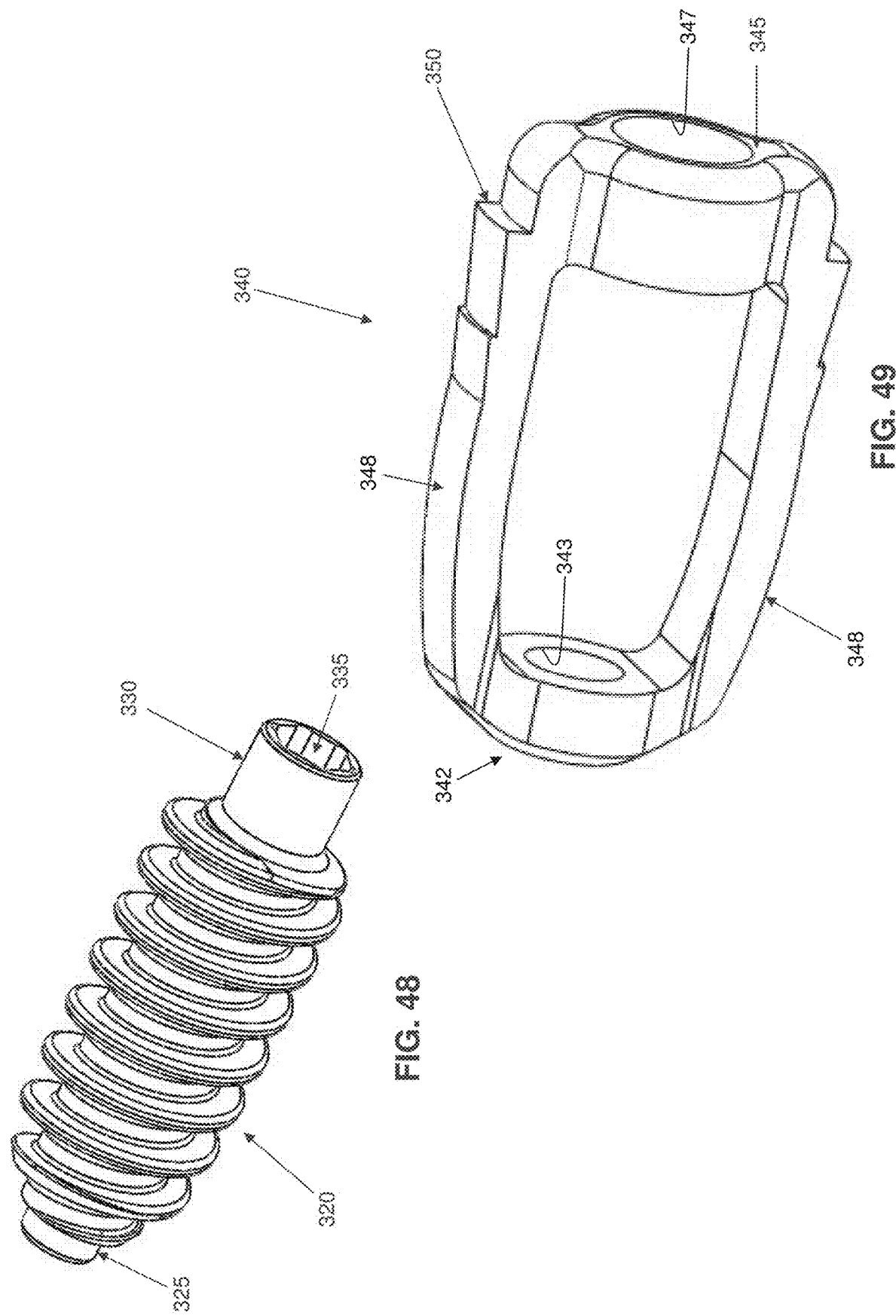

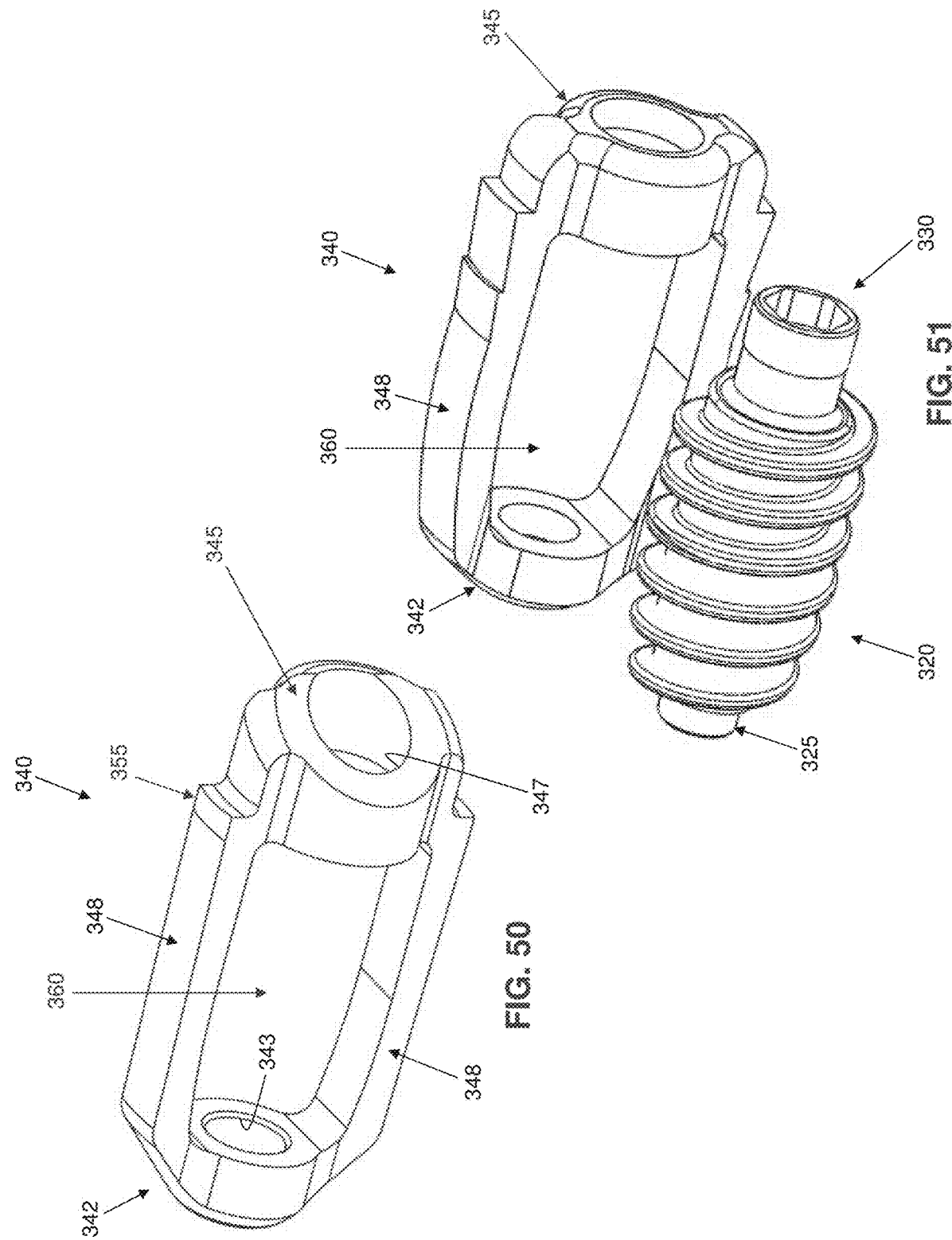

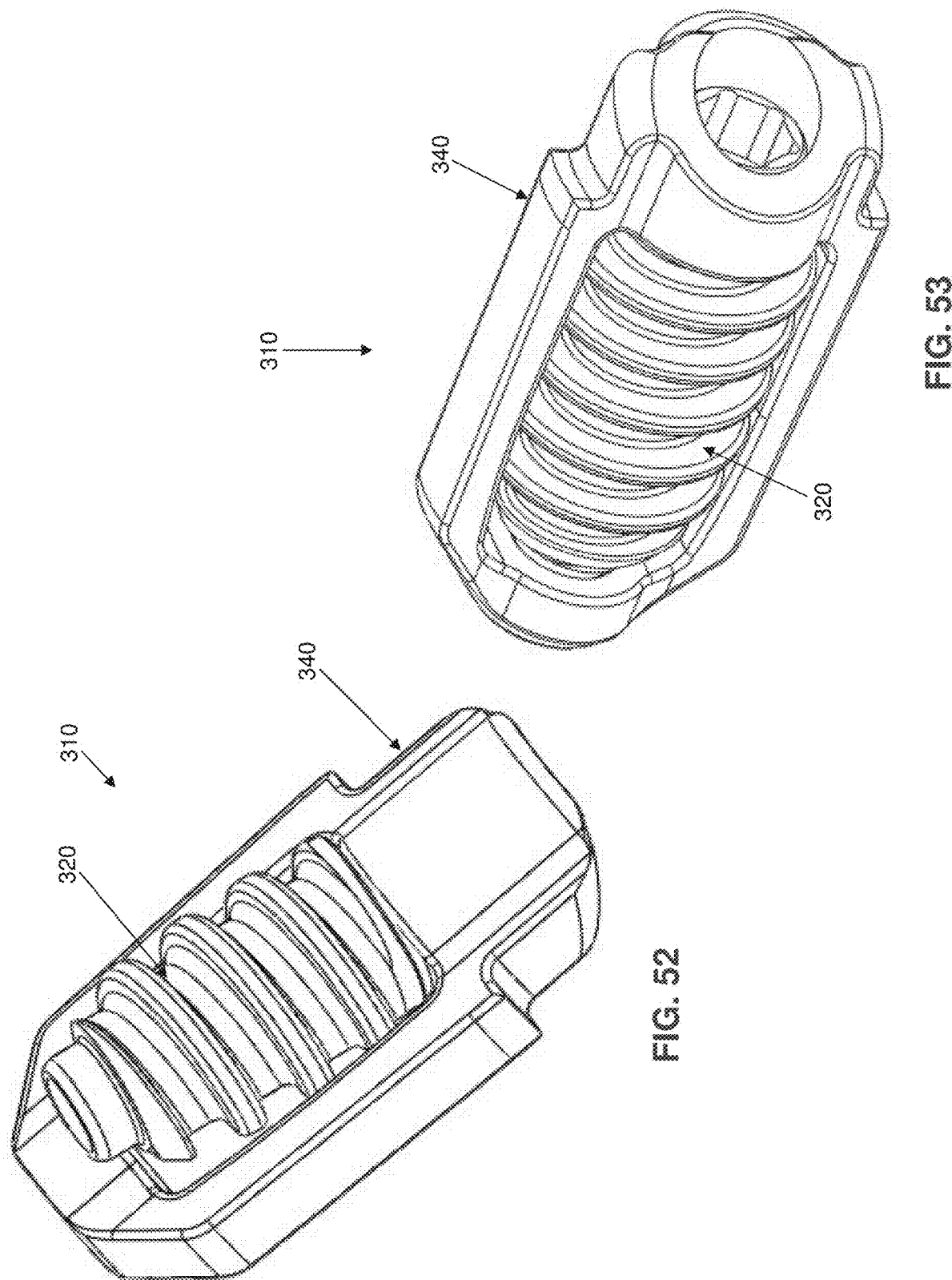

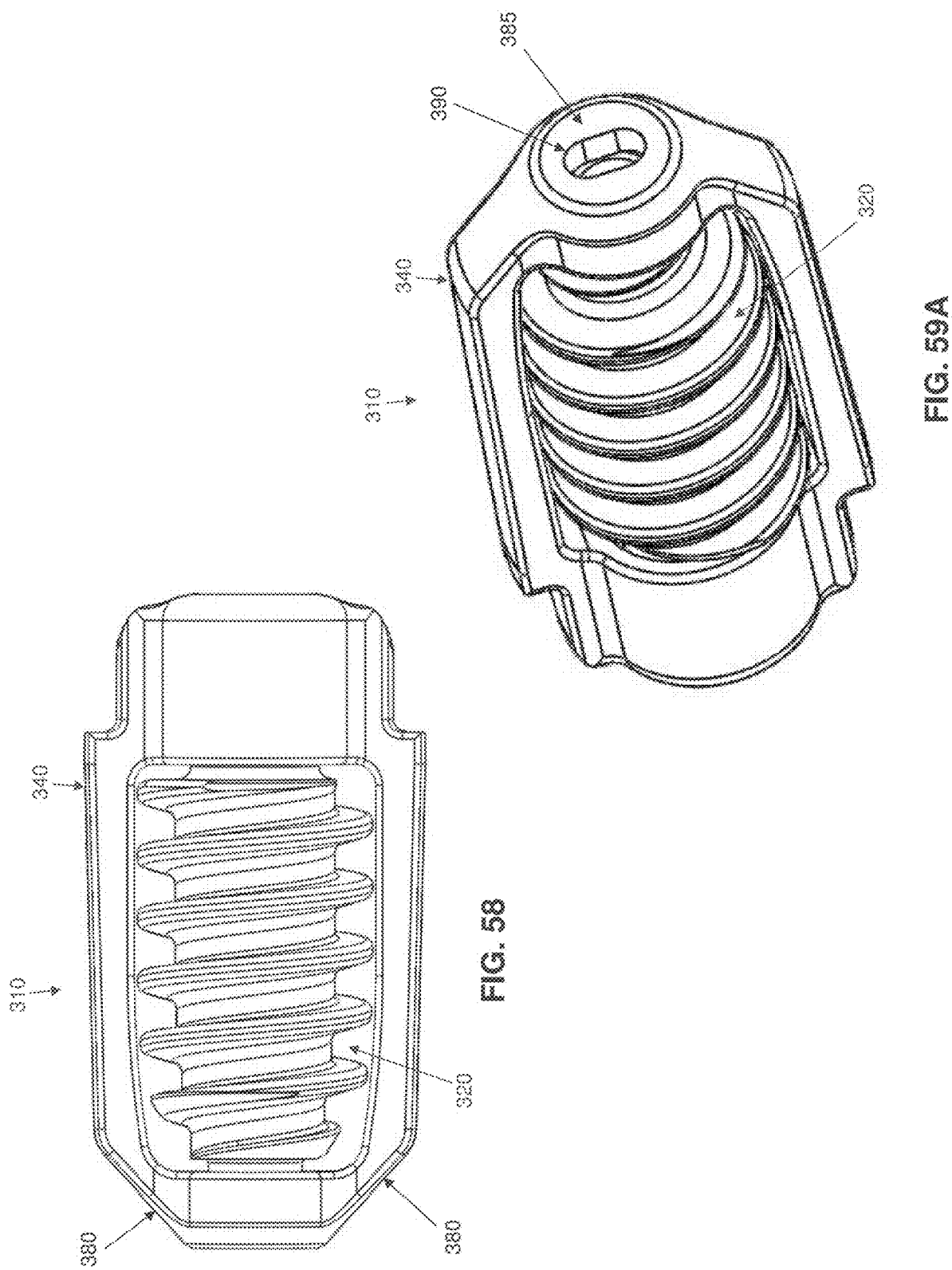

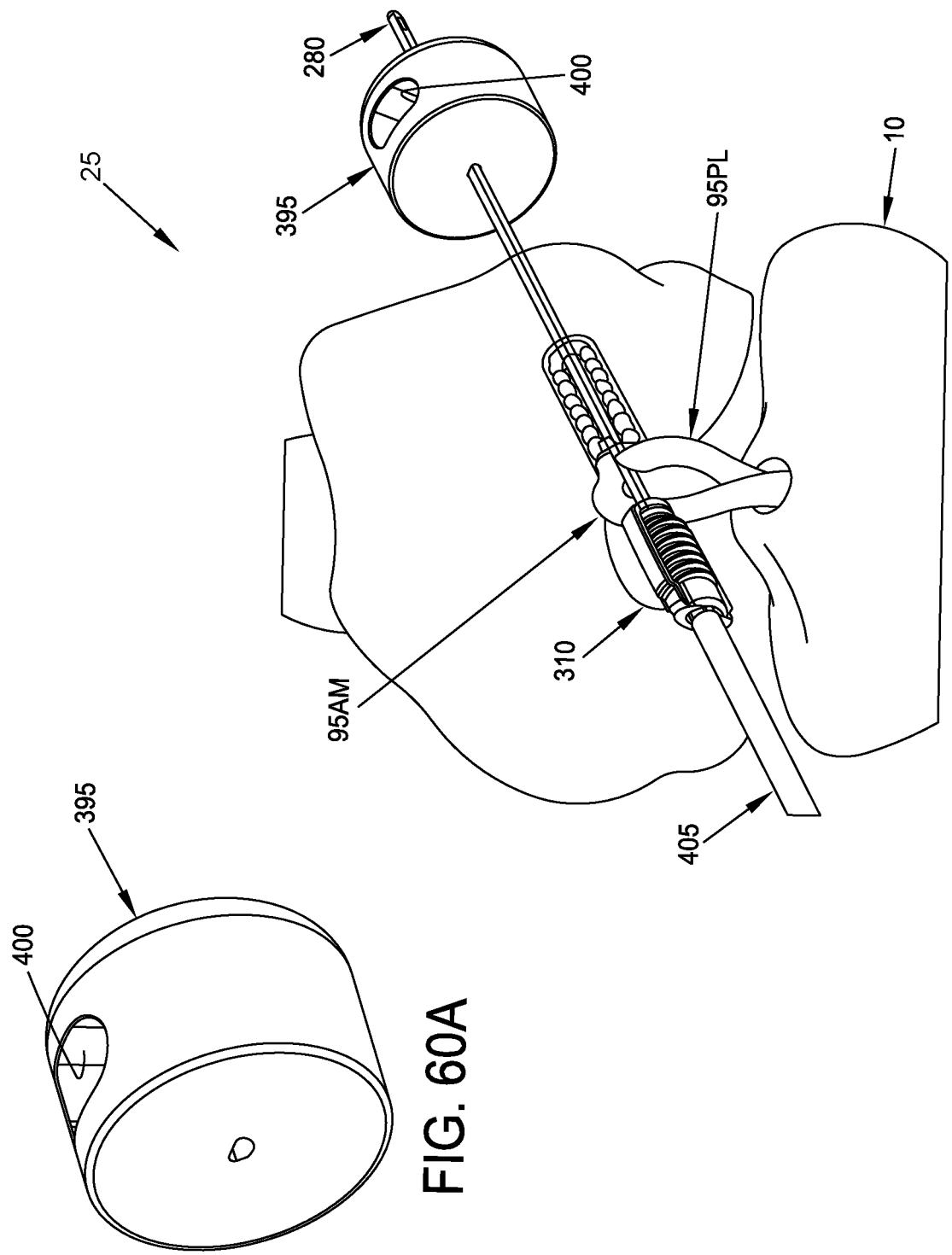

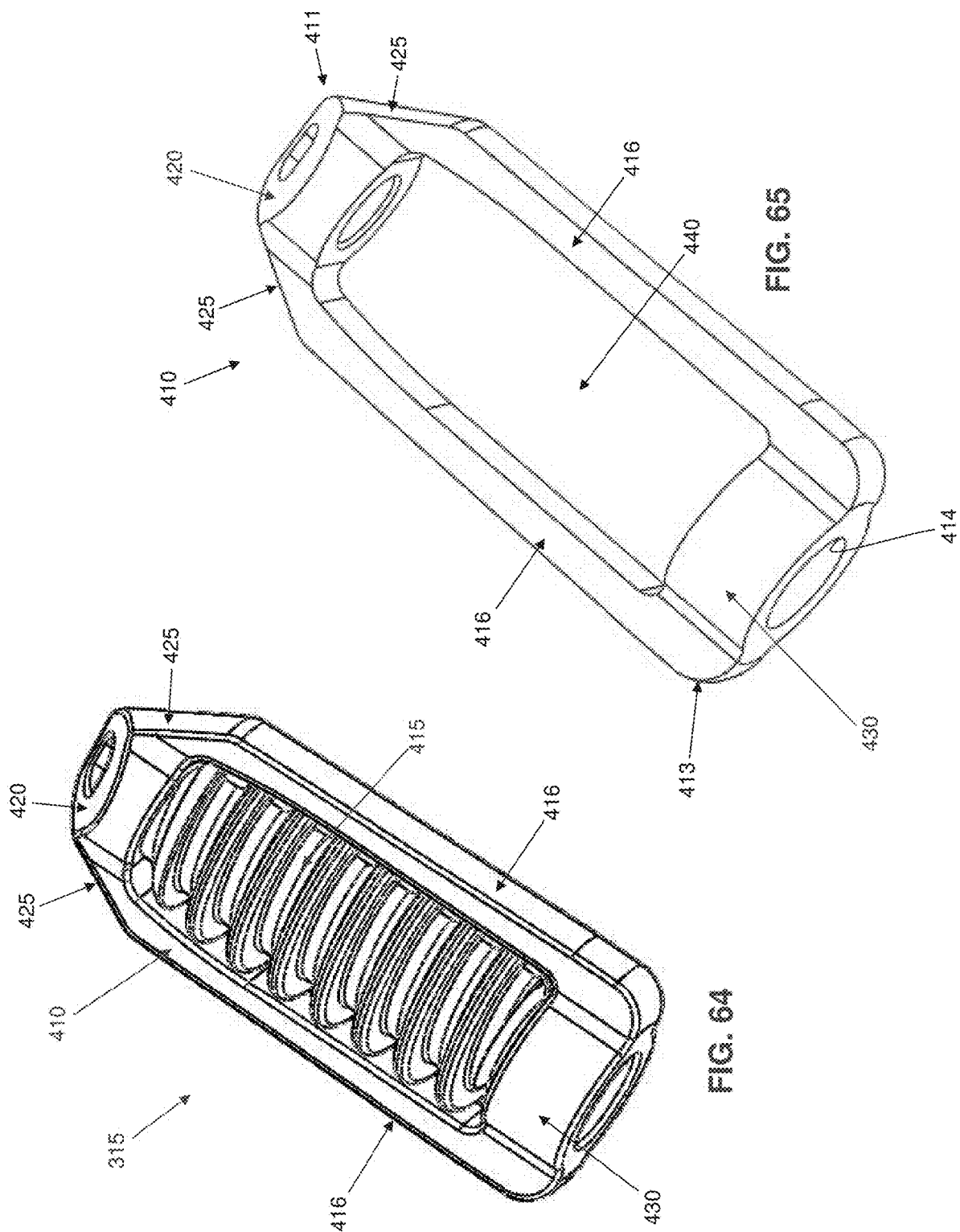

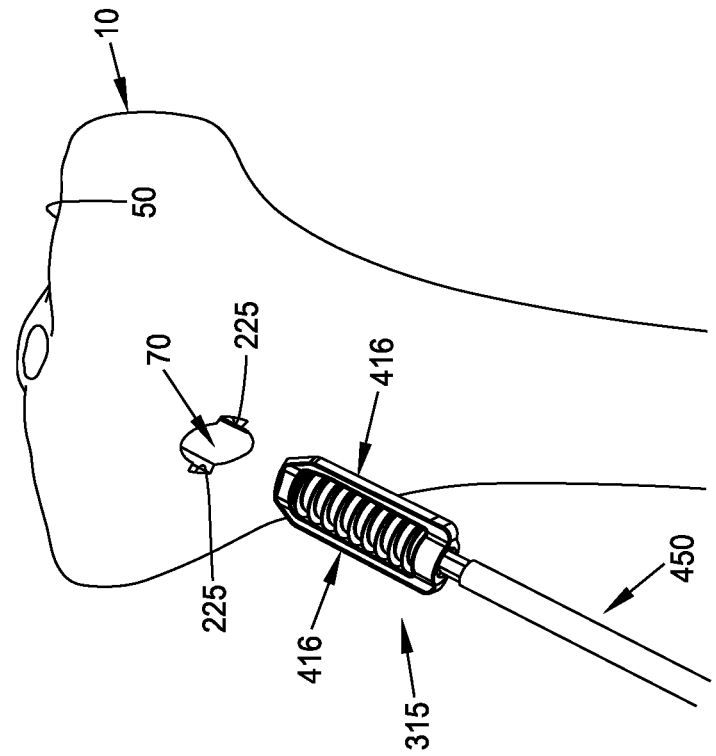
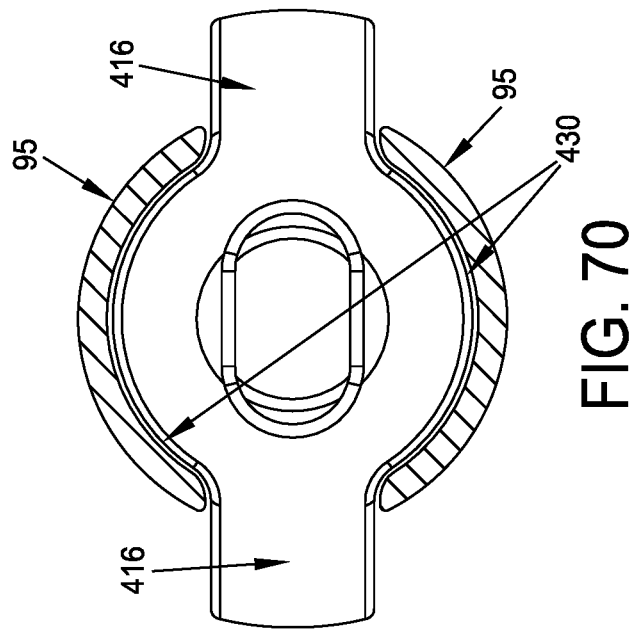

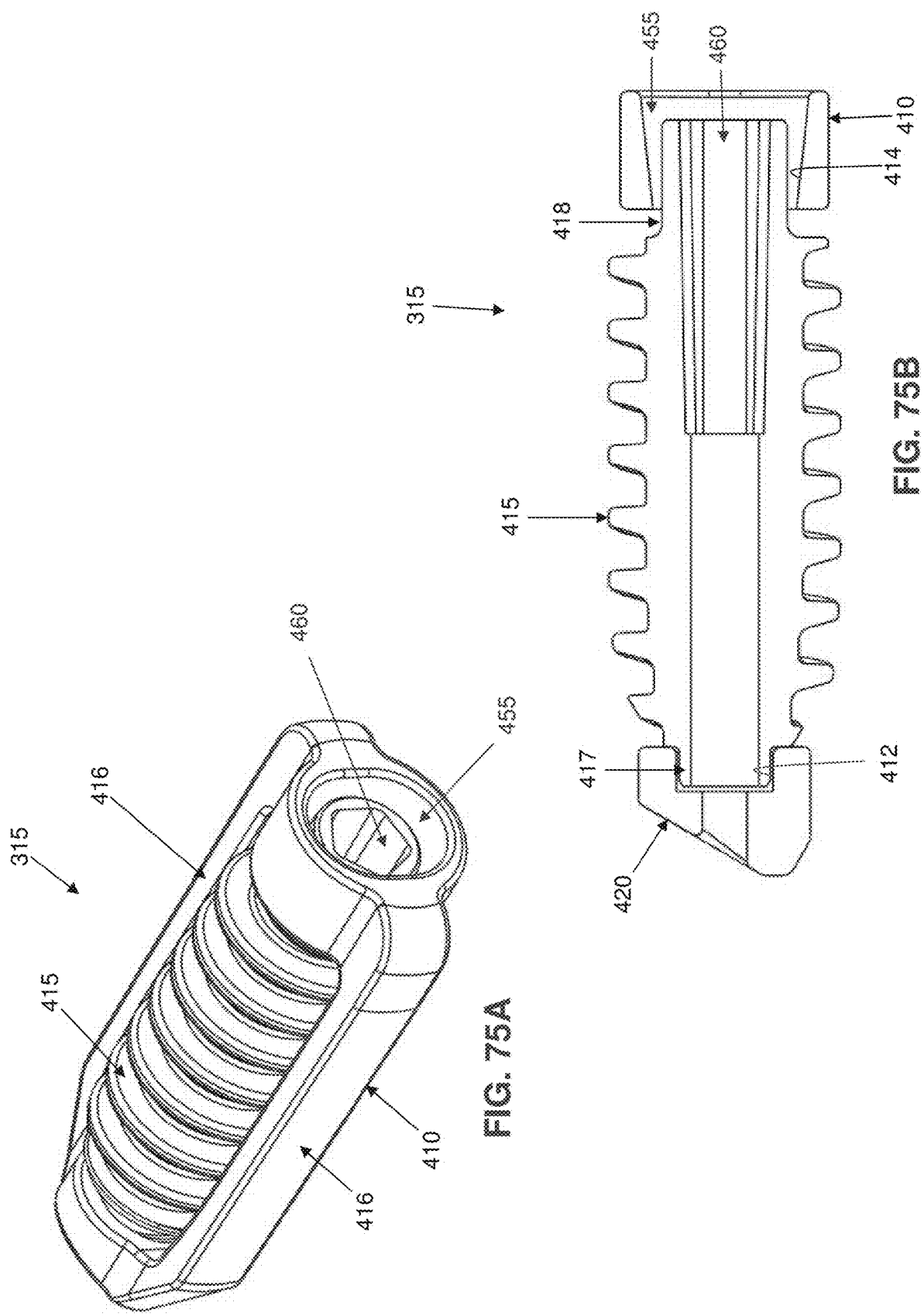

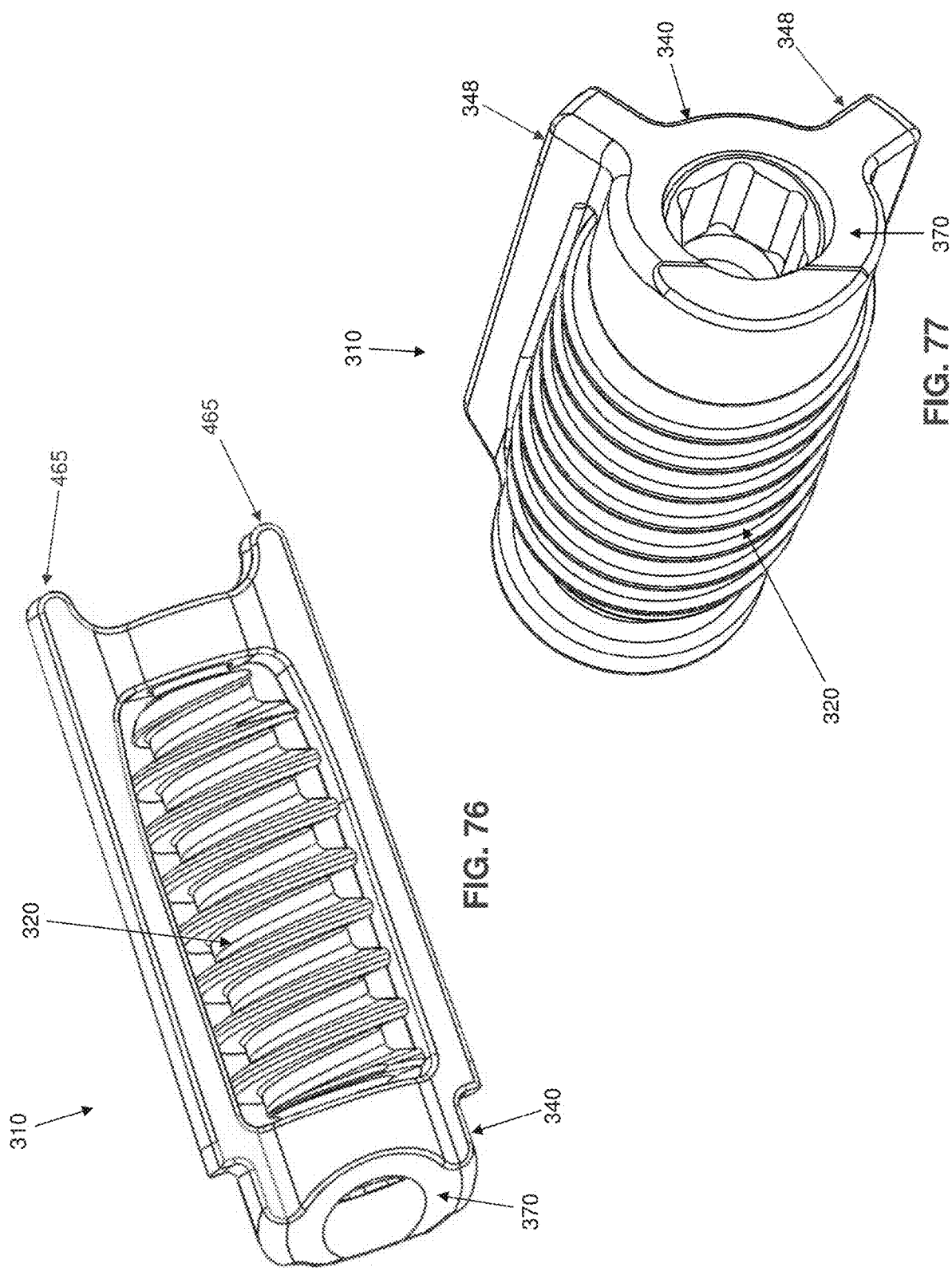

APPARATUS AND METHOD FOR ANATOMIC ACL RECONSTRUCTION

REFERENCE TO PENDING PRIOR PATENT APPLICATIONS

This patent application is a continuation of pending prior U.S. patent application Ser. No. 14/754,445, filed Jun. 29, 2015 by AnatomACL, LLC for APPARATUS AND METHOD FOR ANATOMIC ACL RECONSTRUCTION, which patent application in turn:

(i) is a continuation-in-part of prior U.S. patent application Ser. No. 13/528,680, filed Jun. 20, 2012 by Kelly G. Ammann for APPARATUS AND METHOD FOR LIGAMENT RECONSTRUCTION, which patent application in turn:
  (a) claims benefit of prior U.S. Provisional Patent Application Ser. No. 61/498,663, filed Jun. 20, 2011 by Kelly G. Ammann for APPARATUS AND METHOD FOR ANATOMIC ACL RECONSTRUCTION; and
  (b) claims benefit of prior U.S. Provisional Patent Application Ser. No. 61/638,848, filed Apr. 26, 2012 by Kelly G. Ammann for APPARATUS AND METHOD FOR ANATOMIC ACL RECONSTRUCTION;

(ii) is a continuation-in-part of pending prior U.S. patent application Ser. No. 14/397,370, filed Oct. 27, 2014 by Jortek Surgical, Inc. and Kelly G. Ammann for APPARATUS AND METHOD FOR LIGAMENT RECONSTRUCTION, which patent application in turn:
  (a) claims benefit of International (PCT) Patent Application No. PCT/US13/024145, filed Jan. 31, 2013 by Jortek Surgical, Inc. for APPARATUS AND METHOD FOR LIGAMENT RECONSTRUCTION; and
  (b) is a continuation-in-part of prior U.S. patent application Ser. No. 13/528,680, filed Jun. 20, 2012 by Kelly G. Ammann for APPARATUS AND METHOD FOR LIGAMENT RECONSTRUCTION, which patent application in turn claims benefit of:
    (1) prior U.S. Provisional Patent Application Ser. No. 61/498,663, filed Jun. 20, 2011 by Kelly G. Ammann for APPARATUS AND METHOD FOR ANATOMIC ACL RECONSTRUCTION; and
    (2) prior U.S. Provisional Patent Application Ser. No. 61/638,848, filed Apr. 26, 2012 by Kelly G. Ammann for APPARATUS AND METHOD FOR ANATOMIC ACL RECONSTRUCTION;

(iii) claims benefit of prior U.S. Provisional Patent Application Ser. No. 62/018,327, filed Jun. 27, 2014 by Jortek Surgical, Inc. and Kelly G. Ammann for APPARATUS AND METHOD FOR ANATOMIC ACL RECONSTRUCTION;

(iv) claims benefit of prior U.S. Provisional Patent Application Ser. No. 62/129,860, filed Mar. 8, 2015 by Jortek Surgical, Inc. and Kelly G. Ammann for APPARATUS AND METHOD FOR ANATOMIC ACL RECONSTRUCTION;

(v) claims benefit of prior U.S. Provisional Patent Application Ser. No. 62/137,888, filed Mar. 25, 2015 by Jortek Surgical, Inc. and Kelly G. Ammann for APPARATUS AND METHOD FOR ANATOMIC ACL RECONSTRUCTION; and (vi) claims benefit of prior U.S. Provisional Patent Application Ser. No. 62/175,733, filed Jun. 15, 2015 by AnatomACL, LLC and Kelly G. Ammann for APPARATUS AND METHOD FOR ANATOMIC ACL RECONSTRUCTION.

The ten (10) above-identified patent applications are hereby incorporated herein by reference.

FIELD OF THE INVENTION

This invention relates to medical apparatus and methods in general, and more particularly to medical apparatus and methods for reconstructing a ligament.

BACKGROUND OF THE INVENTION

A ligament is a piece of soft, fibrous tissue that connects one bone to another bone in the skeletal system. Ligaments can often become damaged or injured. When damaged or injured, ligaments may tear, rupture or become detached from bone. The loss of a ligament can cause instability, pain and eventually increased wear on joint surfaces, which can lead to osteoarthritis.

Various surgical techniques have been developed for ligament repair. The particular surgical technique used depends on the ligament that has been damaged and the extent of the injury.

One ligament which is commonly injured is the anterior cruciate ligament (ACL). As seen in FIG. 1, the ACL 5 extends from the top of the tibia 10 to the side of the notch 15 which is located between the femoral condyles 20 of the femur 25.

Trauma to the knee can cause injury to the ACL. The ACL may become partially or completely torn. FIG. 2 is a schematic view showing a torn ACL 5 in the left knee. An intact posterior cruciate ligament (PCL) 30 is shown behind the torn ACL 5.

A torn ACL reduces the stability of the knee joint and can result in pain, instability and excessive wear on the cartilage surfaces of the knee, eventually resulting in osteoarthritis.

Several approaches are available for ACL reconstruction. One of the most commonly used ACL reconstruction techniques involves removal of most, or all, of the torn ACL, drilling bone tunnels in both the femur and the tibia, inserting a tissue graft (sometimes referred to herein as simply "the graft") into the tibial and femoral tunnels so that the tissue graft extends across the interior of the knee joint in place of the native ACL, and securing the tissue graft in the femoral and tibial tunnels with interference screws or other fixation devices, so that the graft extends from the top of the tibia to the side of the femoral notch.

More particularly, and looking now at FIG. 3, an aiming instrument 35 is aligned to tibia 10 and a tibial guide pin 40 (for guiding a cannulated drill, see below) is drilled into tibia 10. FIG. 3 illustrates a typical aiming instrument 35 for targeting the tibial guide pin 40 from the outside of tibia 10 to an exit point 45 on the tibial plateau 50 at the location corresponding to the insertion point of the natural ACL. Note that tibial guide pin 40 enters tibia 10 at an angle α relative to the plane of tibial plateau 50, and exits the tibial plateau at the same angle α (relative to the plane of the tibial plateau).

After tibial guide pin 40 has been appropriately drilled through the tibia, aiming instrument 35 is removed from the tibia, leaving tibial guide pin 40 in place. As seen in FIG. 4, a cannulated drill 55 (i.e., a drill with a center hole extending along the length of the drill) is slid over tibial guide pin 40 and drilled from the anteromedial surface of tibia 10, through the tibia and into the joint space 60 of the knee. FIG. 4 shows tibial guide pin 40 and cannulated drill 55 after cannulated drill 55 has been drilled through tibia 10. In this way a tibial tunnel 70 may be formed in tibia 10, with the tibial tunnel extending from the anteromedial surface of the tibia to the insertion point of the native ACL on the tibial plateau.

A similar process may be followed for drilling into femur 25, i.e., a femoral guide pin 65 may be inserted through tibial tunnel 70 and into femur 25 as shown in FIG. 5, and then a cannulated drill 75 may be drilled over the femoral guide pin 65 and into femur 25. In this way a femoral tunnel 80 may be formed in femur 25, with the femoral tunnel extending from the side of the femoral notch to part or all the way through the femur. Ideally, the joint-side mouth of femoral tunnel 80 is located at the insertion point of the native ACL on the femoral notch.

The method described above and shown in FIG. 5 is sometimes referred to as "transtibial femoral tunnel drilling", since femoral tunnel 80 is drilled using access through tibial tunnel 70. One problem with transtibial femoral tunnel drilling is that the location of the joint-side mouth of femoral tunnel 80 typically ends up being higher in the femoral notch 15 than the insertion point of the natural ACL, because access to the femur is limited by the location and size of tibial tunnel 70.

On account of the foregoing, an alternative method has been developed to create femoral tunnel 80, i.e., by drilling the femoral tunnel using access through the "accessory medial portal". More particularly, accessory medial portal drilling of the femoral tunnel involves drilling across the knee joint through a medial portal skin incision 85 such that the joint-side mouth of femoral tunnel 80 can be placed in a more anatomic position. In accessory medial portal drilling, and looking now at FIG. 6, femoral guide pin 65 is first passed through medial portal skin incision 85 and is then drilled into the desired anatomic location on the femur (i.e., the insertion point of the natural ACL on the femur). Then a cannulated drill 75 is slid over femoral guide pin 65 and drilled into femur 25 so as to form femoral tunnel 80. Thus, femoral guide pin 65 and cannulated drill 75 enter through medial portal skin incision 85 and traverse across joint space 60 to the side of the femoral notch. As seen in FIG. 6, femoral guide pin 65 and cannulated drill 75 must enter in front of the adjacent femoral condyle 20 in order to prevent damaging the condyle. The knee quite often must be put into a state of deep flexion in order to reach the desired location (i.e., the insertion point of the natural ACL on the femur) and safely pass by the adjacent condyle 20 and tibial plateau 50.

Accessory medial portal drilling is generally considered to represent an improvement over transtibial femoral tunnel drilling in the sense that it can be used to create a more anatomic ACL reconstruction.

After tibial tunnel 70 and femoral tunnel 80 have been created, the tissue graft is prepared. The tissue graft is typically harvested from the patient's own body tissue and may comprise hamstring tendons, quadriceps tendons, and/or patellar tendons. Alternatively, similar tissue grafts may be harvested from a donor and also include Achilles tendons, anterior tibialis tendons or other graft sources. Looking now at FIG. 7, a tissue graft 90 is prepared by creating one or more long tissue graft strands or graft bundles 95, folding the graft over onto itself so as to create a folded section or loop 100, and making measurements along the graft. Example measurements for adults are 30 mm of graft length for the portion of the graft that is to be inserted into femoral tunnel 80, 27 mm to 30 mm for the portion of the graft that is intra-articular (i.e., inside the knee joint 60) and 35 mm for the portion that is to be positioned inside tibial tunnel 70. FIG. 7 shows tissue graft 90 folded over into two graft bundles 95 and a folded section or loop 100, and the corresponding graft measurements. Sutures (whipstitches) are typically applied at the areas of the graft that will interface with the femoral and tibial tunnels so as to add additional strength to the tissue graft. As will hereinafter be discussed, the folded section or loop 100 of tissue graft 90 will interface with femoral tunnel 80 and the two opposite ends (i.e., portion of graft bundles 95) will be disposed in tibial tunnel 70.

As seen in FIGS. 7 and 8, graft tow sutures 105 are looped around the folded portion or loop 100 of graft 90, forming a strand of sutures that can be used to pull graft 90 into place. More particularly, the free ends of graft tow sutures 105 are passed through tibial tunnel 70 and femoral tunnel 80, e.g., with the assistance of a suture passing guide wire (not shown) of the sort well known in the art. Once the free ends of graft tow sutures 105 have been passed through the tibial and femoral tunnels, the free ends of graft tow sutures 105 can be pulled so as to pull graft 90 into the tibial and femoral tunnels. FIG. 8 shows graft 90 folded over and in position to be pulled through tibial tunnel 70 and into femoral tunnel 80 using graft tow sutures 105. The graft tow sutures 105 emanating from the distal end of femoral tunnel 80 are grasped with a clamp 110, and clamp 110 and graft tow sutures 105 are used to pull graft 90 through tibial tunnel 70, across the interior of the knee joint, and into femoral tunnel 80.

Once tissue graft 90 is in place, the individual graft bundles 95 making up the aggregate tissue graft 90 may be manipulated to approximate the anatomic positions of the native ACL.

Advances in the research of ACL anatomy indicate that there are two primary bundles that make up the natural ACL, the anteromedial bundle and the posterolateral bundle. More particularly, and looking now at FIG. 9, the anteromedial bundle 115 and the posterolateral bundle 120 are also referred to as the "AM" bundle and the "PL" bundle. The particular name of the ligament bundle refers to its point of origin on tibial plateau 50, i.e., AM bundle 115 originates anteromedially and PL bundle 120 originates posterolaterally (relative to each other on the tibial plateau). As seen in FIG. 9, the AM and PL bundles are roughly parallel to each other when the knee is in full extension.

However, when the knee is fully flexed, and looking now at FIG. 10, AM bundle 115 and PL bundle 120 "cross" each other. As such, a true anatomic reconstruction of the ACL must place the graft bundles 95 into the proper femoral and tibial positions in order to achieve the natural kinematic motion of the ACL and the knee joint.

Thus, in an ACL reconstruction, it is desired to manipulate graft 90 into position such that the two graft bundles 95 (see FIGS. 7 and 8) making up the aggregate tissue graft 90 are located in the approximate positions of the natural AM and PL bundles of the native ACL. It has been demonstrated in biomechanical tests that this construct results in a more stable ACL reconstruction.

After graft 90 is inserted into the tibial and femoral tunnels, preferably with graft bundles 95 disposed so as to mimic the natural AM and PL bundles of the native ACL, fixation screws (also known as interference screws) are inserted into the femoral and tibial bone tunnels so as to secure graft 90 to femur 25 and tibia 10. More particularly, and looking now at FIG. 11, the femoral portion of graft 90 is first fixed into place by inserting a femoral interference screw 125 through the medial portal skin incision 85, advancing femoral interference screw 125 across the interior of the joint, and then screwing femoral interference screw 125 into femoral tunnel 80 e.g., with a driver 127. Femoral interference screw 125 squeezes graft 90 tightly against the wall of femoral tunnel 80. As femoral interference screw 125 is tightened into place, the femoral interference screw creates an interference fit between femoral tunnel 80, graft 90 and femoral interference screw 125.

FIG. 12 shows the femoral fixation in place, with AM bundle 95AM of graft 90 approximating the anatomic position of the native AM bundle and PL bundle 95PL of graft 90 approximating the anatomic position of the native PL bundle.

Finally, and looking now at FIG. 13, a tibial interference screw 130 is screwed into tibial tunnel 70 so as to secure graft 90 in tibial tunnel 70.

The foregoing technique has been used for many years for the reconstruction of a damaged or injured ACL. This technique has generally been successful, but it does have some limitations. Typically, the location of graft 90 around the perimeter of interference screws 125, 130 is uncontrolled because the graft bundles 95 rotate as the interference screws are inserted. As a result, it is difficult to set the interference screws while keeping AM bundle 95AM and PL bundle 95PL in their correct anatomical positions.

Furthermore, on the tibial side, tibial interference screw 130 may skive off the centerline of tibial tunnel 70 as tibial interference screw 130 is screwed into place. As a result, the AM and PL bundles 95AM, 95PL may bunch up and migrate to one side of tibial tunnel 70. This occurrence creates a non-anatomic reconstruction which may also result in reduced pull-out strength and can contribute to changes in the natural motion of the knee. Clinically, this occurrence may contribute to tunnel widening where the tibial interference screw 130 skives off to one side of the tibial tunnel and the AM and PL bundles 95AM, 95PL are bunched up on the other side of the tibial tunnel, causing the softer cancellous bone inside the tibia to collapse. FIG. 14 illustrates how the off-center disposition of tibial interference screw 130 can result in a non-anatomic reconstruction: the AM and PL bundles 95AM, 95PL may not be located in their correct anatomic positions; at various degrees of knee flexion, one of the bundles may become excessively slack; the overall strength of the construct may be reduced; and natural knee motion may be altered, contributing to the development of osteoarthritis or an increase in the need for subsequent revision surgery.

A closer analysis of how the tibial and femoral tunnels 70, 80 are formed, and a closer look at the anatomic insertions of graft 90 into the femur and tibia, illustrate how graft fixation can be configured to produce a more anatomic reconstruction.

Because cannulated drill 75 enters the surface of femur 25 at an angle (FIGS. 5 and 6), the entrance of femoral tunnel 80 is elliptical (FIG. 15). This elliptical shape is not due to poorly manufactured drills, poor surgical technique, etc. It is the normal result of drilling a hole into a surface while the drill is set at a non-perpendicular angle to the surface. This is illustrated in FIG. 15, which shows the outline of femoral tunnel 80 when looking directly into the bone surface.

Similarly, when cannulated drill 55 exits tibial tunnel 70 and enters the interior of the joint at an angle (FIG. 4), the shape of the tunnel opening is elliptical at the tibial plateau 50 (FIG. 16).

This elliptical shape of the joint-side entrance of femoral tunnel 80 and at the joint-side exit of tibial tunnel 70 has been documented in biomechanical studies.

For reference, the normal anatomic ACL insertion shape, or morphology, on the surface of the femur is shown in FIG. 17. The AM and PL bundles 115, 120 are shown in typical anatomic locations.

Similarly, the normal anatomic ACL insertion shape on the surface of the tibia are shown in FIG. 18. The AM and PL bundles 115, 120 are shown in typical anatomic locations.

Typical interference screws fixate graft 90 along the length of the interference screws, with the graft located between the interference screw and the side wall of the bone tunnel. See FIG. 19, which shows femoral interference screw 125 securing graft 90 to femur 25. However, as discussed above and as shown in FIG. 14, the two graft bundles 95 of graft 90 do not typically lie in the true anatomic AM and PL bundle locations because graft bundles 95 rotate with the rotation of the interference screws before coming to rest in their final fixed position.

In a similar fashion, graft bundles 95 may rotate or be compressed into non-anatomic positions at the entrance of tibial tunnel 70.

In addition, with respect to tibial fixation, the curved taper at the tip of an interference screw lies near the joint-side exit of tibial tunnel 70, and this distal taper of the interference screw creates some laxity of graft 90. FIG. 20 shows the AM graft bundle 95AM and the PL graft bundle 95PL shown approximately in their anatomic positions. The area at the distal end of interference screw 130 shows how graft 90 is loosely fixated in the area near the distal tip of the interference screw. This loose fixation of graft 90 may contribute to problems such as the so-called "windshield wiper effect", where graft 90 sweeps across the opening of the bone tunnel, thereby causing abrasion to the graft and to the bone tunnel; and joint laxity due to incomplete fixation of the graft into its anatomic position.

Thus there are problems with standard interference screw fixation: the graft bundles may come to rest around the interference screw in non-anatomic locations, resulting in a biomechanical construct that does not replicate the native anatomy; there is a lack of complete fixation of the graft at the opening of the bone tunnel to the joint space; and the unsecured graft in the elliptical opening of the bone tunnel may contribute to the windshield wiper effect, biomechanical instability and tunnel widening.

Another type of graft fixation in common use is sometimes referred to as suspensory fixation. In suspensory fixation, and looking now at FIG. 21, graft 90 is passed through a fabric loop 135 which is, in turn, secured to a button 140. Button 140, loop 135 and graft 90 are inserted into a femoral bone tunnel 80, and button 140 is "flipped" outside the distal bone cortex so as to suspend the graft in the femoral tunnel. In one variation of this technique, and as is shown in FIG. 21, anatomic reconstruction is effected by creating two femoral bone tunnels 80, one for the AM bundle 95AM and one for the PL bundle 95PL.

As also seen in FIG. 21, a similar approach may be used on the tibial side.

Furthermore, if desired, and as is also shown in FIG. 21, an interference screw 142 may also be used to enhance femoral or tibial fixation.

In this type of ligament reconstruction, the grafts 90 are freely suspended in the femoral tunnel(s) 80. Micro-movement of graft 90 due to loading and unloading of the graft tissue may contribute to tunnel widening and loss of fixation. Also, the location of the graft bundles 95 in the femoral tunnel(s) is to some extent uncontrolled, inasmuch as the graft bundles are free to rotate and translate laterally, and to a smaller extent axially, within the femoral tunnel(s).

The previously-described approaches illustrate much of the current practice of ACL reconstruction. Current approaches do not lend themselves to creating a highly accurate anatomic reconstruction. The current devices can result in constructs that do not fully stabilize the graft. The subsequent motion of the graft may contribute to tunnel widening, loss of graft tension, loss of knee stability and may result in the need for subsequent revision surgery.

SUMMARY OF THE INVENTION

A new and improved approach for ACL reconstruction is disclosed herein. The object of the present invention is to secure the graft bundles to the femur and the tibia such that they are oriented and positioned in the true anatomic locations of the native ACL insertions. This orientation and positioning results in fixation of the graft AM bundle and the graft PL bundle near the natural anatomic footprints of the native AM bundle and native PL bundle at the tibia and femur. Furthermore, the graft AM bundle and the graft PL bundle are more effectively secured within the femoral and tibial bone tunnels, eliminating micro-movement within the bone tunnels.

In one preferred form of the present invention, there is provided a graft fixation device comprising:

a graft separator comprising a distal end, a proximal end, a cavity disposed between said distal end and said proximal end, and at least one guide rib disposed radially outboard of said cavity and extending between said distal end and said proximal end; and an interference screw rotatably mountable within said cavity, said interference screw comprising a distal end, a proximal end, and a screw thread disposed intermediate thereof, said screw thread disposed radially outboard of at least a portion of said graft separator and radially inboard of said at least one rib.

In another preferred form of the present invention, there is provided a tibial graft separator for separating the AM bundle and PL bundle of an ACL graft for disposition in a notched tibial tunnel, wherein the notched tibial tunnel comprises a bore and a pair of diametrically-opposed notches opening on the bore and extending diametrically outboard of the bore, said tibial graft separator comprising:

an elongated planar body having a distal end, a proximal end, a first side extending from said distal end to said proximal end, and a second side extending from said distal end to said proximal end; and a raised rim extending along said first side and said second side;

wherein said tibial graft separator is sized to be received within said notched tibial tunnel, with a first portion of said raised rim being disposed in one of the pair of diametrically-opposed notches, a second portion of said raised rim being disposed in the other of the pair of diametrically-opposed notches, and with said elongated planar body bifurcating the bore of the notched tibial tunnel into two passageways.

In another preferred form of the present invention, there is provided a femoral graft separator for separating the AM bundle and PL bundle of an ACL graft for disposition in a notched femoral tunnel, wherein the notched femoral tunnel comprises a bore and a pair of diametrically-opposed notches opening on the bore and extending diametrically outboard of the bore, said femoral graft separator comprising:

an elongated planar body having a distal end, a proximal end, a first side extending from said distal end to said proximal end, and a second side extending from said distal end to said proximal end, said first and second sides having a taper; and a shaft connected to said proximal end of said elongated planar body;

said elongated planar body and said shaft being cannulated;

wherein said femoral graft separator is sized to be received within said notched femoral tunnel, with a portion of said first side being disposed in one of the pair of diametrically-opposed notches, a portion of said second side being disposed in the other of the pair of diametrically-opposed notches, and with said elongated planar body bifurcating the bore of the notched femoral tunnel into two passageways.

In another preferred form of the present invention, there is provided a femoral graft separator for separating the AM bundle and PL bundle of an ACL graft for disposition in a notched femoral tunnel, wherein the notched femoral tunnel comprises a bore and a pair of diametrically-opposed notches opening on the bore and extending diametrically outboard of the bore, said femoral graft separator comprising:

a body having a distal end, a proximal end, a first projection extending distally from said distal end of said body, and a second projection extending distally from said distal end of said body; and a shaft connected to said proximal end of said body;

said body and said shaft being cannulated;

wherein said femoral graft separator is sized to be received within said notched femoral tunnel, with said first projection being disposed in one of the pair of diametrically-opposed notches, said second projection being disposed in the other of the pair of diametrically-opposed notches, and with said body bifurcating the bore of the notched femoral tunnel into two passageways.

In another preferred form of the present invention, there is provided a method for securing a graft in a bone tunnel, wherein the graft comprises a first graft bundle and a second graft bundle, said method comprising:

forming a notched bone tunnel comprising a bore and a pair of diametrically-opposed notches opening on the bore and extending diametrically outboard of the bore;

advancing the graft into the notched bone tunnel;

advancing a graft bundle separator into the notched bone tunnel so as to bifurcate the bore of the notched bone tunnel into two passageways and to separate the first graft bundle and the second graft bundle, with the first graft bundle being in one of the two passageways and the second graft bundle being in the other of the two passageways, and advancing an interference screw into the notched bone tunnel so as to secure the first and second graft bundles to the side wall of the notched bone tunnel.

In another preferred form of the present invention, there is provided a method for reconstructing a ligament, said method comprising:

providing a graft comprising a first graft bundle and a second graft bundle;

forming a first notched bone tunnel in a first bone, the first notched bone tunnel comprising a bore and a pair of diametrically-opposed notches opening on the bore and extending diametrically outboard of the bore, and forming a second notched bone tunnel in a second bone, the said notched bone tunnel comprising a bore and a pair of diametrically-opposed notches opening on the bore and extending diametrically outboard of the bore;

advancing the graft through the first notched bone tunnel and into the second notched bone tunnel;

advancing a graft bundle separator into the second notched bone tunnel so as to bifurcate the bore of the second notched bone tunnel into two passageways and to separate the first graft bundle and the second graft bundle, with the first graft bundle being in one of the two passageways and the second graft bundle being in the other of the two passageways, and advancing an interference screw into the second notched bone tunnel so as to secure the first and second graft bundles to the side wall of the second notched bone tunnel; and advancing a graft bundle separator into the first notched bone tunnel so as to bifurcate the bore of the first notched bone tunnel into two passageways and to separate the first graft bundle and the second graft bundle, with the first graft bundle being in one of the two passageways and the second graft bundle being in the other of the two passageways, and advancing an interference screw into the first notched bone tunnel so as to secure the first and second graft bundles to the side wall of the first notched bone tunnel.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 18 is a schematic view showing the natural insertion of the ACL on the tibia;

FIG. 19 is a schematic view showing how the AM and PL graft bundles of the ACL may rotate with an interference screw;

FIGS. 22-25 are schematic views showing creation of a femoral tunnel in accordance with the present invention;

FIGS. 28-31 are schematic views showing the femoral tunnel being notched and thereafter drilled through to the distal side of the femur;

FIGS. 32-36 are schematic views showing the tibial tunnel being notched;

FIGS. 42, 43, 43A and 44-47 are schematic views showing the graft of FIG. 41 being inserted into a femoral tunnel;

FIGS. 47A, 48-58 and 59A are schematic views showing a femoral fixation device formed in accordance with the present invention;

FIGS. 59B, 60A, 60B and 61-63 are schematic views showing a femoral fixation device being inserted into a femoral tunnel;

FIGS. 64-72 are schematic views showing a tibial fixation device being inserted into a tibial tunnel;

FIGS. 75A, 75B and 76-78 are schematic views showing alternative forms of the femoral fixation device and the tibial fixation device.

DETAILED DESCRIPTION OF THE PREFERRED EMBODIMENTS

Bone Tunnel Formation

In accordance with the present invention, and looking now at FIG. 22, the femoral tunnel is prepared by placing a femoral guide pin 145 into the anatomic location of the native femoral ACL insertion. It is desirable for femoral guide pin 145 to enter the intercondylar notch 15 at an angle, to avoid the adjacent medial condyle 20 as well as the tibial plateau 50.

From a top view (FIG. 23), with the knee in 90° of flexion, the path of femoral guide pin 145 is shown as it passes by the medial condyle 20 and enters the medial aspect of the intercondylar notch 15. Femoral guide pin 145 enters at an angle β from the sagittal plane. The angle β must be great enough to ensure that femoral guide pin 145 passes by the adjacent medial condyle 20 without contacting the medial condyle.

Placement of femoral guide pin 145 in this manner allows access to the true anatomic insertion point of the native ACL.

Figure 24:
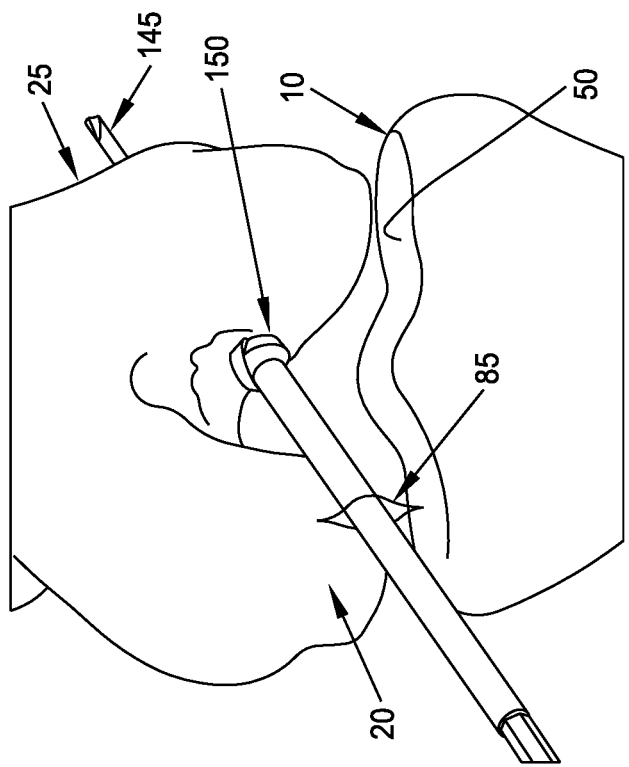

A cannulated drill 150 is then slid over femoral guide pin 145, advanced through medial portal skin incision 85, past the medial condyle 20 and tibial plateau 50 and into the anatomic location of the native femoral ACL insertion, as shown in FIG. 24.

Figure 25:
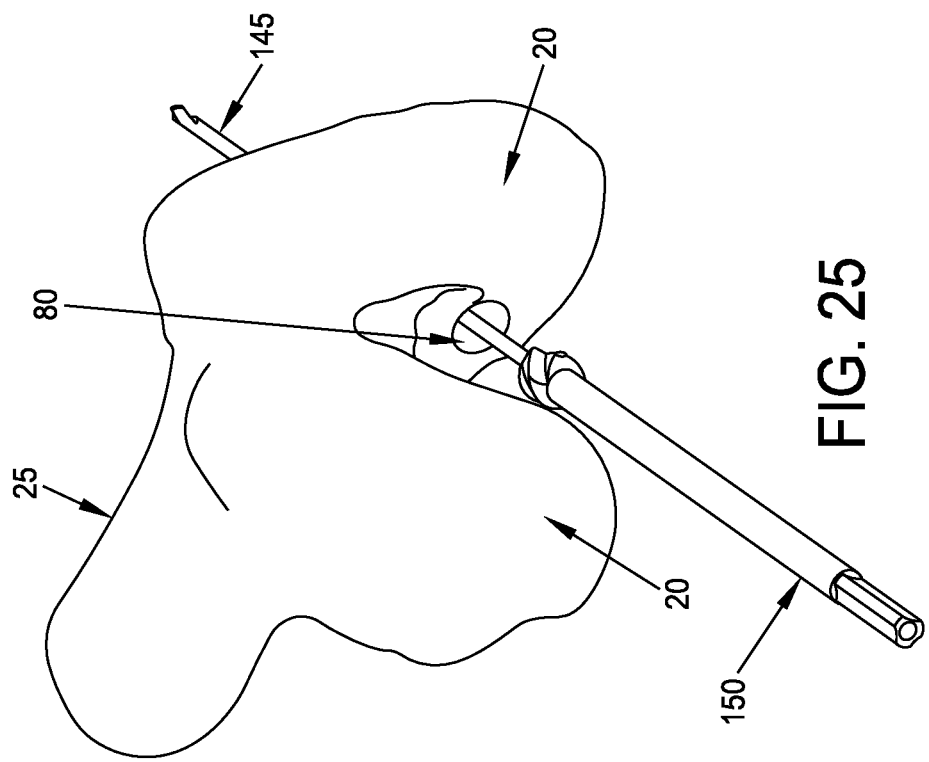

The femoral tunnel 80 is then drilled using cannulated drill 50 and the result is a circular bore hole with an elliptical tunnel entrance, as shown in FIG. 25. This portion of the technique is generally similar to that which was discussed above, except that it is completed with an understanding that, with the present invention, and as will hereinafter be discussed in further detail, the angled entrance of femoral tunnel 80 contributes in a positive manner in creating a more anatomic femoral fixation. As such, the surgeon does not try to "straighten out" the femoral tunnel so as to achieve a circular entrance, but rather may actually slightly increase the angle β so as to achieve the more anatomic elliptical entrance (i.e., to match the native anatomic insertion of the natural ACL on the femur). Furthermore, it is helpful, when using the femoral fixation approach described below, to make certain adjustments to the drilling of the femoral tunnel. For one thing, the length of the femoral tunnel should be drilled 5 mm-10 mm longer than the anticipated femoral fixation length. This allows for the graft to expand into the distal end of the femoral tunnel as the fixation squeezes the graft tightly up against the side wall of the femoral tunnel. Also, on the femoral side, it is useful to drill the tunnel 0.5 mm-1.0 mm larger than the measured graft diameter.

Figures 26, 27:
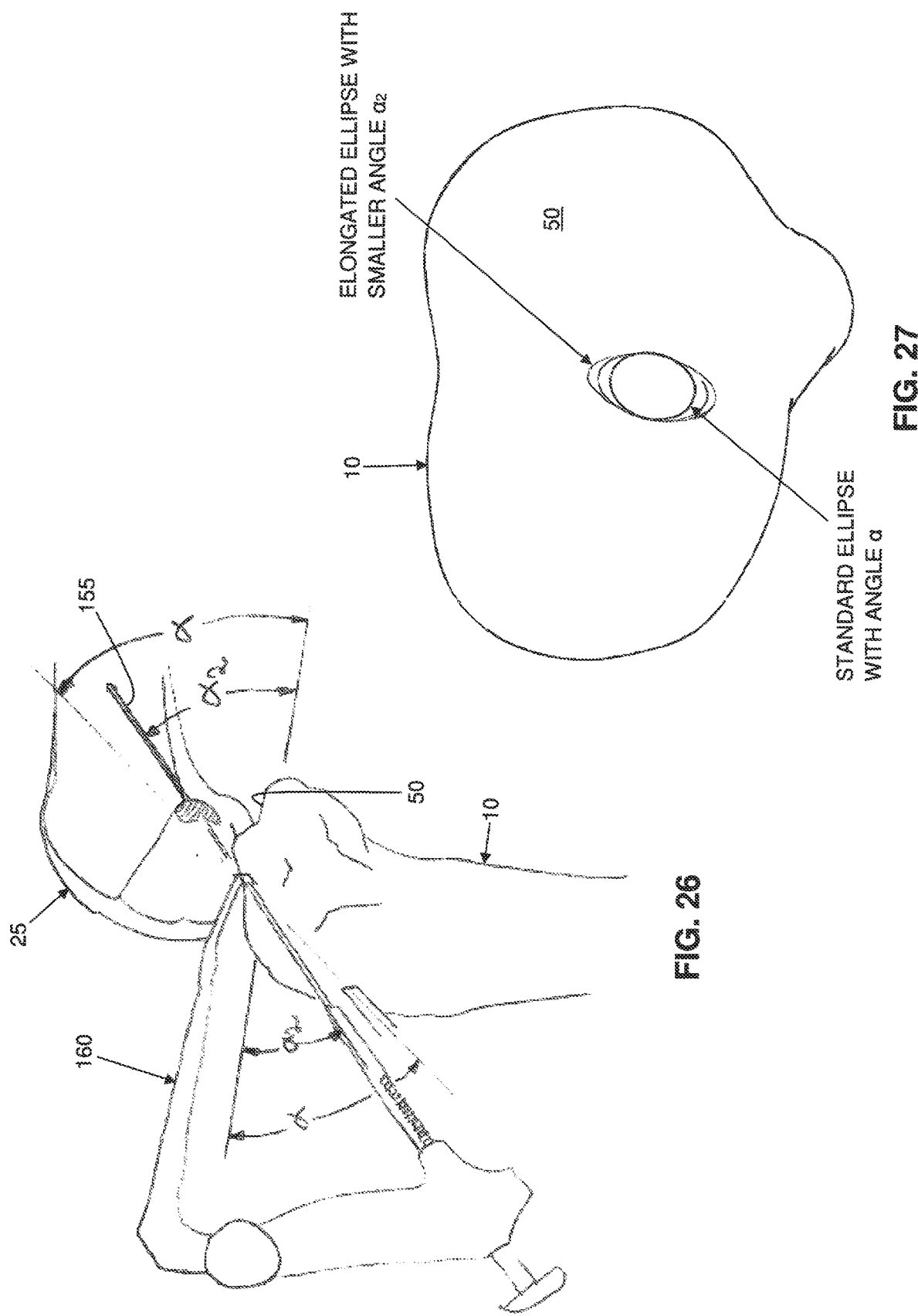
FIGS. 26 and 27 are schematic views showing creation of a tibial tunnel in accordance with the present invention.

Similarly, and looking now at FIG. 26, the tibial tunnel is prepared by first drilling a tibial guide pin 155 (with the aid of a drill guide 160) through the anteromedial surface of the tibia, exiting through the anatomic center of the desired ACL insertion on tibial plateau 50 (i.e., in the manner previously described). The tibial drilling angle, $\alpha_2$, can be smaller than the traditional tibial drilling angle $\alpha$ in a traditional ACL reconstruction, because the elliptical/oval nature of the tibial tunnel exit on the tibial plateau contributes to the anatomic reconstruction of the present invention. This can be a significant advantage over the prior art, since a shorter tibial tunnel (a consequence of drilling at angle $\alpha_2$ rather than at angle $\alpha$) means less trauma to the tibia and more space on the anteromedial surface of the tibia below the tibial tunnel (which may be used for other surgical procedures, if needed). Drill guide 160 is removed and a cannulated drill (not shown in FIG. 26, but generally similar to cannulated drill 150 discussed above) is placed over tibial guide pin 155. This cannulated drill is then drilled from the outside of the tibia through to the tibial plateau 50, passing through the natural anatomic footprint of the native ACL insertion. FIG. 27 illustrates the effect of drilling at the angle $\alpha_2$ (rather than at the conventional angle $\alpha$) at the exit of the tibial tunnel onto tibial plateau 50. The exit of tibial tunnel 70 onto tibial plateau 50 becomes a more elongated ellipse, increasing the footprint of the graft insertion and contributing to a more anatomic reconstruction, as will hereinafter be discussed in further detail.

The present invention comprises a further unique step in the preparation of the femoral and tibial bone tunnels. More particularly, and looking now at FIG. 28, after creating the anatomically-placed tibial and femoral tunnels 70, 80, each of the tunnels is "notched" (e.g., with two diametrically-opposed notches) using a notching instrument (or "notcher") 165 that is designed to closely and specifically match the pre-drilled tunnel while adding diametrically-opposed notches to the tunnel. These notches are placed at the natural bifurcation (split) locations of the AM and PL bundles 95AM, 95PL (i.e., the plane of the two diametrically-opposed notches is aligned with the natural bifurcation plane of the AM and PL bundles 95AM, 95PL). In the case of femoral tunnel 80, femoral guide pin 145 is retained in the femur after the femoral tunnel drilling has been completed. Notcher 165 is cannulated. Notcher 165 is slid over the femoral guide pin 145 and brought into proximity with femoral tunnel 80, as shown in FIG. 28.

Figure 28:
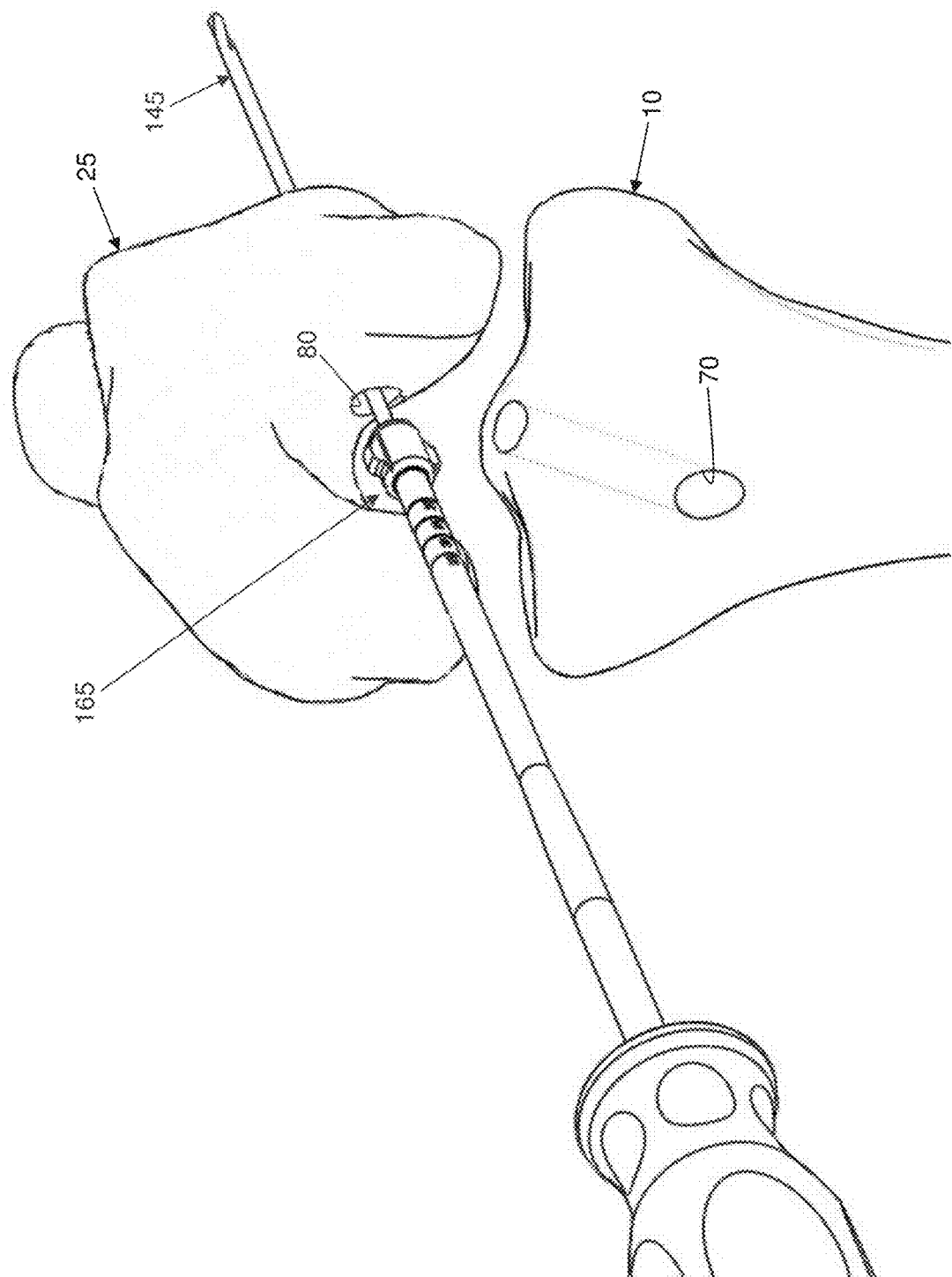

In one preferred form of the present invention, and as seen in FIGS. 28 and 29, notcher 165 comprises a cylindrical tip 170 that closely matches the diameter of femoral tunnel 80. Two stepped protrusions 175 emanate from opposing sides of cylindrical tip 170, creating a form of broaching tool. The center opening (or cannulation) 180 of notcher 165 slides over femoral guide pin 145 so as to center notcher 165 in femoral tunnel 80.

As seen in FIG. 30, notcher 165 is driven into the femur, preferably to the depth of the drilled femoral bone tunnel, by hand or with a mallet, forming channels (or notches) 185 along the femoral bone tunnel 80. See FIG. 30.

After notching the femoral tunnel, notcher 165 is removed from femoral guide pin 145 and then a smaller 4.5 mm to 5.0 mm cannulated drill 190 is passed over femoral guide pin 145 and drilled through the distal cortex of femur 25. This extends the distal end of femoral tunnel 180 all the way through femur 25 for later use. See FIG. 31.

On the tibial side, similar notches are created for tibial tunnel 70. However, in the absence of an emplaced tibial guide pin to support notcher 165 on the tibial side (i.e., tibial guide pin 40 is removed from the tibia after tibial tunnel 70 is formed, since there is no grounding for the distal end of tibial guide pin 40 after the tibial tunnel is drilled completely through to tibial plateau 50), and considering the hardness of the cortical bone surface on the anteromedial surface of tibia 10, two holes (see below) are drilled (using a tibial notcher drill guide and drill, see below) in the approximate area of the desired tibial notches and these two holes are then used to guide notcher 165 as the notches are formed in the tibia for tibial tunnel 70.

The tibial notcher drill guide 195 and drill 200 are shown in FIG. 32.

As seen in FIG. 33, tibial notcher drill guide 195 is inserted into the previously-drilled tibial tunnel 70. The two channels 205 (only one of which is seen in FIGS. 32 and 33) on the side of tibial notcher drill guide 195, which connect with openings 210 formed on the proximal end of tibial notcher drill guide 195, are aligned with the location of the desired anatomic split which is to be achieved between the AM and PL bundles. Drill 200 is then used to drill into one opening 210 and along channel 205 on one side of tibial notcher drill guide 195, and to drill into the other opening 210 on the other side of tibial notcher drill guide 195 and along the channel 205 on the other side of tibial notcher drill guide 195, thereby forming two side holes 215 (see FIG. 34) which intersect with the larger tibial tunnel 70 and provide a guide for the stepped protrusions 175 of notcher 165 when notcher 165 is used to form notches in the tibial tunnel (see below). A larger threaded hole 220 (FIG. 33) at the lower middle part of tibial notcher drill guide 195 may be used to secure a threaded tool to tibial notcher drill guide 195, to aid in the insertion or removal of tibial notcher drill guide 195 from tibial tunnel 70. FIG. 33 shows tibial notcher drill guide 195 in place and drill 200 about to make one of the side holes 215 for notcher 165. Side holes 215 are preferably drilled through the tibia up to the subchondral bone, without entering the joint space.

Figure 34:
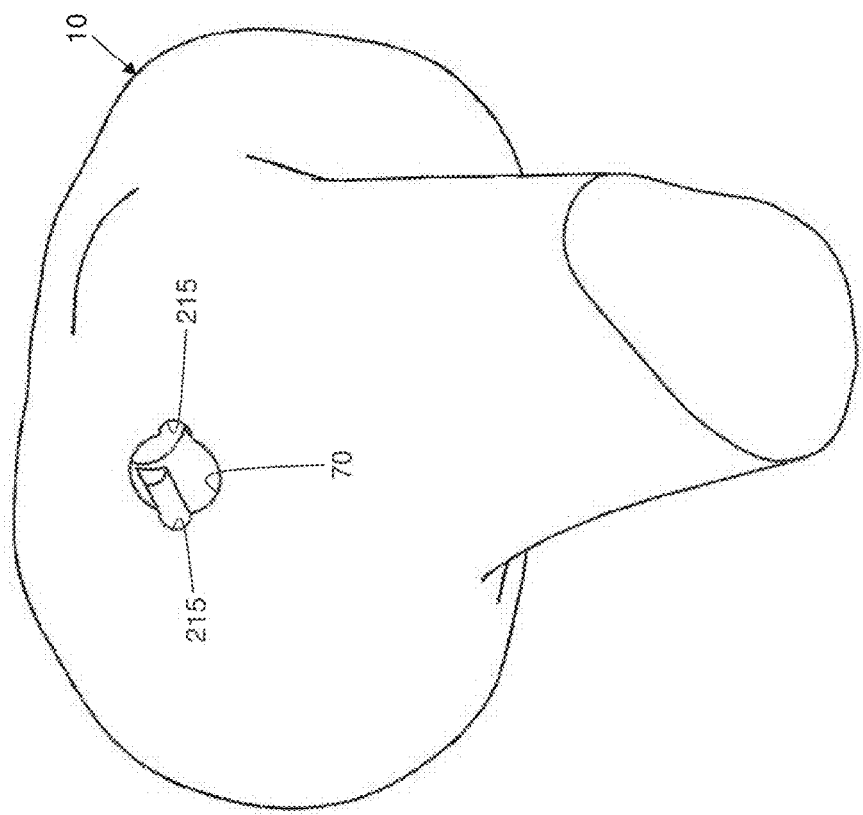

The tibia, with tibial tunnel 70 and side holes 215 for receiving notcher 165, is shown in FIG. 34.

Figure 35:
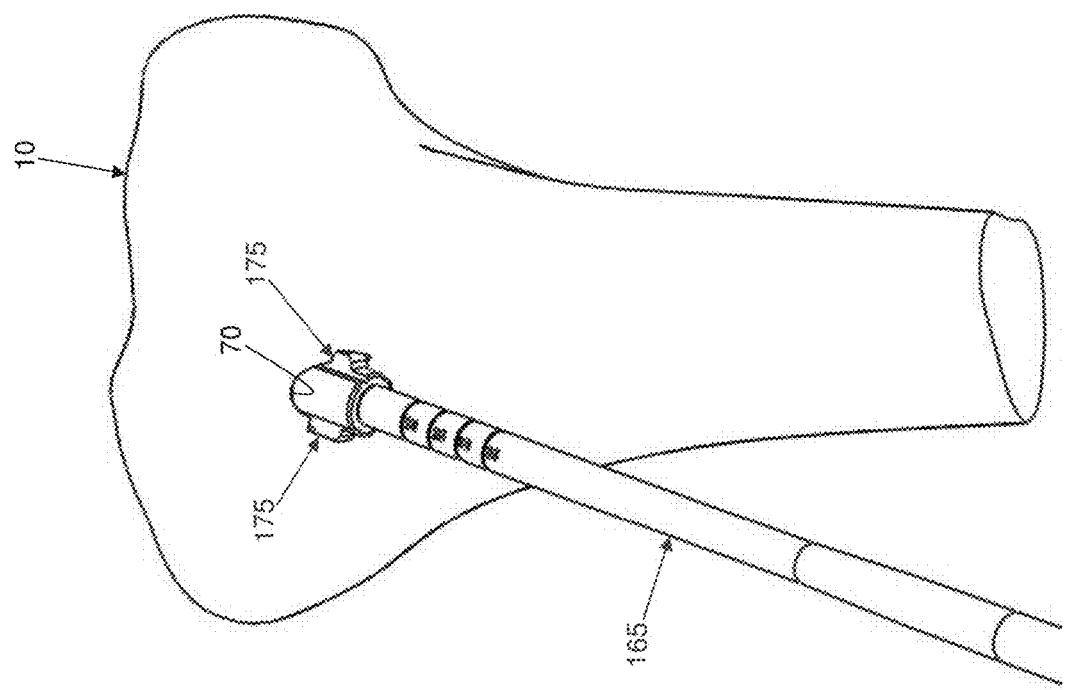

Then, and looking now at FIG. 35, notcher 165 is brought into proximity with tibial tunnel 70, the stepped protrusions 175 of notcher 165 are aligned with side holes 215 in the tibia, and the notcher is driven along the tibial tunnel, forming channels (or notches) 225 along the tibial tunnel, in a manner similar to the manner in which notches 185 were formed along the femoral tunnel. Notcher 165 is generally not driven all the way through the tibia and into the joint space, but is only driven up to the subchondral bone surface (i.e., notcher 165 is driven into tibia 10 to the same depth that the two side holes 215 are drilled into tibia 10). This creates a subchondral bone surface at the distal ends of tibial notches 225 for the subsequently-placed tibial fixation device (see below) to rest on, thus increasing the strength of the tibial fixation.

FIG. 35 shows notcher 165 entering tibial tunnel 70 in order to create the tibial tunnel notches 225.

Figure 36:
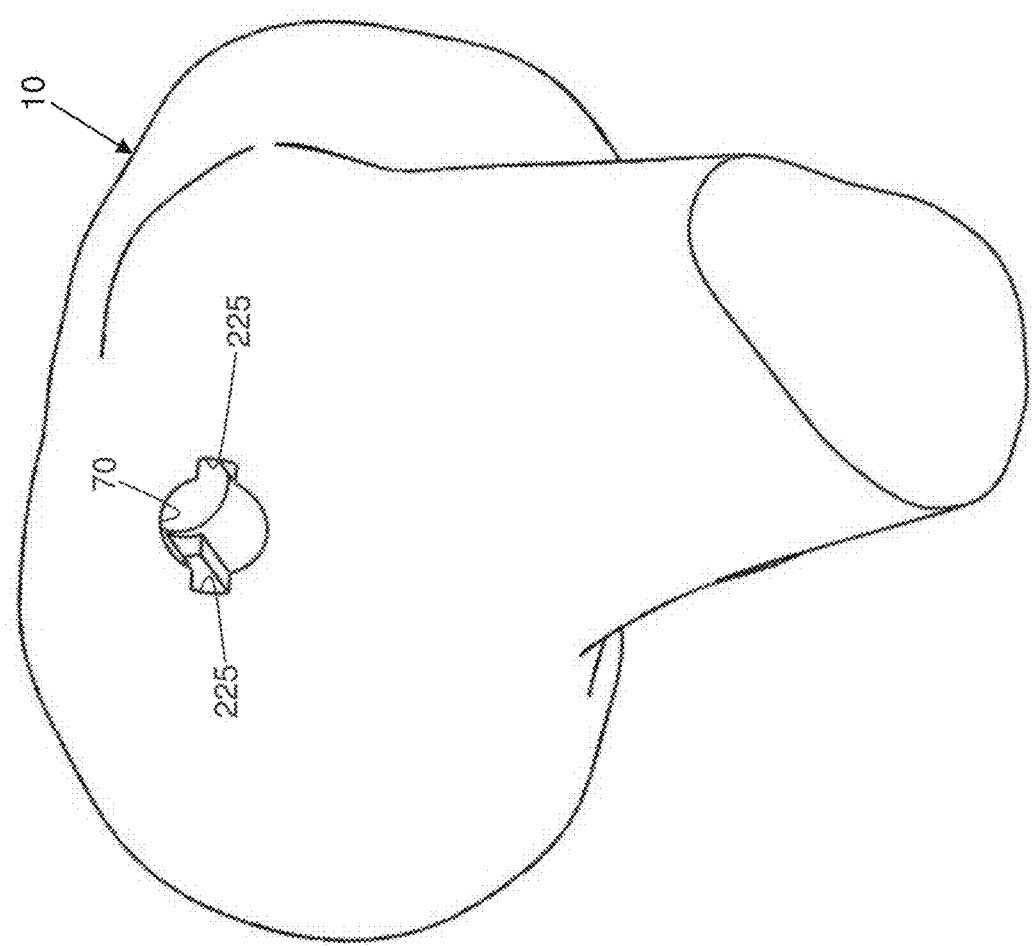

The notched tibial tunnel (i.e., the tibial tunnel 70 with diametrically-opposed notches 225) is shown in FIG. 36.

Graft Insertion

After tibial tunnel 70 has been notched (i.e., by forming diametrically-opposed notches 225 along tibial tunnel 70) and after femoral tunnel 80 has been notched (i.e., by forming diametrically-opposed notches 185 along femoral tunnel 80), graft 90 is inserted through tibial tunnel 70 and into femoral tunnel 80.

1. First Approach for Graft Insertion

Figure 2:
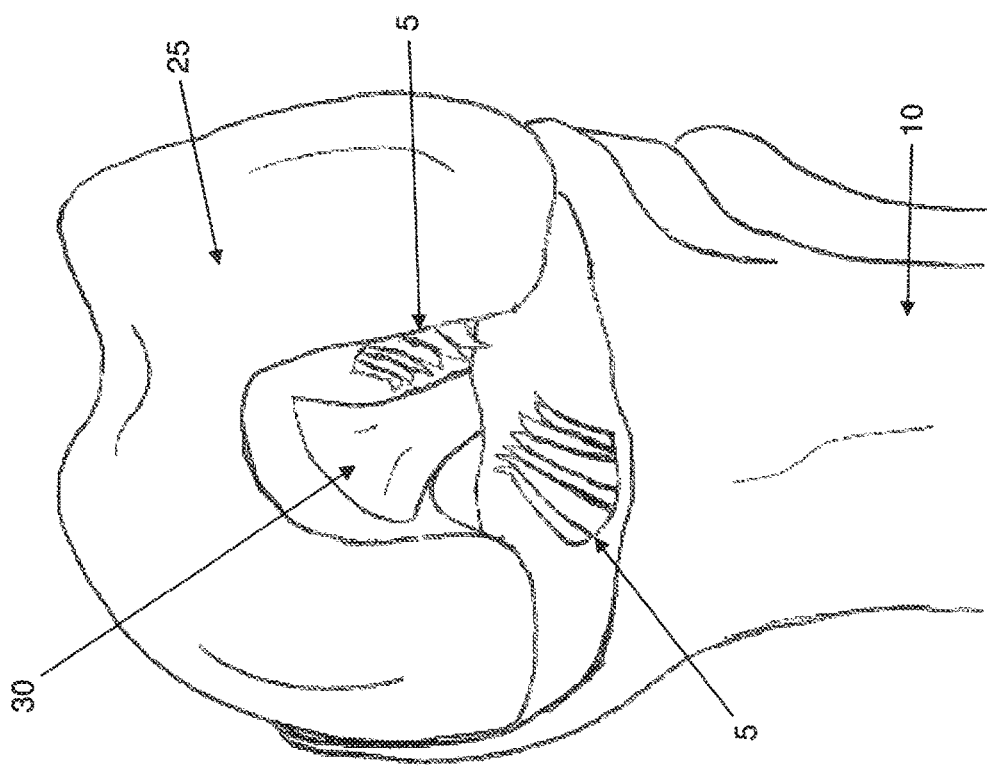
FIG. 2 is a schematic view showing the interior of a knee joint, including a damaged or injured ACL.
Figure 1:
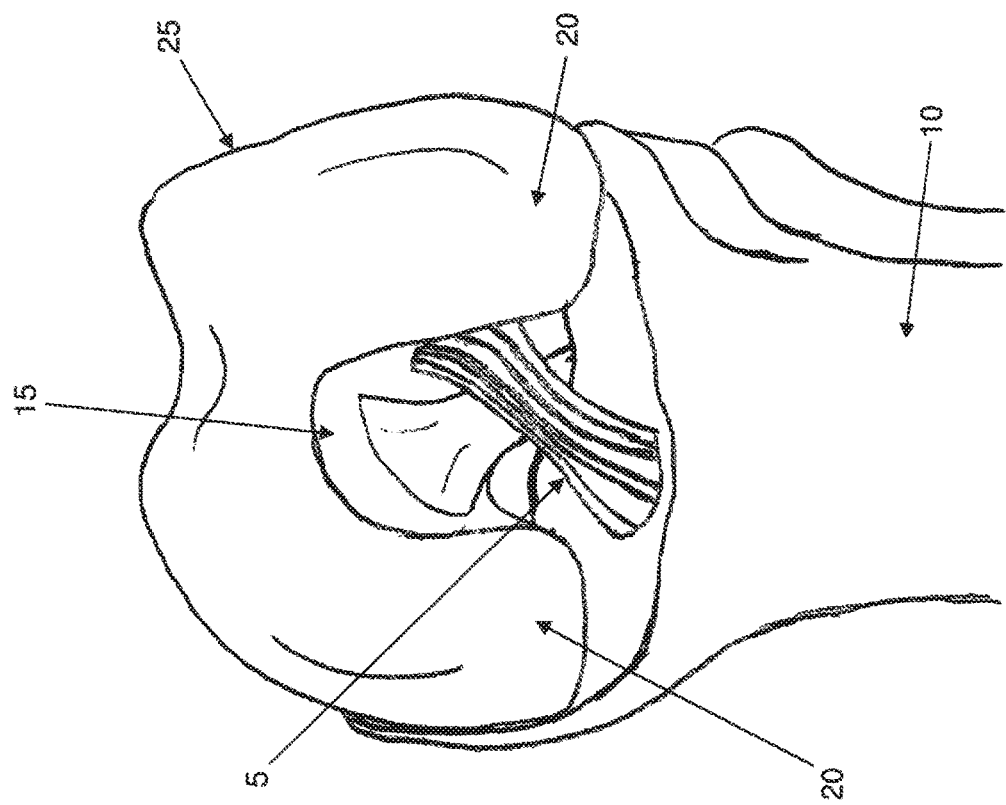
FIG. 1 is a schematic view showing the interior of a knee joint, including the native ACL.
Figure 4:
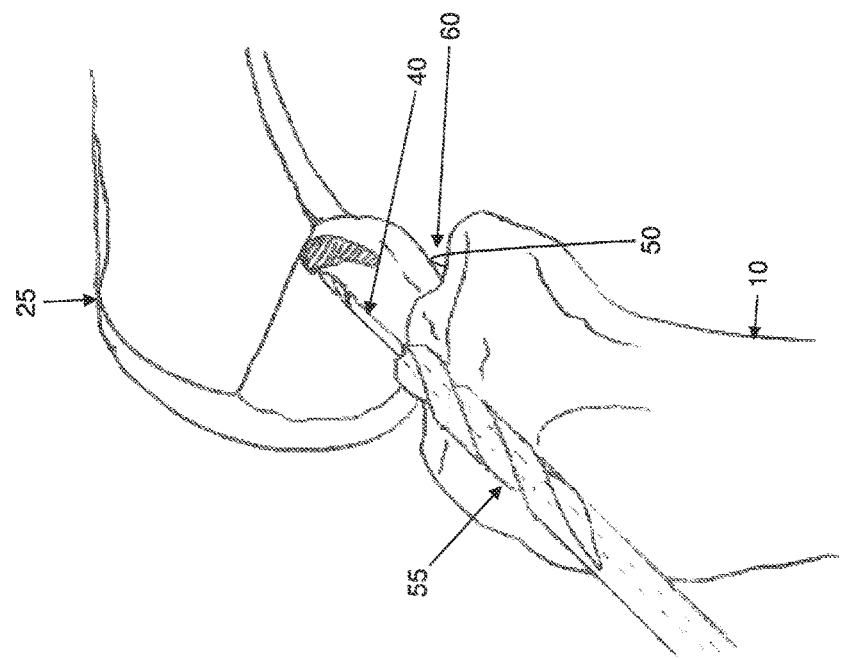
FIGS. 3-8 are schematic views showing bone tunnels being formed in the tibia and femur, and a graft being inserted into the bone tunnels.
Figure 3:
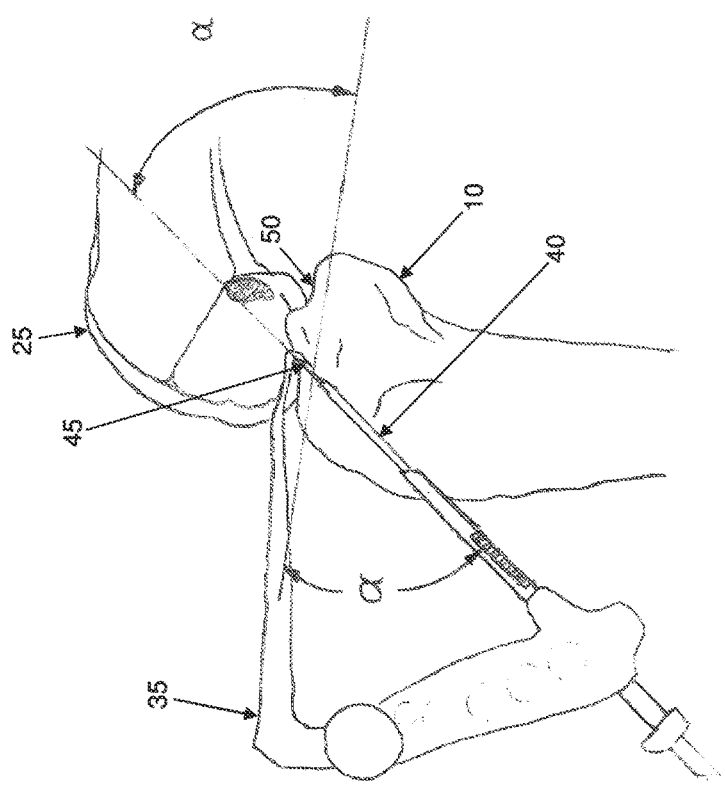
Figure 5:
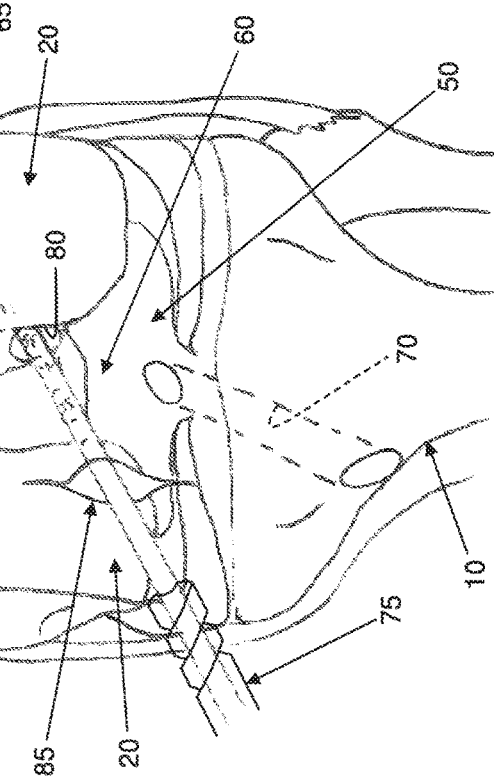
Figure 6:
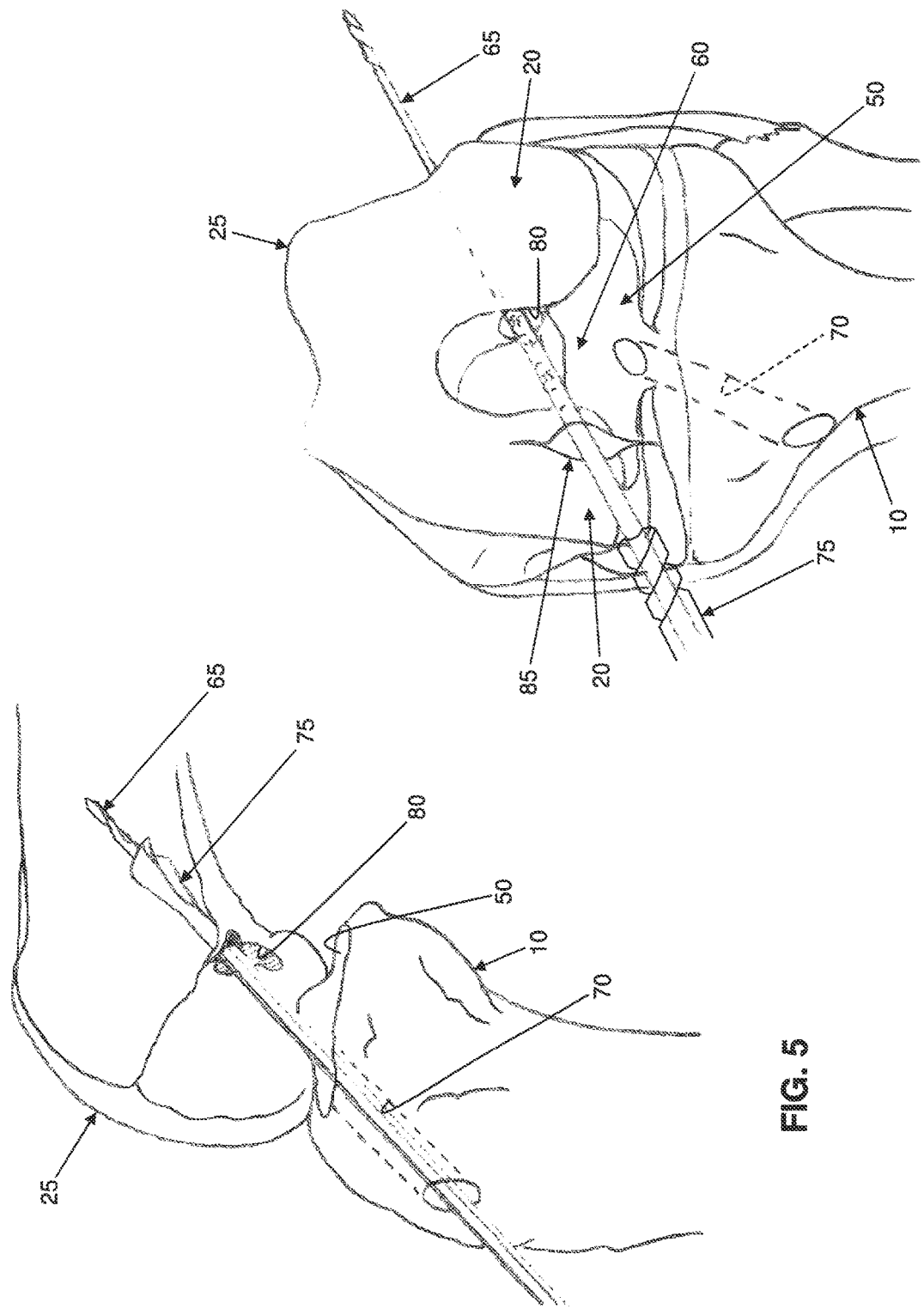
Figure 7:
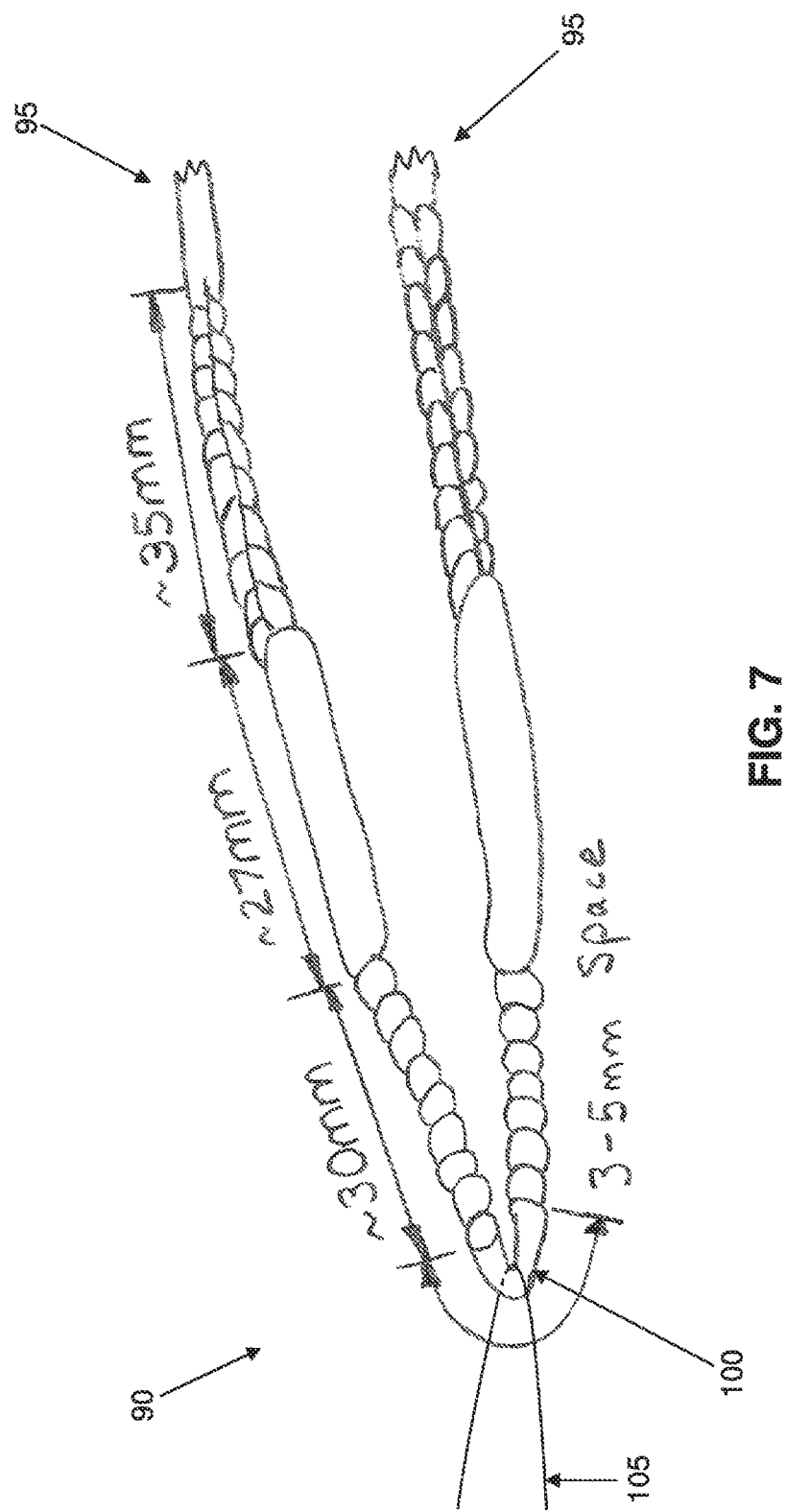
Figure 9:
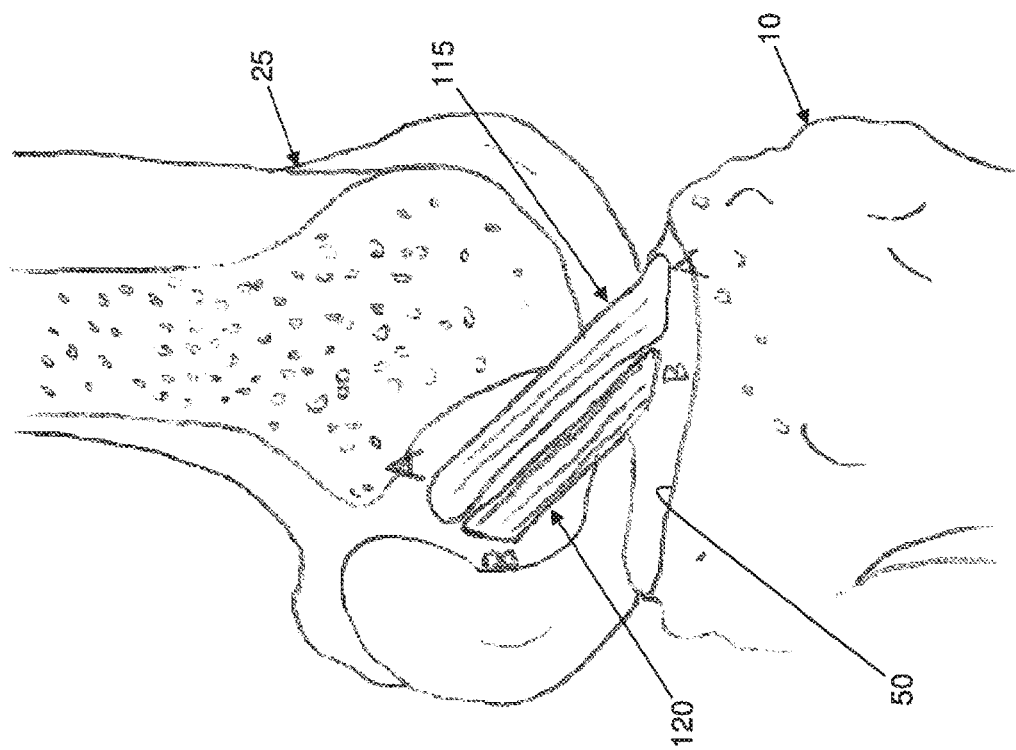
FIGS. 9 and 10 are schematic views showing details of the construction and biomechanics of the ACL as the knee moves from extension to flexion.
Figure 8:
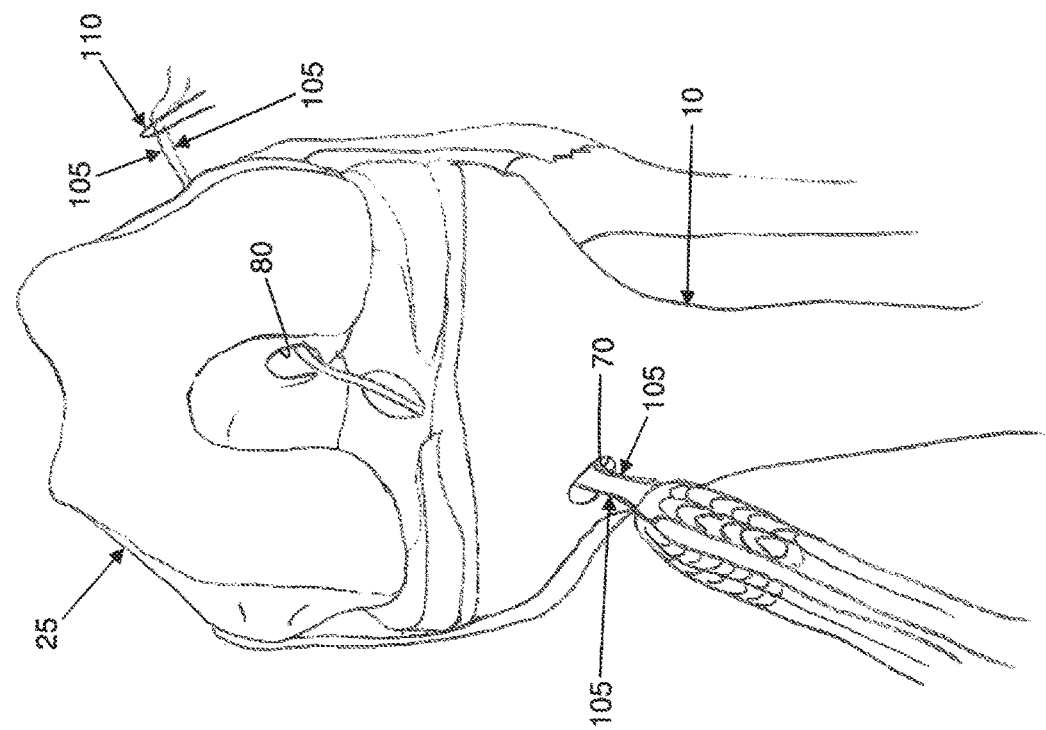
Figure 11:
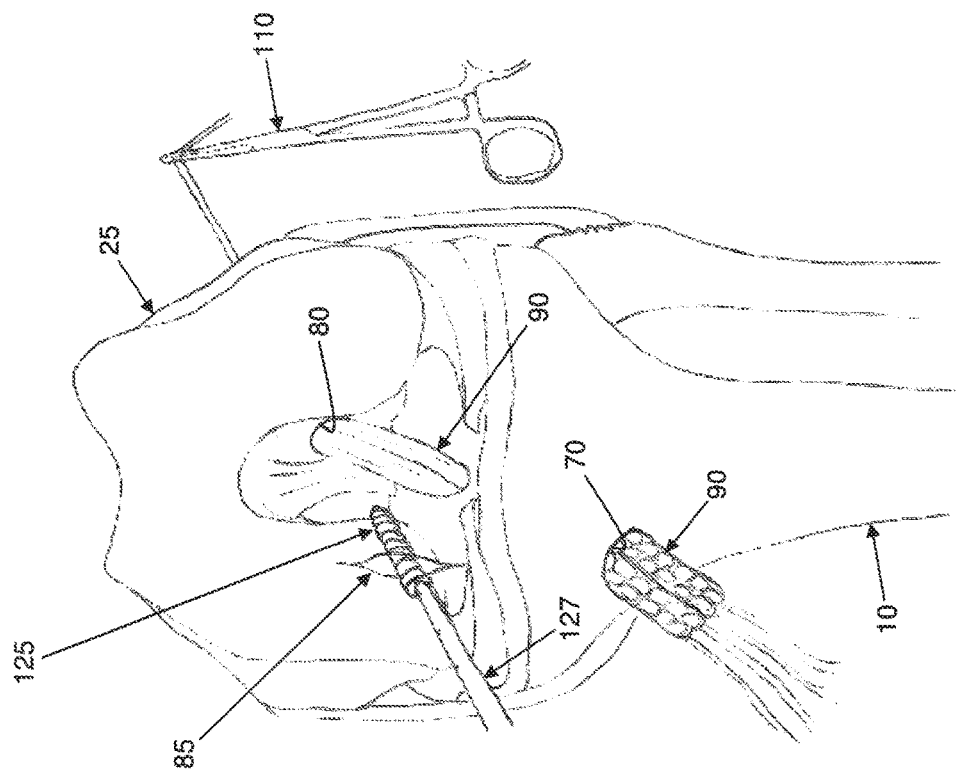
FIGS. 11-13 are schematic views showing a graft being secured in femoral and tibial tunnels using interference screws.
Figure 10:
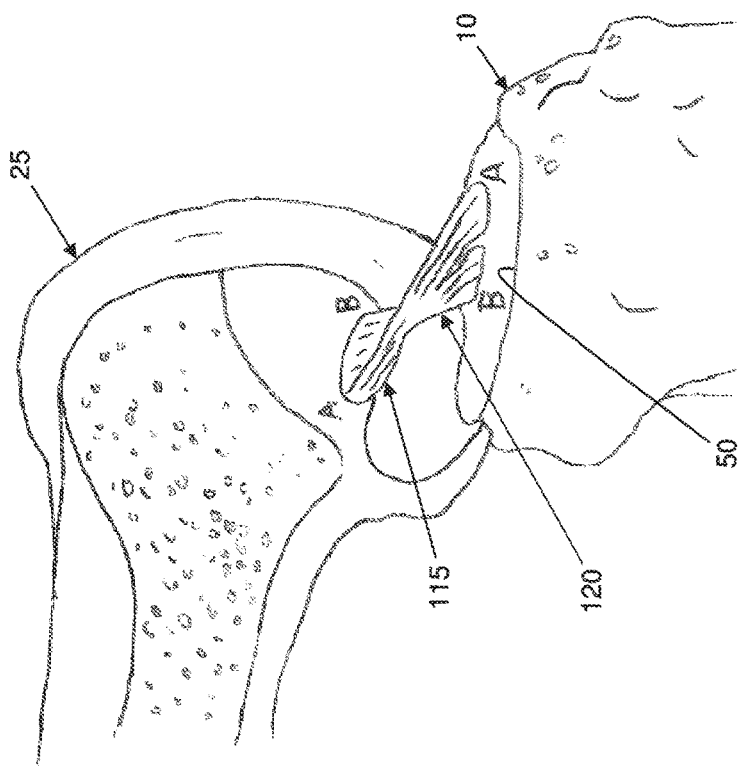
Figure 13:
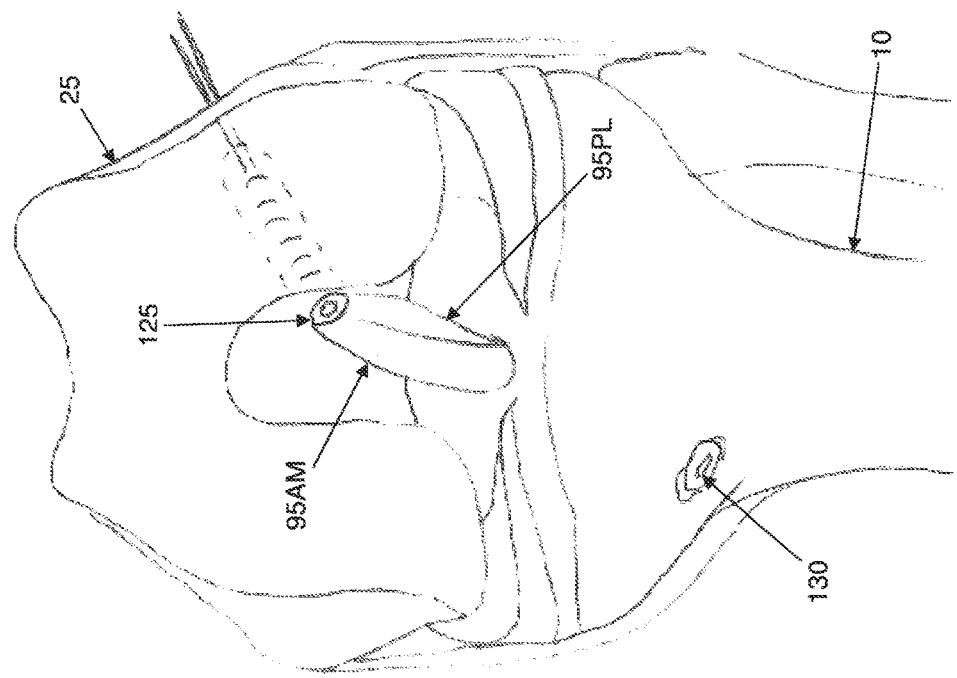
Figure 12:
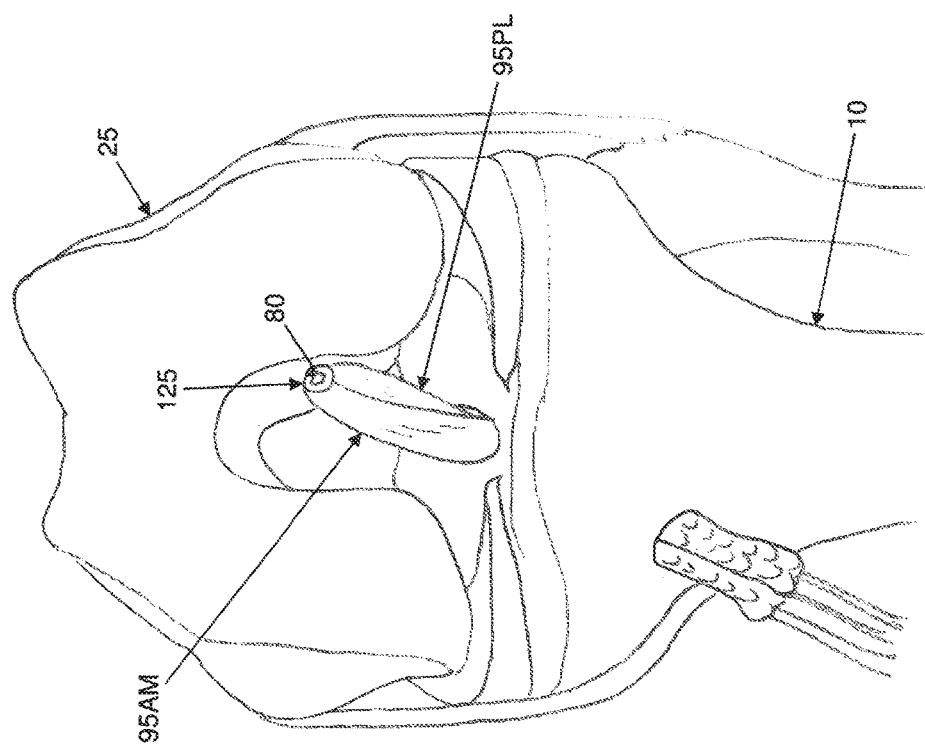
Figure 15:
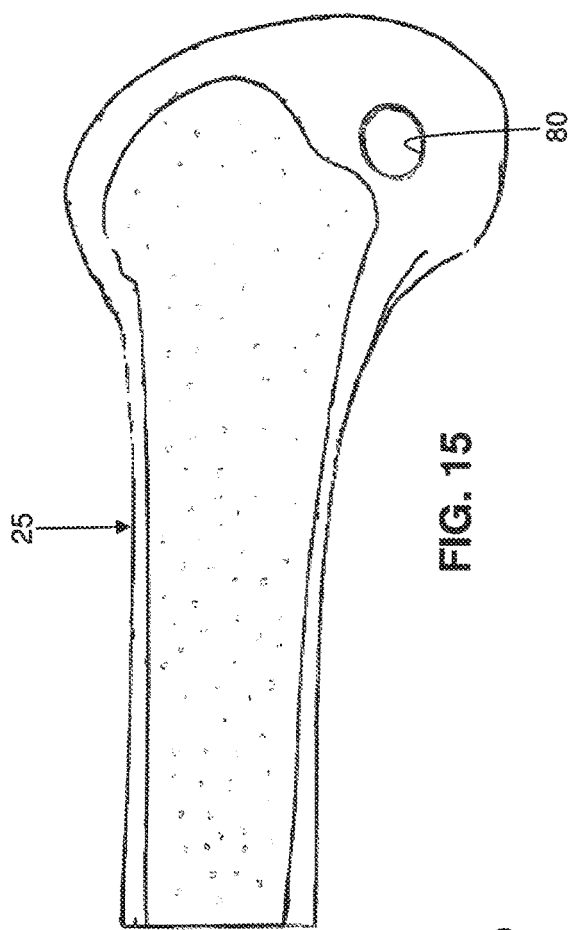
FIG. 15 is a schematic view showing how a femoral tunnel typically has an elliptical configuration at the joint-side mouth of the femoral tunnel.
Figure 14:
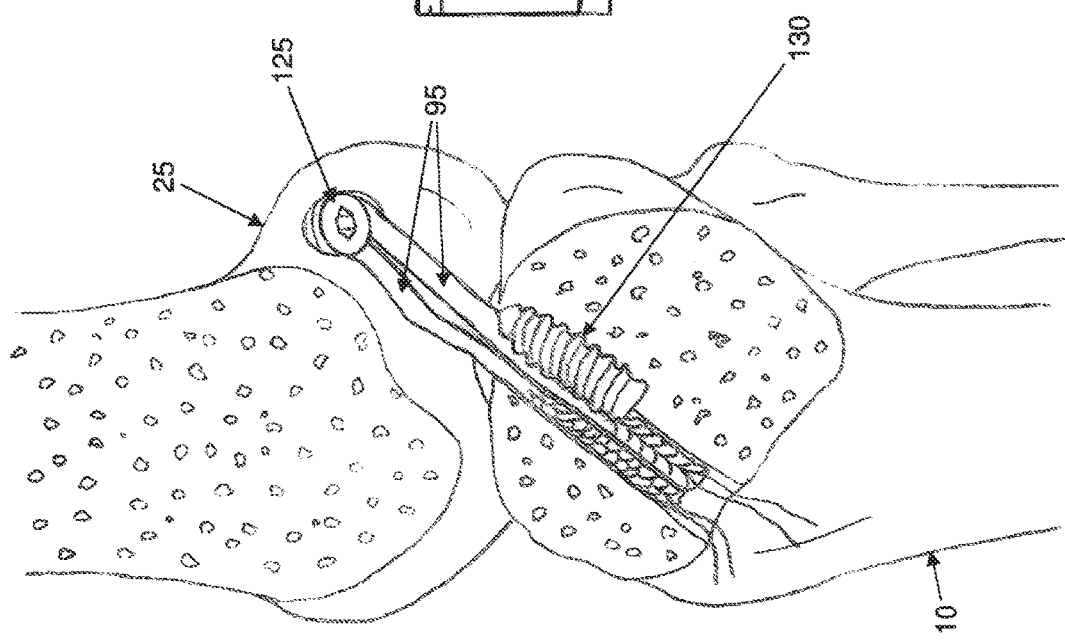
FIG. 14 is a schematic view showing how a graft may be secured off-center within a bone tunnel when using a conventional interference screw.
Figure 16:
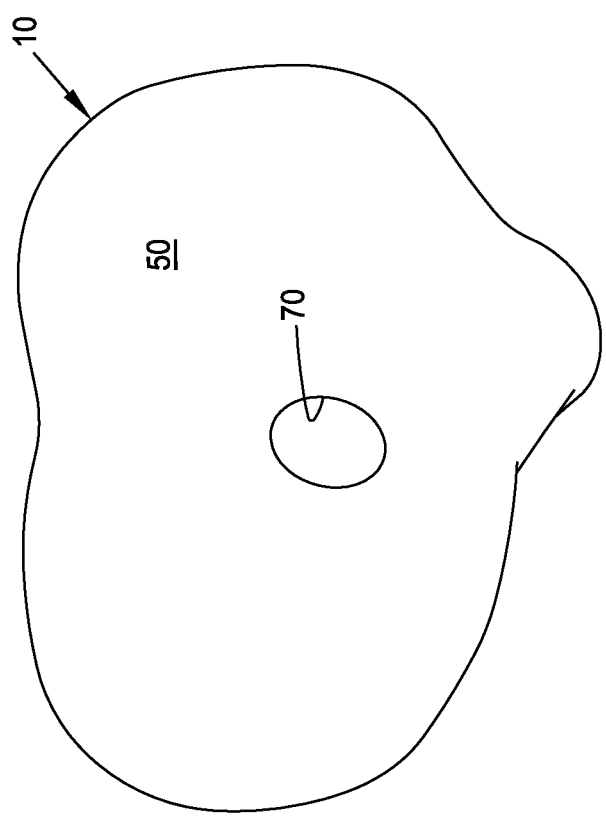
FIG. 16 is a schematic view showing how a tibial tunnel typically has an elliptical configuration at the joint-side mouth of the tibial tunnel.
Figure 17:
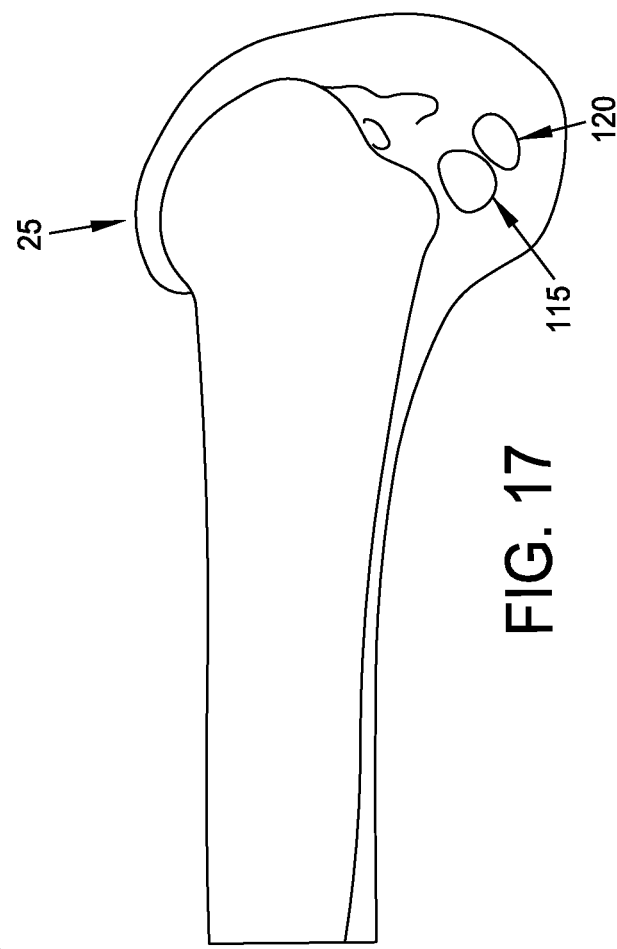
FIG. 17 is a schematic view showing the natural insertion of the ACL on the femur.
Figure 21:
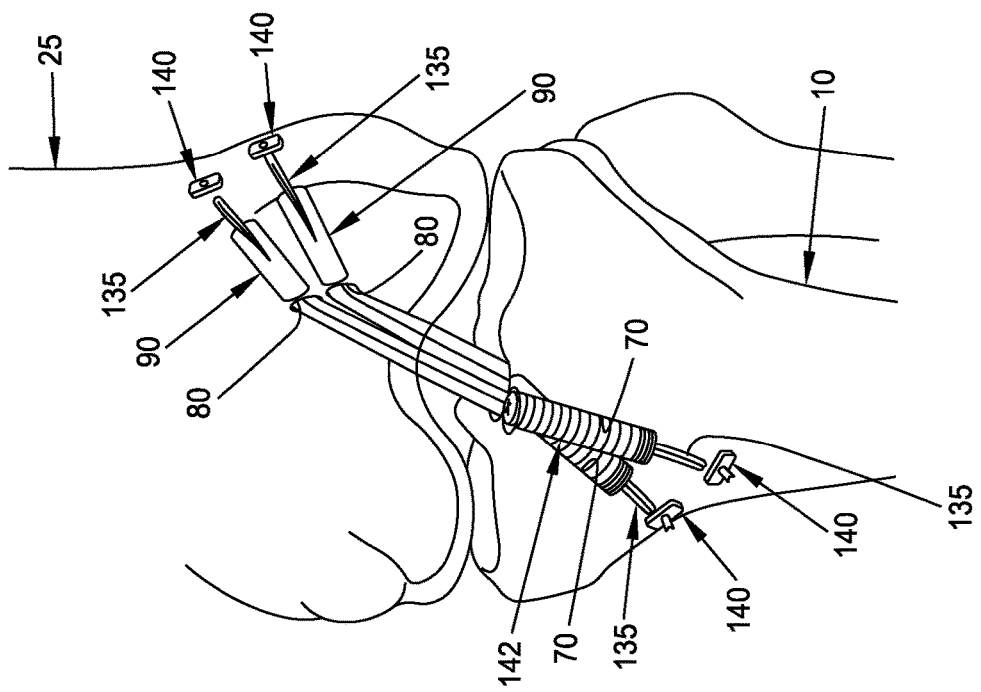
FIG. 21 is a schematic view showing a suspensory fixation of a graft in femoral and tibial tunnels.
Figure 20:
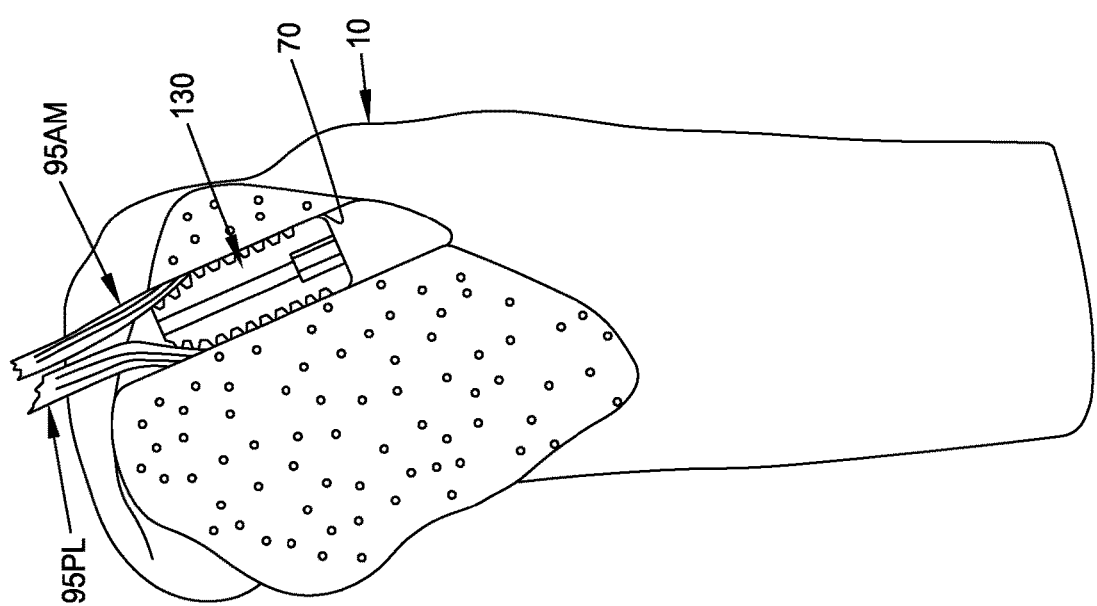
FIG. 20 is a schematic view showing how fixation of a graft in a tibial tunnel with an interference screw may lead to the so-called "windshield wiper effect"

In a manner that is similar to the approach described above, graft 90 is folded over such that two graft bundles 95 comprise the aggregate graft 90, and graft tow sutures 105 are looped around graft 90 at folded section 100 (i.e., where the graft is folded over). See FIG. 7.

Next, a guide pin (not shown), having an eyelet (not shown) for passing sutures, is inserted through medial portal skin incision 85, through joint space 60 and through femoral tunnel 80. The suture-carrying guide pin exits through the skin opposite the distal end of femoral tunnel 80. The passing sutures carried through the femoral tunnel are then grasped (with a hemostat) and the guide pin is withdrawn. Then graspers (not shown) are inserted through tibial tunnel 70, into joint space 60 and used to grasp the passing sutures emerging on the joint side of femoral tunnel 80. These graspers are then used to pull the passing suture emerging from the joint side of femoral tunnel 80 across joint space 60 and down through tibial tunnel 70 until the passing sutures emerge on the anteromedial side of tibia 10. At this point, these passing sutures extend from the anteromedial side of tibia 10, up through tibial tunnel 70, across joint space 60, through femoral tunnel 80 and exits through the skin opposite the distal end of femoral tunnel 80.

These passing sutures are then used to tow graft 90 through tibial tunnel 70, through joint space 60 and into femoral tunnel 80, i.e., by tying graft tow sutures 105 to the passing sutures emerging from tibial tunnel 70, and then pulling on the passing sutures emerging from femoral tunnel 80.

In order to ensure that graft bundles 95 of graft 90 are disposed in their anatomically correct locations within tibial tunnel 70 and femoral tunnel 80, a tibial graft separator 230 (FIGS. 37 and 38) and a femoral graft separator 235 (FIGS. 37 and 39) are used.

Figure 37:
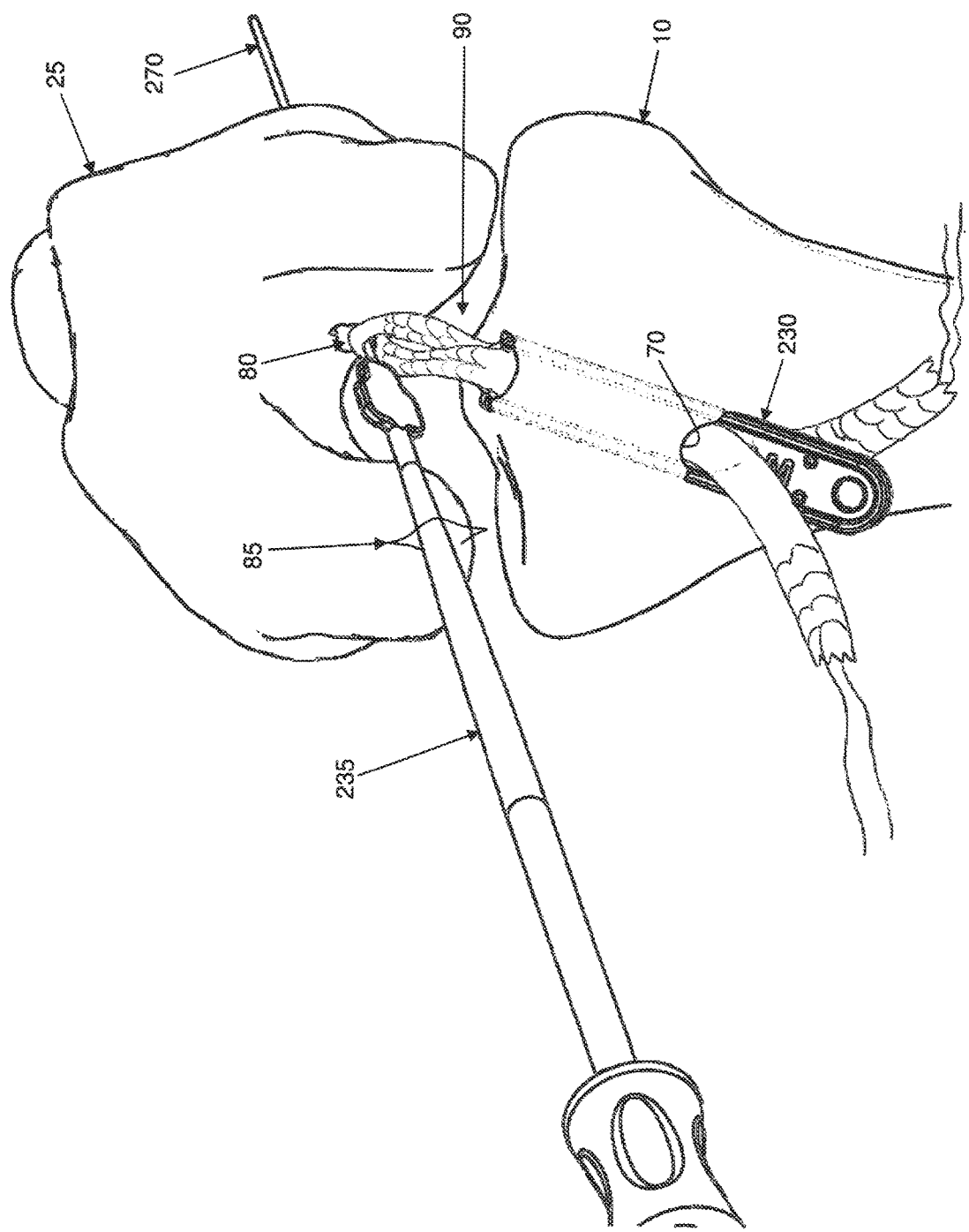
FIGS. 37-40 are schematic views showing a graft being inserted into tibial and femoral tunnels using a tibial graft separator and a femoral graft separator.
Figure 38:
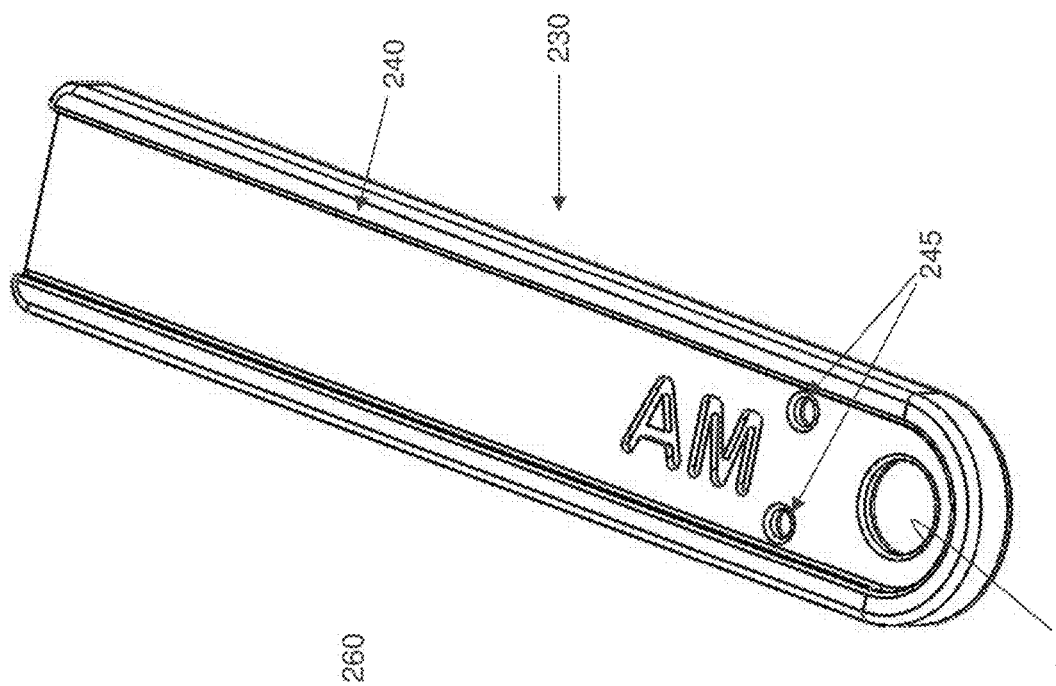

As seen in FIGS. 37 and 38, tibial graft separator 230 is provided for aligning graft bundles 95 relative to tibial tunnel 70. More particularly, tibial graft separator 230 comprises a rim 240 extending around the perimeter of tibial graft separator 230. Tibial graft separator 230 is sized to fit into notches 225 formed in tibial tunnel 70, with the tibial graft separator bifurcating tibial tunnel 70 into two passageways. The portion of tibial graft separator 230 which extends between rims 240 is thinner, providing spaces for allowing graft bundles 95 of graft 90 to pass through tibial tunnel 70 (the graft bundle 95AM being located on one side of the tibial graft separator and the graft bundle 95PL being located on the other side of the tibial graft separator). If desired, tibial graft separator 230 may include a label (e.g., "AM") on one side of tibial graft separator 230 in order to remind the surgeon of the AM bundle side, and tibial graft separator 230 may include another label (e.g., "PL") on the other side of tibial graft separator 230 in order to remind the surgeon of the PL bundle side. In one preferred form of the present invention, tibial graft separator 230 comprises two small holes 245 for allowing temporary suture fixation of the graft 90 to tibial graft separator 230 (if necessary), and a larger hole 250 to aid in removing tibial graft separator 230 from tibial tunnel 70 (if necessary).

Figure 39:
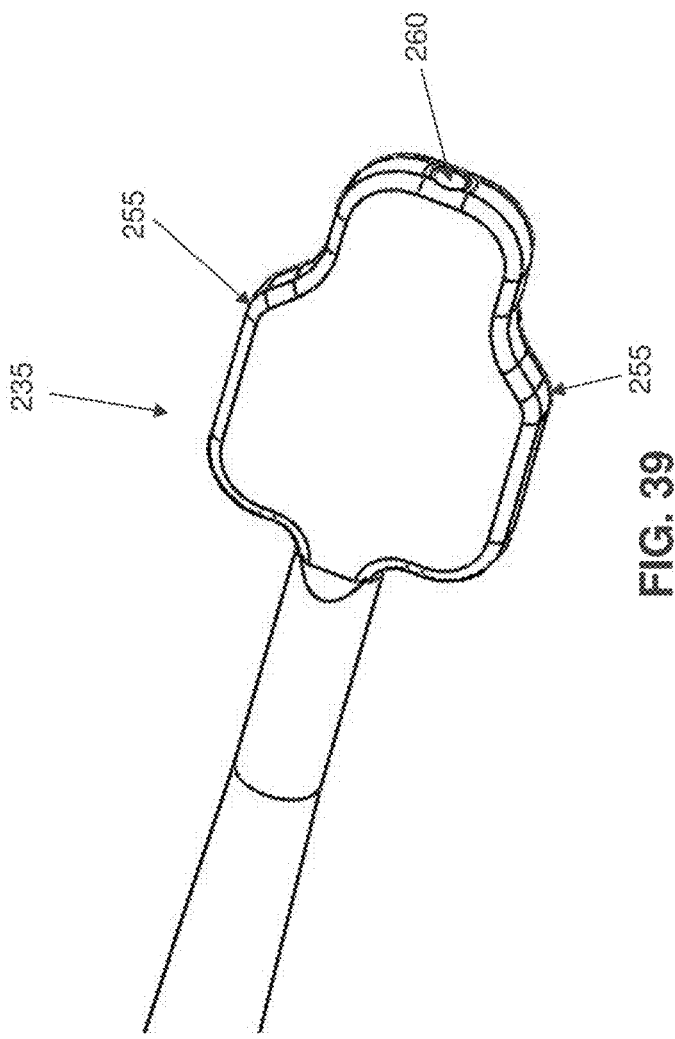

As seen in FIGS. 37 and 39, femoral graft separator 235 preferably comprises side protrusions 255 for tracking femoral graft separator 235 within notches 185 of femoral tunnel 80, such that the femoral graft separator can bifurcate femoral tunnel 80 into two passageways. In one preferred form of the present invention, femoral graft separator 235 is cannulated with a central bore 260, whereby to permit passing femoral graft separator 235 over a guide wire if desired.

Looking now at FIG. 37, after passing sutures have been extended from the anteromedial side of tibia 10, through tibial tunnel 70, across joint space 60 and through femoral tunnel 80, tibial graft separator 230 is introduced between graft bundles 95, and aligned with notches 225 of tibial tunnel 70. Tibial graft separator 230 is placed between graft bundles 95 so that one of the graft bundles, 95AM, is in the position of the natural AM bundle and the other of the graft bundles, 95PL, is in the position of the natural PL bundle, with the sides of tibial graft separator 230 aligned with tibial tunnel notches 225. Then, using the passing sutures secured to graft tow sutures 105, and advancing tibial graft separator 230 in conjunction with graft 90, graft 90 is pulled into tibial tunnel 70. It will be appreciated that as graft 90 is pulled up through tibial tunnel 70, the advancing tibial graft separator 230 will act as a tunnel bifurcator, ensuring that graft bundle 95AM is in the position of the natural AM bundle and the graft bundle 95PL is in the position of the natural PL bundle.

Figure 40:
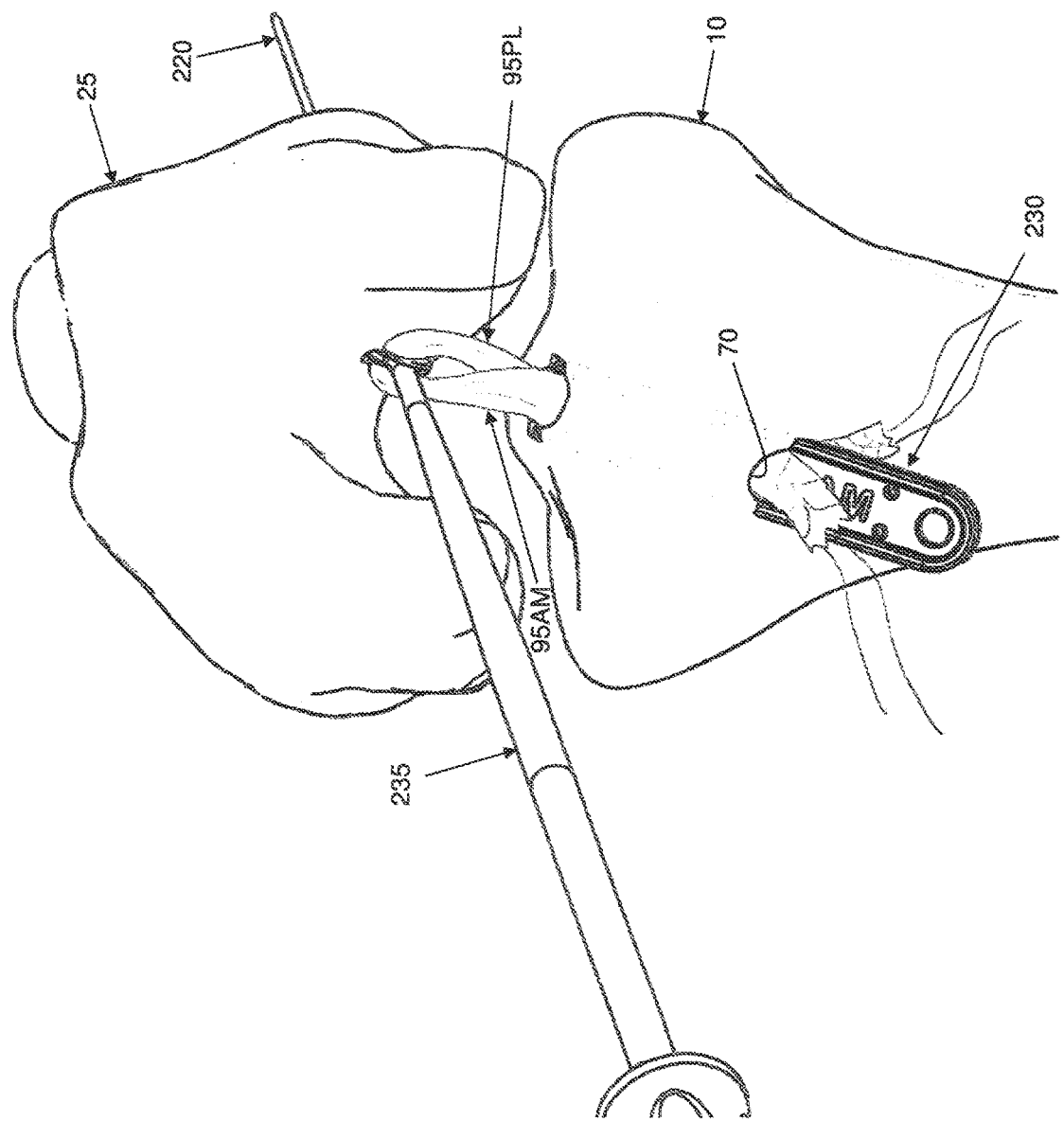

Still looking now at FIG. 37, after the distal end of graft 90 has been drawn up through tibial tunnel 70 and into joint space 60, a femoral guide wire 270 (approximately 1 mm to 1.3 mm in diameter) is passed through the loop 100 of graft 90. AM and PL graft bundles 95AM, 95PL are then manipulated into their approximate native anatomic locations at the mouth of femoral tunnel 80. Next, femoral graft separator 235 is advanced over femoral guide wire 270 so as to engage graft bundles 95AM, 95PL. Femoral graft separator 235 is then used to manipulate and push graft 90 into femoral tunnel 80. See FIG. 40. As graft 90 is pushed into femoral tunnel 80, femoral graft separator 235 keeps the AM and PL bundles 95AM, 95PL aligned and in their desired anatomic positions. The passing sutures and graft tow sutures 105 are then used to pull graft 90 up into femoral tunnel 80, i.e., by pulling on the passing sutures emerging from the distal end of femoral tunnel 80.

As a result of the foregoing, graft 90 will extend through tibial tunnel 70, across joint space 60 and into femoral tunnel 80, with the AM and PL bundles 95AM, 95PL aligned and in their desired anatomic positions.

2. Second Approach for Graft Insertion

Figure 41:
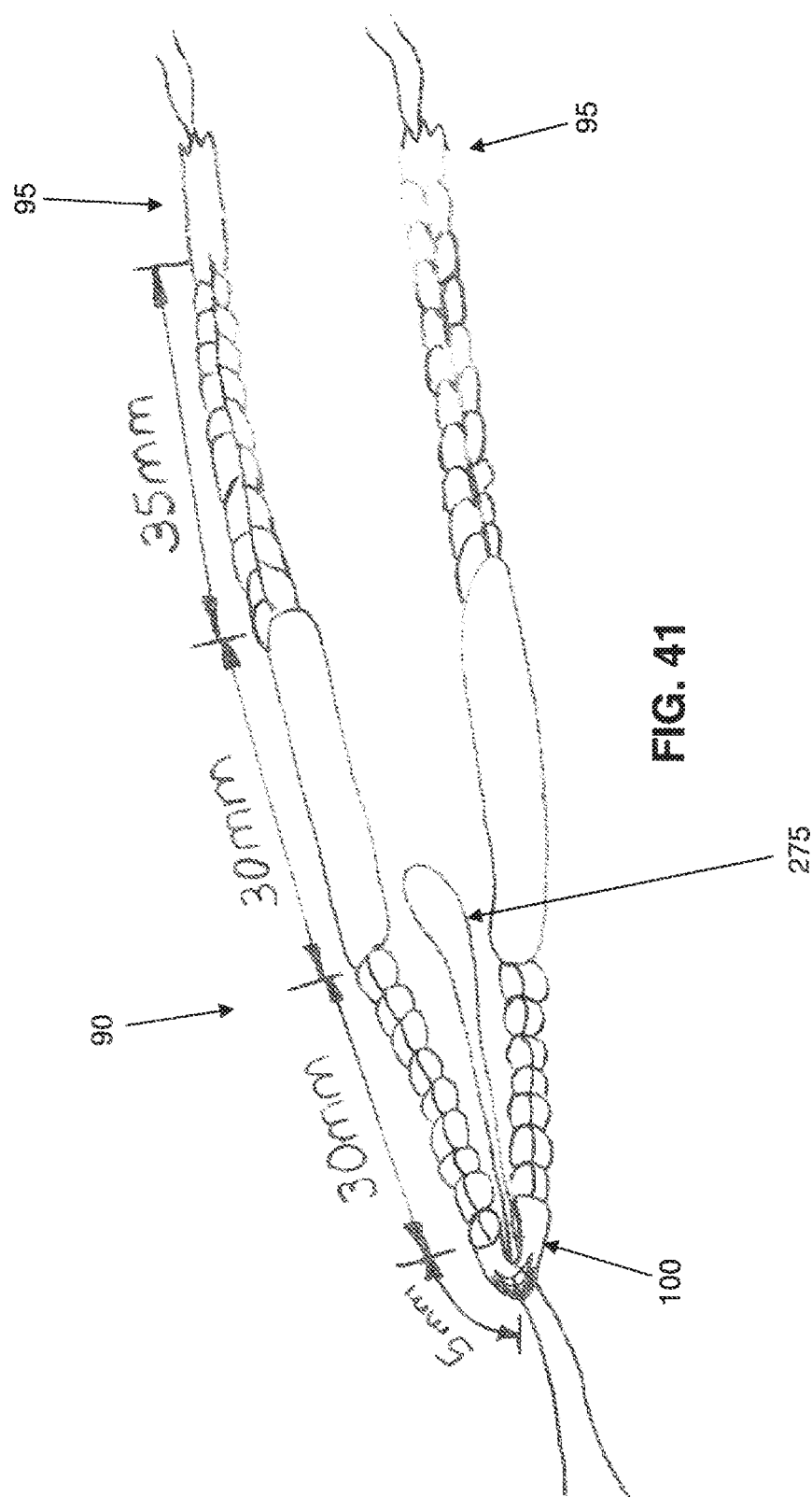
FIG. 41 is a schematic view showing an alternative approach for preparing a graft.

In an alternative approach, and looking now at FIG. 41, the soft tissue graft 90 is prepared differently than previously described. Cadaveric evaluations and engineering tests have indicated this alternative method to be the preferred method of graft preparation when utilizing the new fixation device and technique. The folded-over length of graft 90 should measure 5 mm on each side of the fold (10 mm between the central whipstitched sections, when graft 90 is laid out end-to-end). Graft 90 is whipstitched with one color suture on one leg (i.e., one bundle 95) of the graft, and a second color suture on the other leg (i.e., the other bundle 95) of the graft. An additional suture, an anatomic guide wire passing suture 275, is passed through the loop 100 of graft 90, or pushed through the midsubstance of the graft via blunt dissection.

Figure 42:
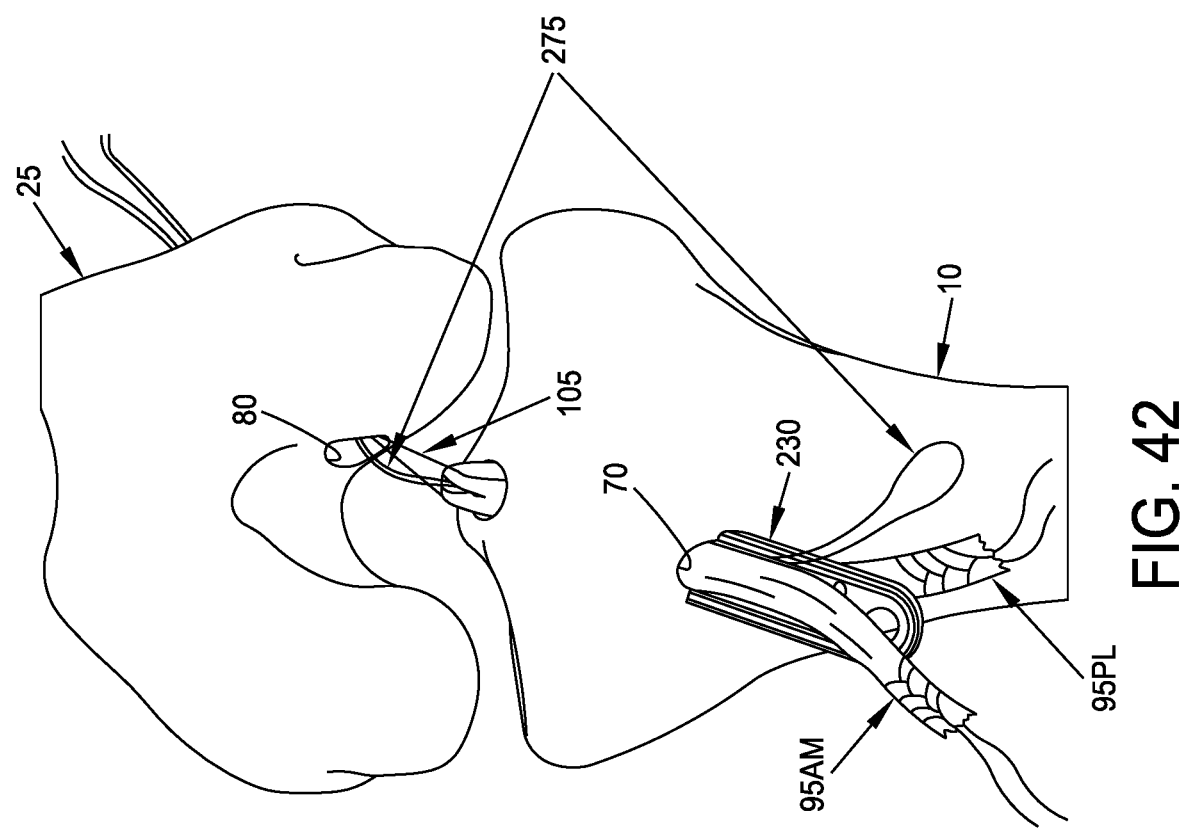

In this form of the invention, and looking now at FIG. 42, graft 90 is towed into the tibial tunnel and then into the femoral tunnel, preferably by first positioning passing sutures from the anteromedial side of tibia 10, up through tibial tunnel 70, across joint space 60, through femoral tunnel 80 and out the skin opposite the distal end of femoral tunnel 80 in the manner previously described, attaching the graft tow sutures 105 to the passing sutures, and then pulling on the passing sutures emerging from the distal end of femoral tunnel 80 to draw graft 90 up into tibial tunnel 70 and across joint space 60 until the graft just enters the joint space. See FIG. 42. Again, tibial graft separator 230 is inserted into tibial tunnel 70 along with graft 90, separating the AM and PL bundles 95AM, 95PL from one another as they extend through tibial tunnel 70. The anatomic guide wire passing suture 275 is kept easily accessible near the lateral side of the graft. The AM bundle 95AM should be "on top of" tibial graft separator 230 and the PL bundle 95PL should be "on the underside of" tibial graft separator 230.

Figure 43:
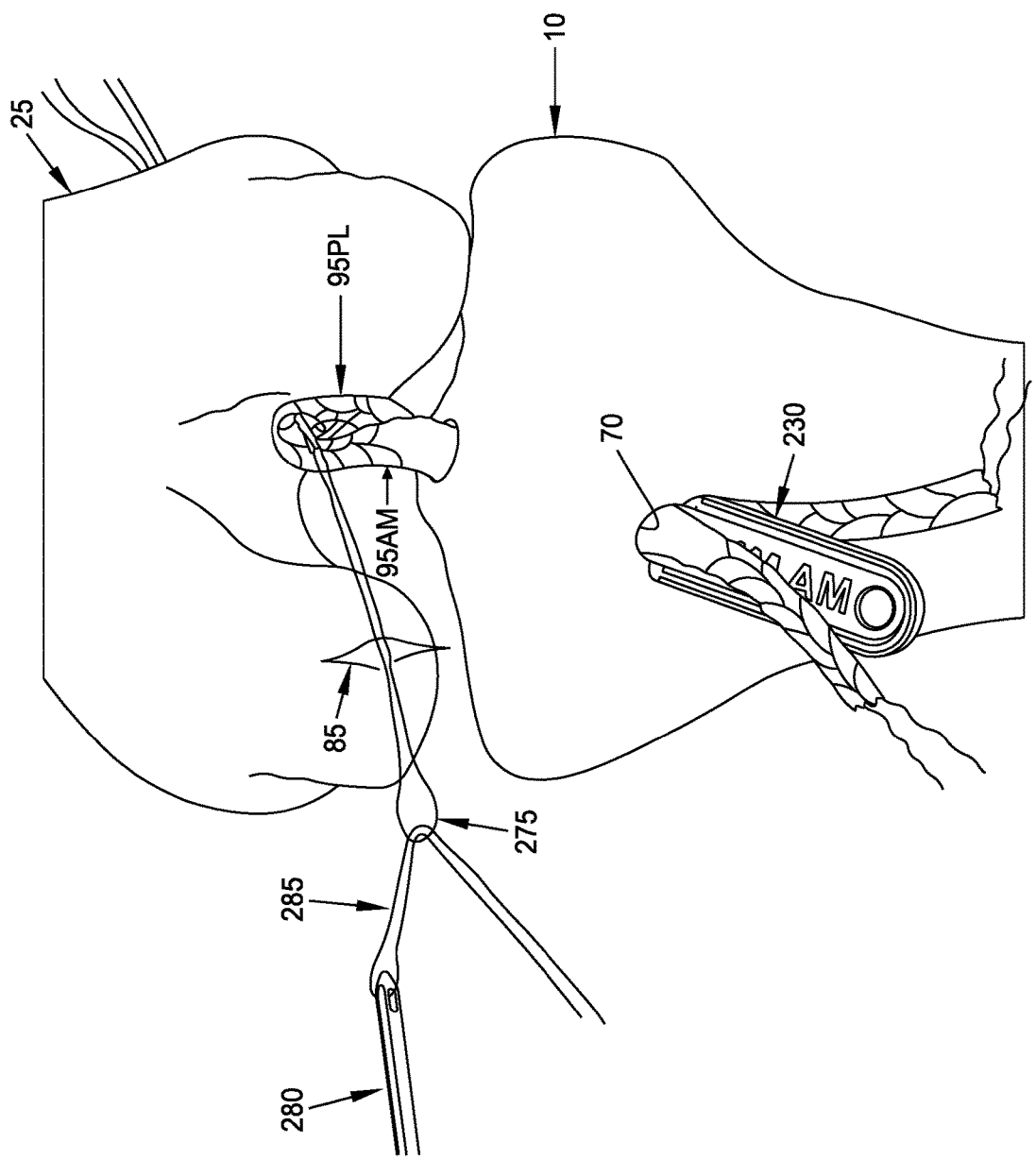
Figure 43A:
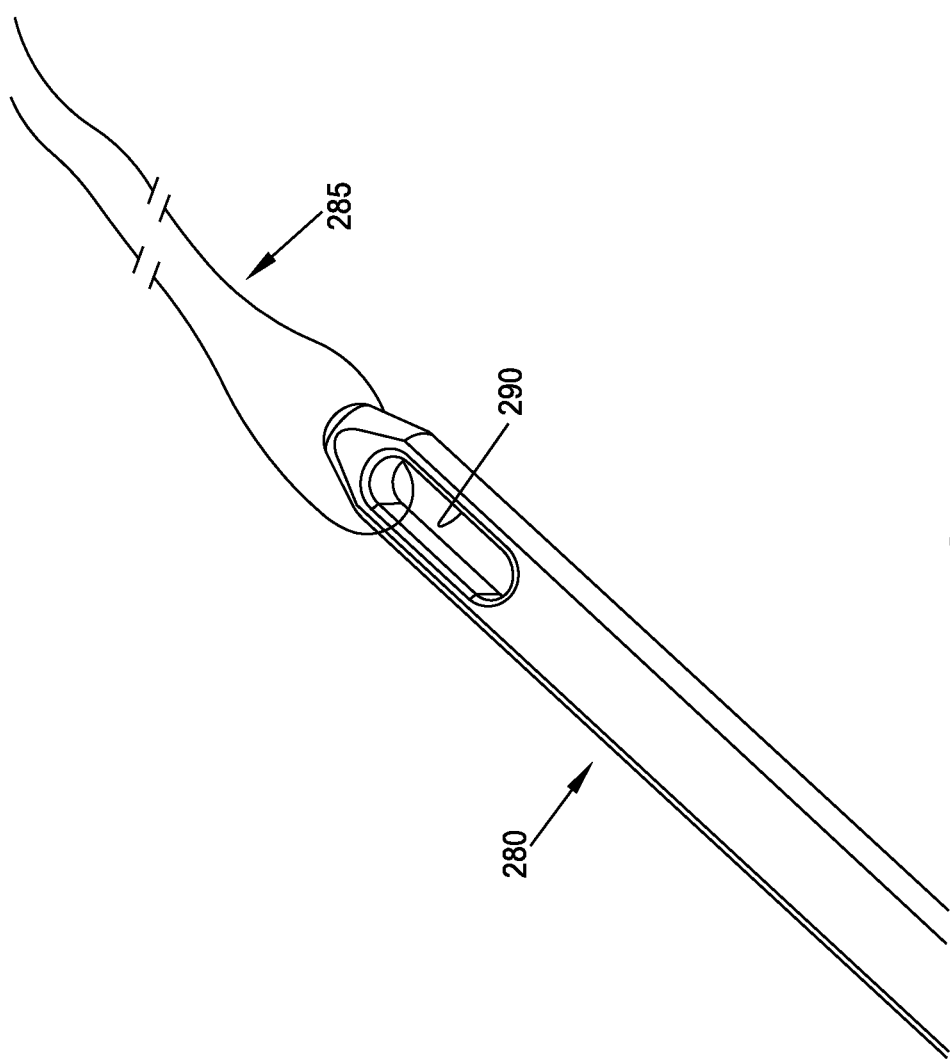
Figure 44:
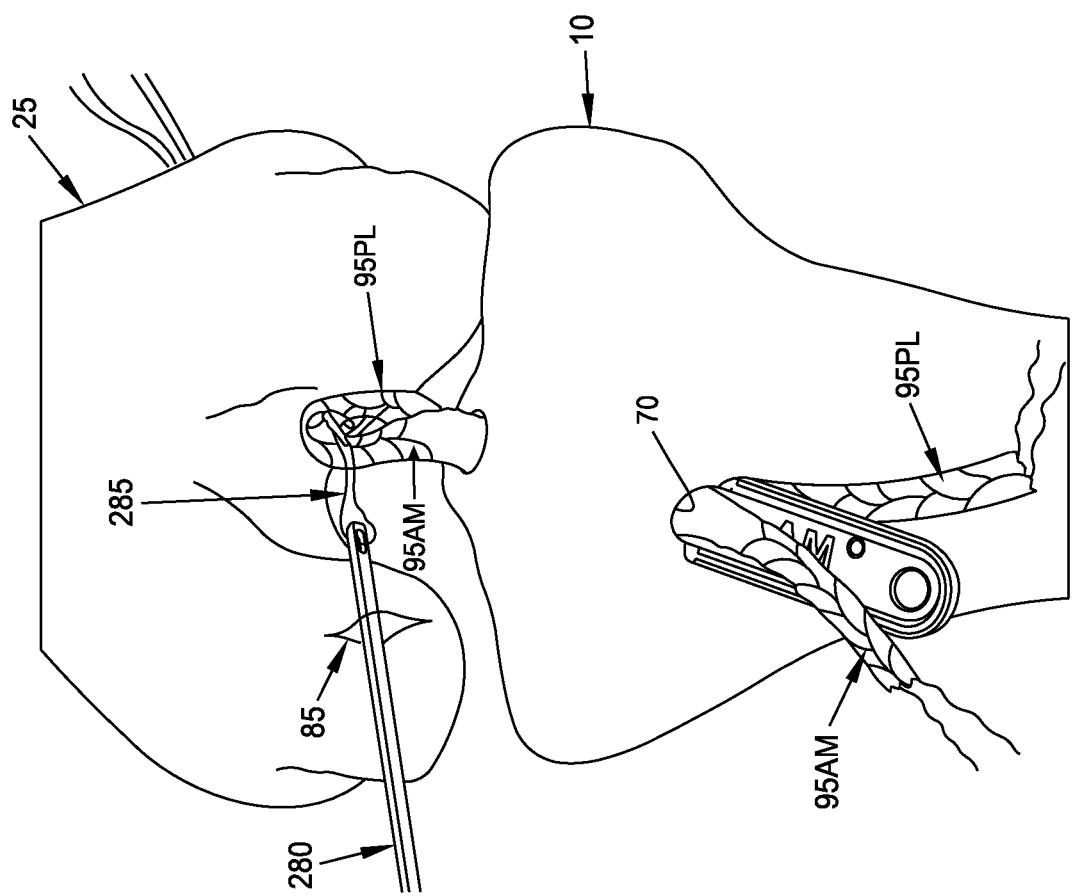

The passing sutures and/or graft tow sutures 105 are then further pulled so as to advance graft 90 to the mouth of femoral tunnel 80. See FIG. 43. With the knee in 90° of flexion, as is the typical surgical position, AM bundle 95AM is positioned near the posterior portion of femoral tunnel 80. The PL bundle 95PL is positioned near the anterior portion of femoral tunnel 80. Guide wire passing suture 275 is then used to pull a femoral guide wire 280 through the loop 100 in graft 90 (i.e., between the AM bundle 95AM and the PL bundle 95PL), or through the midsubstance of both graft bundles 95AM, 95PL together, and then through femoral tunnel 80. More particularly, and as seen in FIGS. 43, 43A and 44, this is preferably done by advancing forceps (not shown) through medial portal skin incision 85; picking up guide wire passing suture 275 with the forceps; pulling guide wire passing suture 275 out medial portal skin incision 85; engaging a guide wire suture 285 (which is threaded through the eyelet 290 of femoral guide wire 280); drawing guide wire suture 285 back through medial portal skin incision 85, across joint space 60, and through femoral tunnel 80; and then using guide wire suture 285 to pull femoral guide wire 280 through medial portal skin incision 85, across joint space 60, through the loop 100 in graft 90 (i.e., between the AM bundle 95AM and the PL bundle 95PL) and through femoral tunnel 80. Note that guide wire suture 285 and femoral guide wire 280 are positioned such that they are in front of (i.e., anterior to) the AM bundle 95AM to aid in the anatomic arrangement of the graft bundles. Note also that as the graft 90 is pulled into position, tibial graft separator 230 keeps the graft bundles 95AM, 95PL aligned in their respective AM and PL positions.

As seen in FIG. 43A, femoral guide wire 280 is rounded at its distal tip to prevent damage to the graft bundles 95AM, 95PL, but generally tapered to allow ease of passage through the graft bundles and the femoral tunnel. Femoral guide wire 280 is preferably flat on both sides (i.e., it has a generally rectangular cross-section with rounded sides) for later use during the insertion of the femoral fixation device and, if desired, the tibial fixation device (see below). Eyelet 290 is on the leading tip of femoral guide wire 280 to allow it to accept guide wire suture 285, which is used to pull femoral guide wire 280 into femoral tunnel 80.

Figure 47:
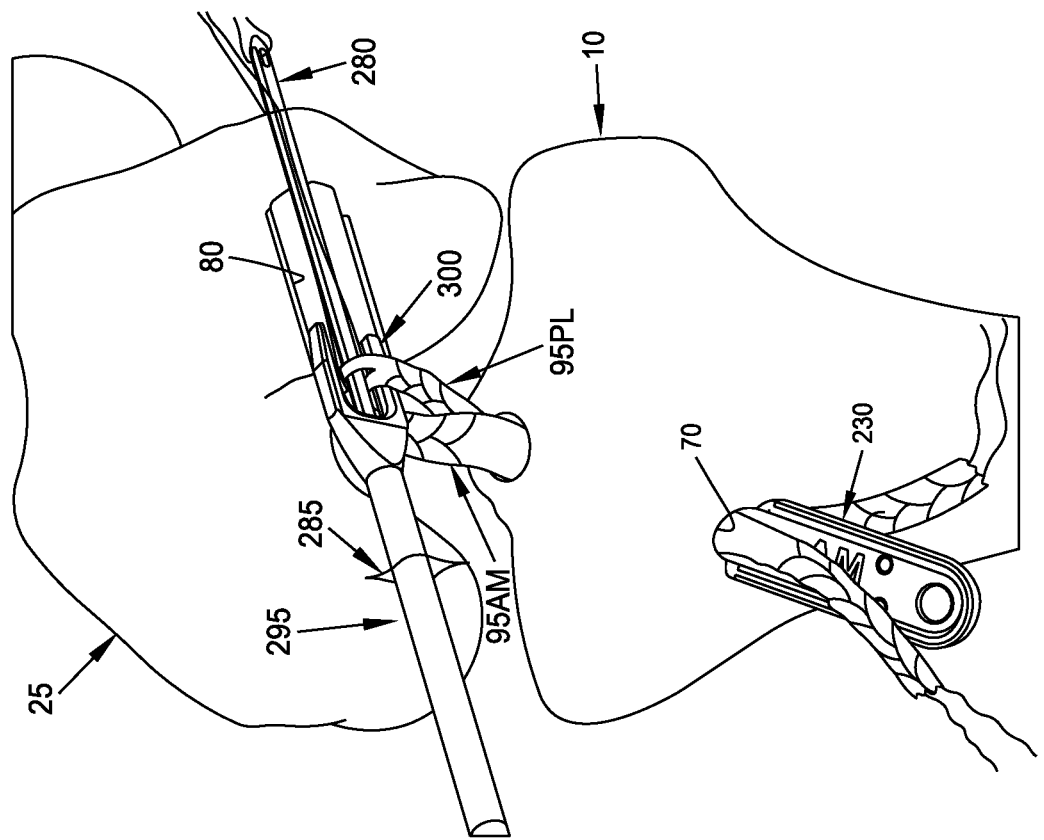

Graft 90 is then pulled slightly into the mouth of femoral tunnel 80 (i.e., by pulling distally on the passing sutures and/or graft tow sutures 105) and then retracted slightly to create a slight amount of slack in the graft. At this point, a cannulated femoral graft inserter 295 (see FIGS. 45-47) is used to assist insertion of graft 90 into femoral tunnel 80. Cannulated femoral graft inserter 295 comprises a body 297 and two legs, i.e., a lower leg 300 and an upper leg 305.

More particularly, femoral graft inserter 295 is used to keep graft bundles 95AM, 95PL separated while graft 90 is pulled into femoral tunnel 80. Femoral graft inserter 295 is first introduced through the medial portal skin incision 85, being careful to avoid catching soft tissue. Femoral graft inserter 295 is passed over femoral guide wire 280 to guide it up to the mouth of femoral tunnel 80. The lower leg 300 of femoral graft inserter 295 is hooked around the PL graft bundle 95PL. The legs 300, 305 of femoral graft inserter 295 are inserted slightly into the notches 185 already formed in femur 25. Graft 90 is then pulled into femoral tunnel 80. Note that the AM and PL bundles 95AM, 95PL are positioned by femoral graft inserter 295 into their respective AM and PL positions as graft 90 is pulled into femoral tunnel 80, whereby to mirror the natural anatomic positions of the AM and PL bundles of the native ACL.

Graft Fixation

Figure 47A:
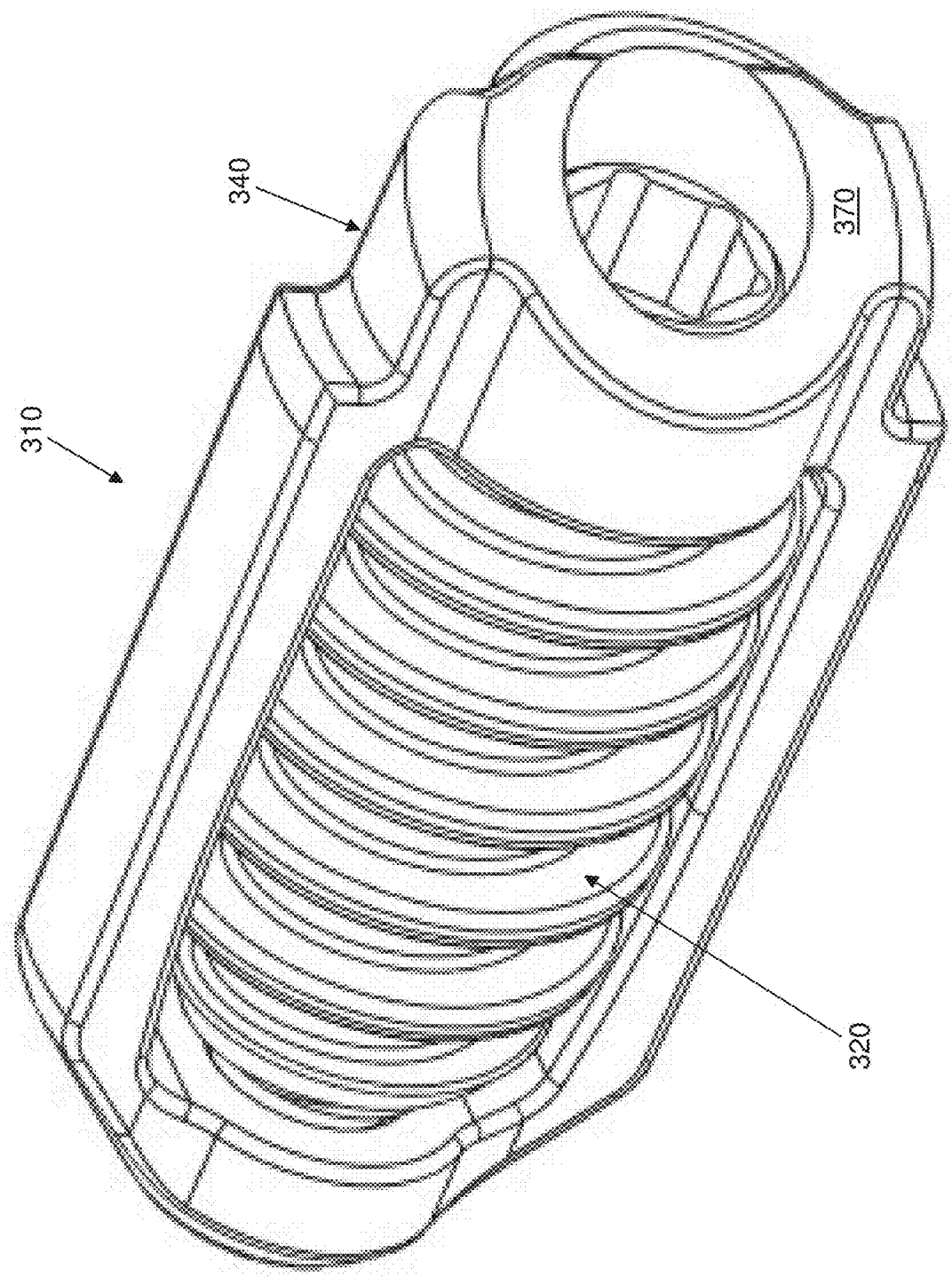

Graft 90 is then ready to be fixated into place with novel femoral and tibial fixation devices, i.e., a femoral fixation device 310 (FIG. 47A) and a tibial fixation device 315 (FIG. 64).

1. Femoral Fixation

Looking now at FIGS. 47A, 48-59A, femoral fixation device 310 comprises two components. The first component (FIG. 48) consists of a femoral fixation screw 320 with a necked down region 325 at its distal tip and a reduced-diameter proximal head (or drive end) 330. Femoral fixation screw 320 provides graft fixation as it is screwed into femoral tunnel 80. Femoral fixation screw 320 tapers or curves to a narrow distal end to facilitate starting and insertion into the femoral tunnel. Also, femoral fixation screw 320 is cannulated to allow the use of femoral guide wire 280 (see above) to guide the femoral fixation screw straight into the femoral tunnel. A hex socket, hexalobe socket, square socket or other shaped socket 335 resides at the proximal end of femoral fixation screw 320 for engagement by an appropriate insertion (tightening) tool (i.e., a driver).

The second component of femoral fixation device 310 is a femoral graft spacer 340 (FIG. 49). Femoral graft spacer 340 has a distal end 342 having an opening 343 and a proximal end 345 having an opening 347. Guide ribs 348 extend between distal end 342 and proximal end 347. Proximal end 345 may be formed flat as shown in FIG. 49 or, in the preferred embodiment, and as shown in FIG. 50, the proximal end 345 may be configured at an angle so as to form an elliptical face to more closely match the femoral bone surface at the joint side mouth of femoral tunnel 80. Guide ribs 348 may have multiple barbs 350 as shown in FIG. 49, or a stepped feature 355 as shown in FIG. 50, to grip onto the side wall of femoral notches 185 and improve holding strength. Femoral graft spacer 340 has an internal cavity 360 sized to receive femoral fixation screw 320. Opening 343 of distal end 342 and opening 347 of proximal end 345 each have a diameter smaller than the diameter of internal cavity 360.

The purpose of femoral graft spacer 340 is to spread and separate the AM and PL bundles 95AM, 95PL as femoral fixation screw 320 is tightened into place in femoral tunnel 80. Furthermore, femoral graft spacer 340 helps direct femoral fixation device 310 straight into femoral tunnel 80 by virtue of guide ribs 348 which track in the previously-created femoral notches 185. Femoral fixation screw 320 and femoral graft spacer 340 are assembled together (see below) so that the two components can rotate independently of one another, thus allowing femoral graft spacer 340 to track in femoral notches 185 and maintain alignment of the graft bundles 95AM, 95PL while femoral fixation screw 320 is tightened so as to secure the graft ligament on the femoral tunnel. The angled proximal end 345 of femoral graft spacer 340 aligns to the bony surface of the femur at the joint side mouth of the femoral tunnel such that the bony defect in the femur is filled and the graft is supported around the elliptical mouth of the femoral tunnel. The angled proximal end 345 of femoral graft spacer 340 may be formed or manufactured in a variety of angles or shapes to best match the anatomy of the femur. Note that the angled proximal end 345 of femoral graft spacer 340 corresponds to the angle β and closely approximates the contour of the mouth of femoral tunnel 80.

Femoral fixation screw 320 and femoral graft spacer 340 are assembled together by capturing the femoral fixation screw within cavity 360 of femoral graft spacer 340. This may be done by deforming femoral graft spacer 340 and snapping it over femoral fixation screw 320. More particularly, to assemble the two components together, the femoral graft spacer 340 is aligned along the side of the femoral fixation screw 320 as shown in FIG. 51. The proximal head 330 of the femoral fixation screw 320 is then inserted into the opening 347 of the proximal end 345 of femoral graft spacer 340 as shown in FIG. 52. The distal tip of the femoral graft spacer 340 is then snapped over the distal tip of the femoral fixation screw 320 so that distal tip 325 of femoral fixation screw 325 is received in opening 343 in the distal end 342 of femoral graft spacer 340, whereby to complete assembly of the two components. See FIG. 53. Note that when femoral fixation screw 320 and femoral graft spacer 340 are assembled together in this manner, femoral fixation screw 320 is free to rotate relative to femoral graft spacer 340.

Figure 54:
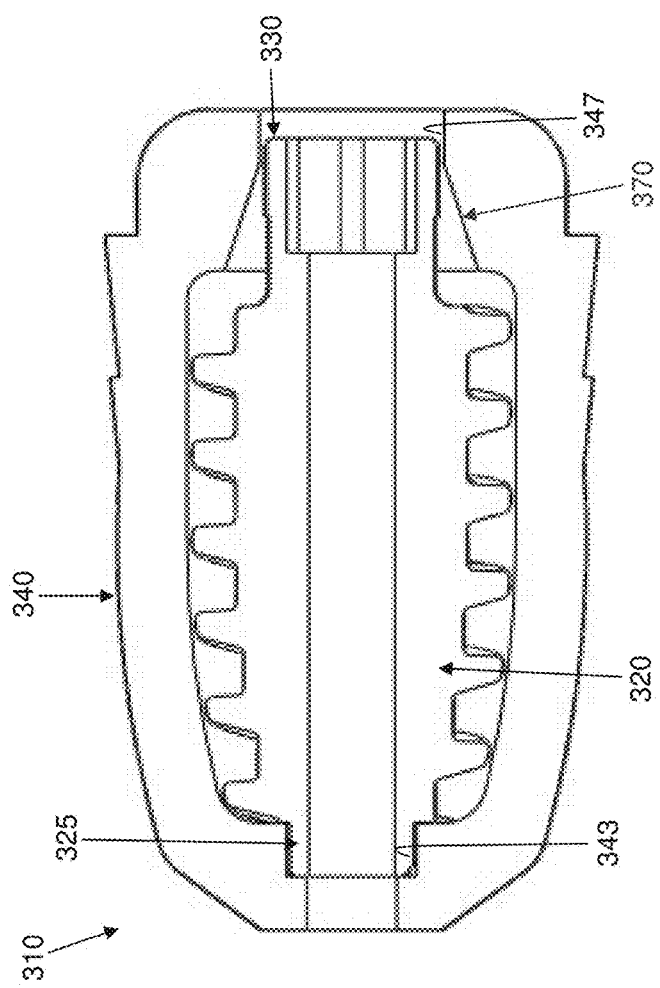

The cross-sectional view in FIG. 54 illustrates femoral graft spacer 340 assembled onto femoral fixation screw 320. There is an angled surface 370 on the inside of femoral graft spacer 340 that allows femoral fixation screw 320 to be partially inserted into the femoral graft spacer prior to snapping the components into place. The femoral fixation screw is then supported on both ends of the femoral graft spacer (i.e., by engagement of the distal end 325 of femoral fixation screw 320 in opening 343 of femoral graft spacer 340, and by engagement of the proximal end 330 of femoral fixation screw 320 in opening 347 of femoral graft spacer 340), and can rotate freely relative to the femoral graft spacer.

Femoral graft spacer 340 functions as a means to align and separate the graft bundles 95AM, 95PL in femoral tunnel 80 and to fill the bony defect. Femoral graft spacer 340 can be positioned to spread the graft bundles 95AM, 95PL into their correct anatomic positions, regardless of the rotational position of femoral fixation screw 320. Also, femoral graft spacer 340 may function as a "strain relief", allowing the tension in graft 90 to be spread over the entire length of femoral fixation device 310.

Femoral fixation screw 320 and femoral graft spacer 340 may be made from metal, plastic (e.g., PEEK) and/or a bioabsorbable material.

Figure 55:
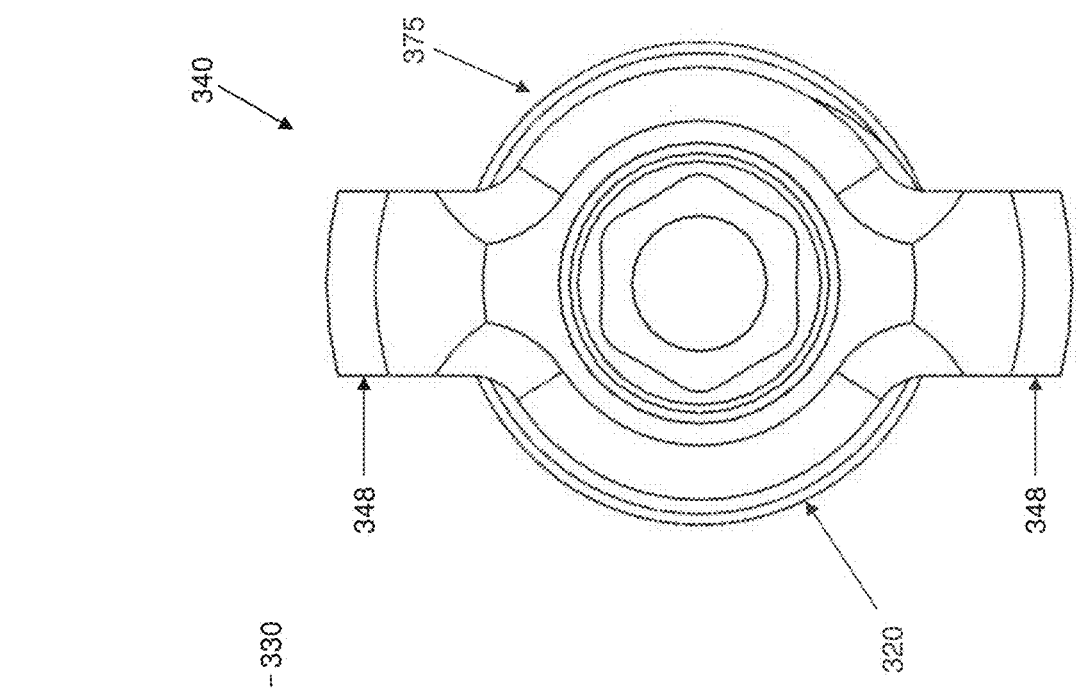

The end view shown in FIG. 55 illustrates the contoured outer wall 375 of femoral graft spacer 340 for graft seating. The contoured outer wall 375 cooperates with guide ribs 348 to define graft recesses to engage with, and provide alignment of, the graft bundles 95AM, 95PL. Note that femoral fixation screw 320 extends radially outboard of contoured outer wall 375 of femoral graft spacer 340. The shape of contoured outer wall 375 may be a variety of shapes to allow space for the graft strands. Guide ribs 348 that span the length of femoral graft spacer 340 are fit into the notches 185 previously formed in femoral tunnel 80. In addition to guiding femoral fixation device 310 along femoral tunnel 80, guide ribs 348 separate the graft bundles 95AM, 95PL and organize them onto one side or the other of femoral fixation device 310.

Femoral graft spacer 340 has smooth radii around critical corners to ensure strain-relieved fixation of the graft bundles. As femoral fixation device 310 is advanced along femoral tunnel 80, guide ribs 348 glide into notches 185 of femoral tunnel 80 and center femoral graft spacer 340 onto the elliptical entrance of femoral tunnel 80, thus separating the graft bundles 95AM, 95PL into their anatomically correct AM and PL locations. See FIG. 56.

Figure 57:
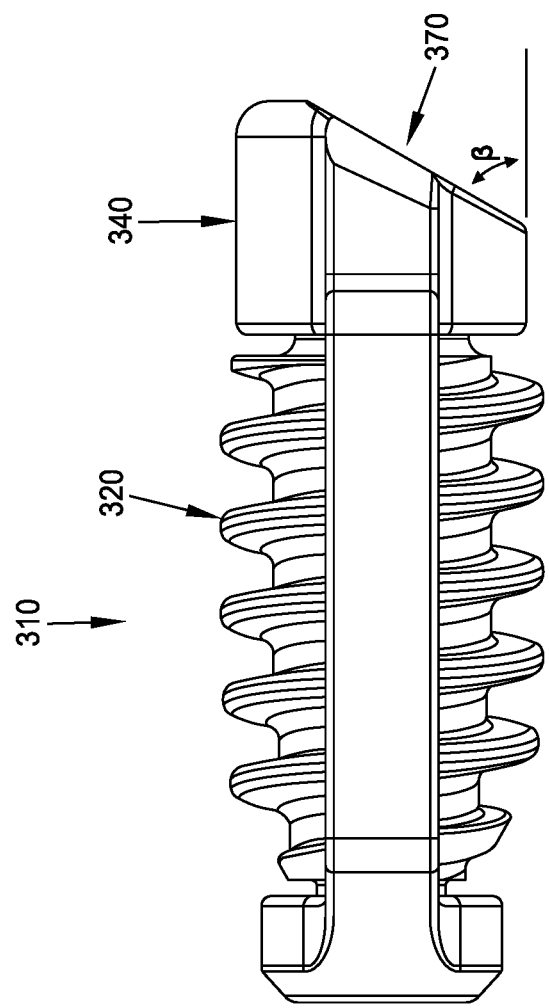
Figure 56:
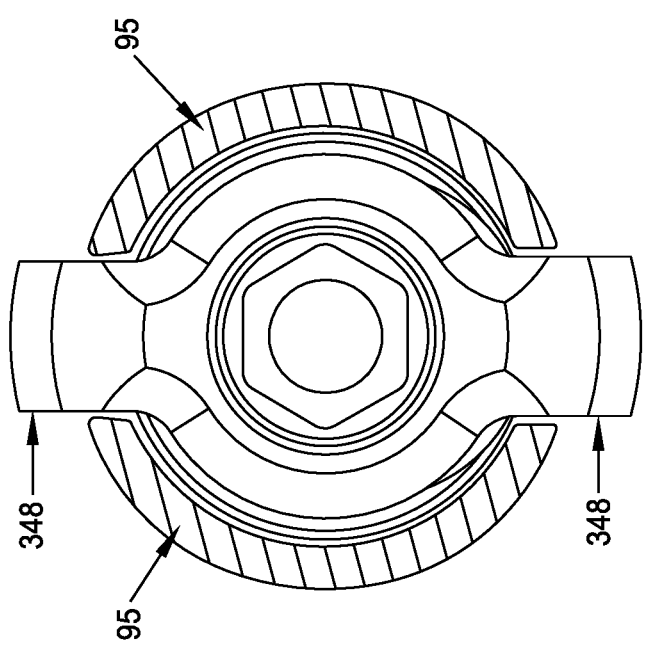
Figure 59B:
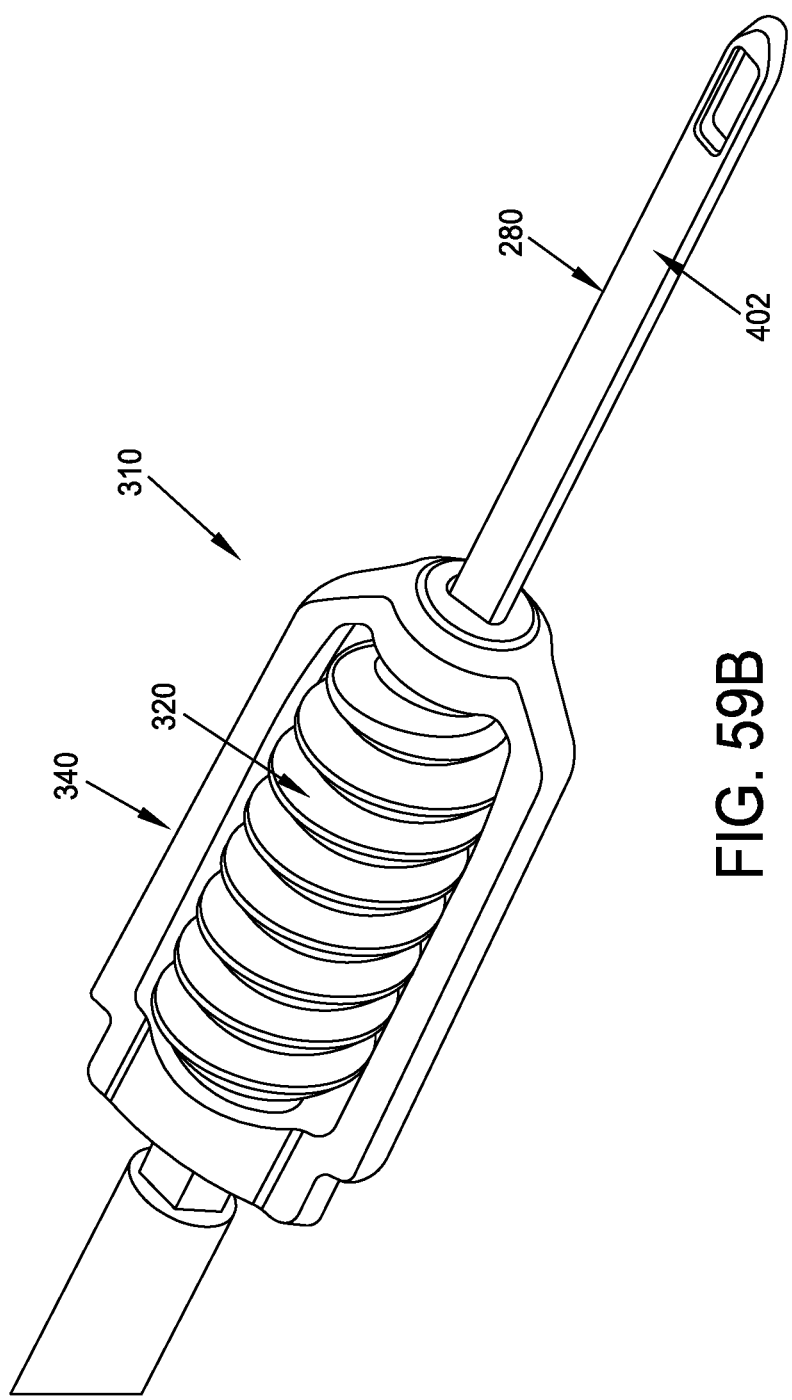

Proximal end 345 of femoral graft spacer 340 is angled (approximately equal to β) to create the mating elliptical, oval shape needed to fill the elliptical, oval-shaped joint-side entrance of femoral tunnel 80. The angled shape of the proximal end of the femoral graft spacer fills the femoral tunnel entrance and urges the graft up against the tunnel entrance so as to mimic the wider anatomic footprint of the natural femoral insertion. The side view of the femoral fixation device is shown in FIG. 57, illustrating the angle β.

Looking now at FIG. 58, which is a top view, femoral graft spacer 340 includes a tapered lead-in surface 380 that helps start the femoral graft spacer into femoral tunnel 80 and tunnel notches 185.

The lead tip 385 of femoral graft spacer 340 has a slot 390 that can be engaged with femoral guide wire 280. See FIGS. 59A and 59B.

Femoral guide wire 280 is used to guide the femoral fixation device 310 to the femoral tunnel and to rotate the femoral fixation device 310 as needed so that the femoral fixation device is properly oriented with respect to the graft bundles 95AM, 95PL and with respect to the notches 185 in the femoral tunnel 80. A guide wire dial 395 (FIG. 60A) slips over the distal end of femoral guide wire 280, with a slot 400 on guide wire dial 395 engaging with flats 402 on femoral guide wire 280, and is rotated so as to properly orient femoral fixation device 310 with respect to graft bundles 95AM, 95PL and femoral notches 185. See FIG. 60B.

Figure 61:
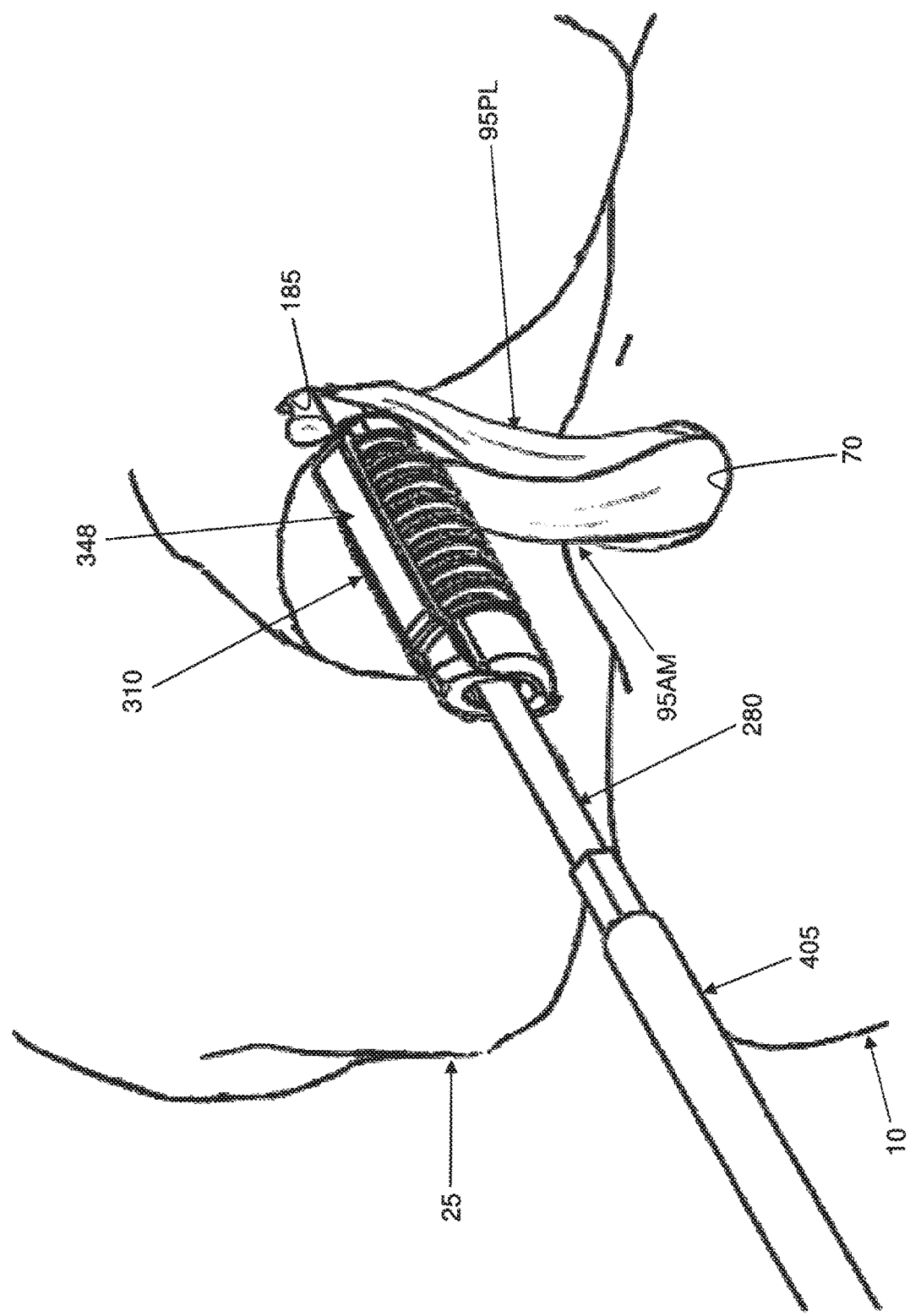

The AM and PL bundles 95AM, 95PL separate from each other on opposite sides of femoral graft spacer 340 as femoral fixation device 310 begins to engage with the femoral tunnel 80 (FIG. 61). The AM and PL bundles 95AM, 95PL may be further manipulated, or spread out, with one bundle on each side of femoral fixation device 310. The graft bundles 95AM, 95PL then align with, and fit in between, the recesses between the bone tunnel 80 and the femoral fixation device 310. See FIG. 61 showing the femoral fixation device 310 with its guide ribs 348 aligned with notches 185.

Figure 62:
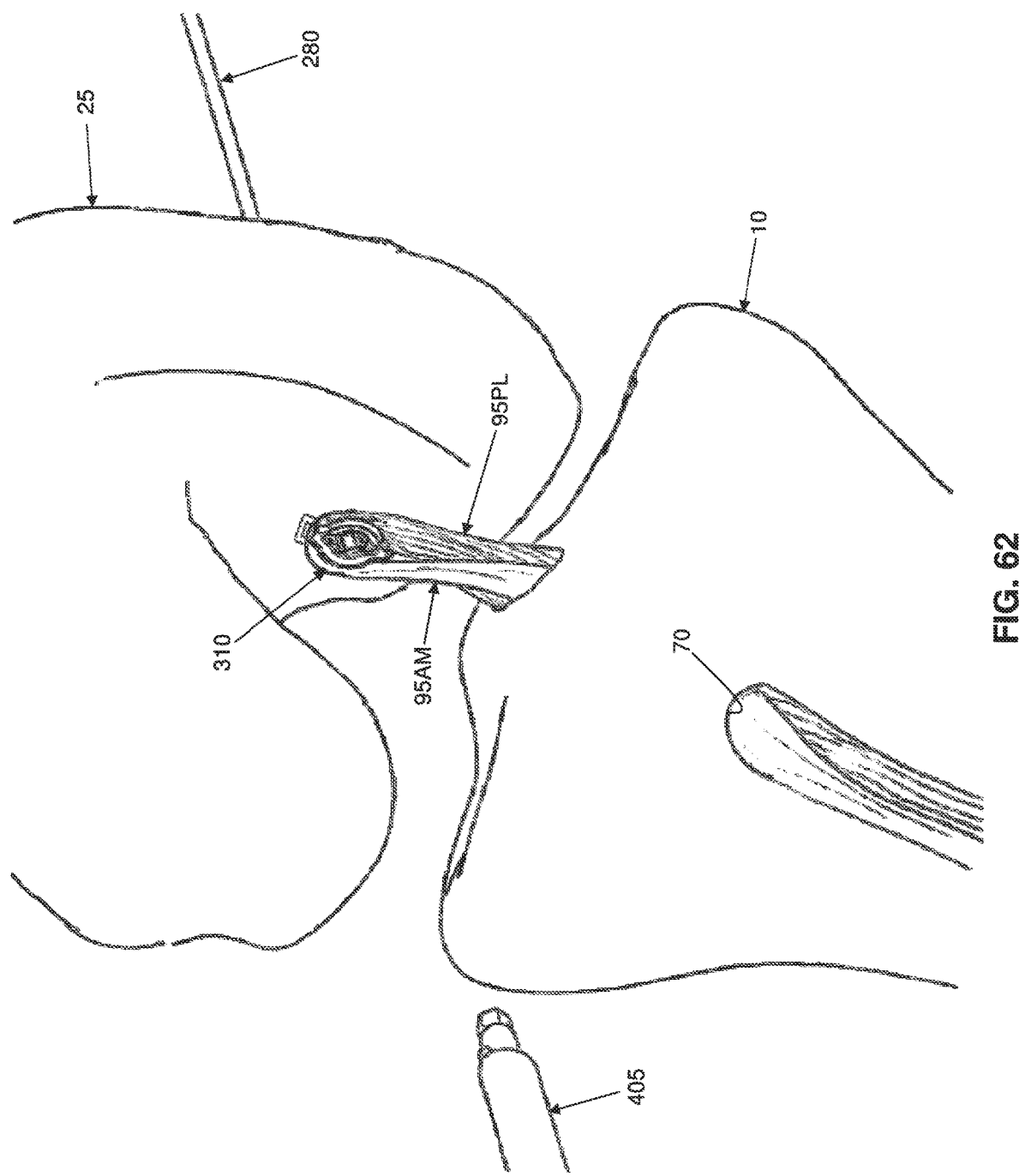

Femoral fixation device 310 is then fully advanced into femoral tunnel 80, i.e., by using a driver 405 to turn femoral fixation screw 320, which causes the threads of the femoral fixation screw to engage graft 90 and the side walls of femoral tunnel 80 and thereby advance femoral fixation device 310 up the femoral tunnel. As femoral fixation device 310 advances up femoral tunnel 80, femoral fixation device 310 creates an interference fit between the femoral fixation device, the graft and the side walls of femoral tunnel 80. Note that as femoral fixation device 310 advances within femoral tunnel 80, tunnel notches 185 act as tracks for guide ribs 348 of femoral fixation device 310, keeping the fixation centered in the femoral tunnel and maintaining separation of graft bundles 95AM, 95PL. When femoral fixation device 310 is fully seated in femoral tunnel 80, the canted or angled surface 370 of the femoral graft spacer is approximately flush, or even with, the bone surface adjacent the joint-side mouth of femoral tunnel 80. See FIG. 62.

Figure 63:
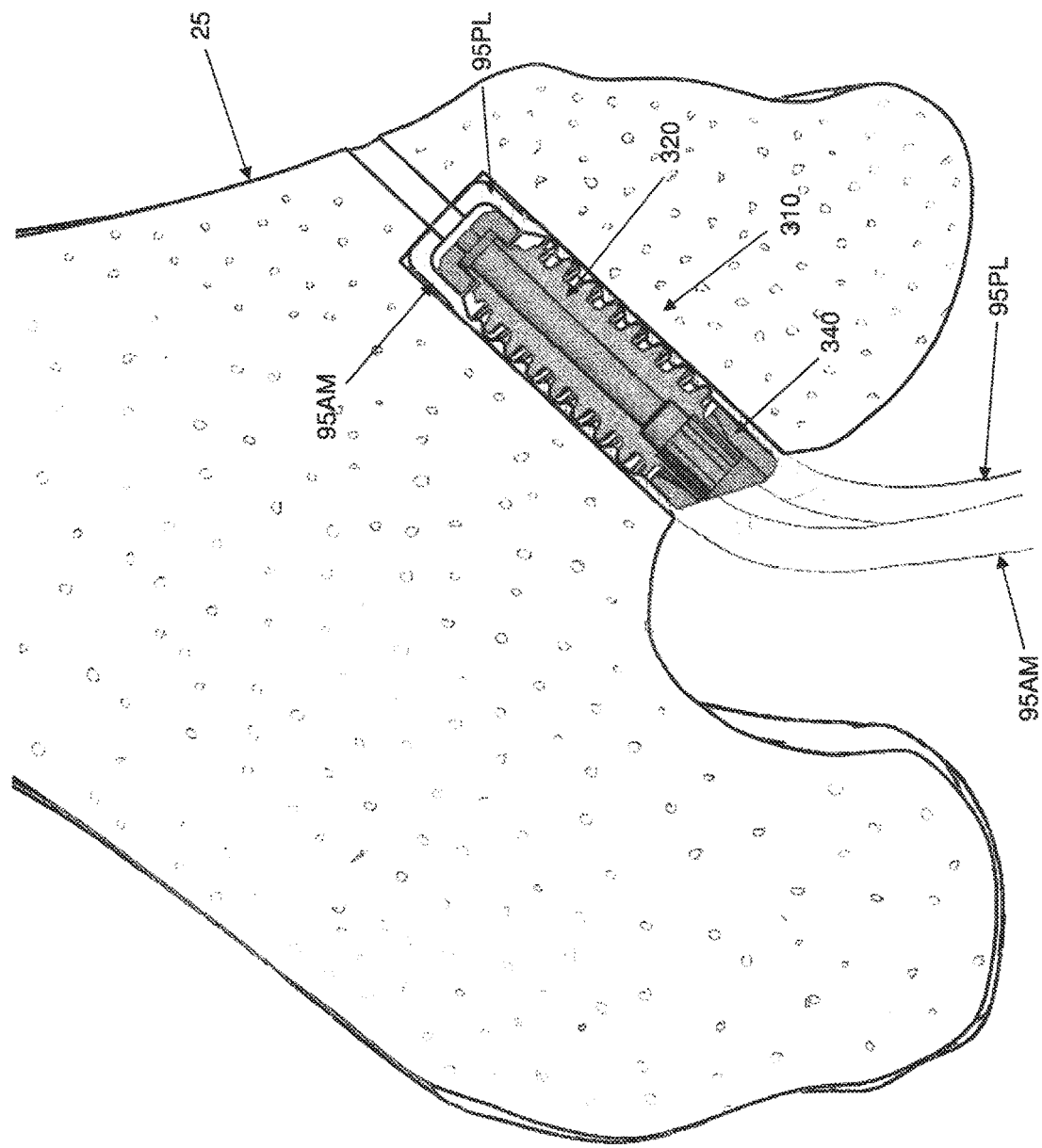

In the completed femoral ligament construct, the femoral fixation device 310 is seated approximately flush with the joint-side mouth of the femoral tunnel 80. The graft is fixated between the femoral fixation screw threads and the femoral tunnel. FIG. 63 shows a cross-section through the axis of the femoral fixation device that is perpendicular to the guide ribs 348 of the femoral graft spacer. FIG. 63 illustrates how the graft is pressed between the femoral fixation screw and the side wall of the femoral tunnel and the graft fibers are interspersed between the threads of the femoral fixation screw. The graft exits the femoral tunnel in the area of the recesses of the femoral graft spacer, with the AM and PL bundles 95AM, 95PL separated into their correct anatomic positions.

The femoral fixation device 310 provides significant advantages in femoral graft fixation:

1. The final reconstructed graft construct more closely mimics the natural anatomic footprint of the femoral ligament insertion, resulting in a biomechanically superior reconstruction. The AM and PL bundles 95AM, 95PL are spread out over the elliptical anatomic footprint, with the femoral graft spacer 340 holding the graft to the rim of the femoral tunnel 80 about the periphery of the elliptical mouth of the femoral tunnel.

2. The graft is secured at the joint-side mouth of the femoral tunnel (aperture fixation), eliminating the possible "windshield wiper" action of the graft over the bone surface. This windshield wiper action can lead to wear of the graft, wear of the bone surface, widening of the femoral tunnel, and potentially a failed reconstruction.

3. In the event that the graft needs to be revised at a later date, the entire construct can be easily removed by removing the femoral fixation device 310 from the femur (e.g., by unscrewing the femoral fixation screw 320). The femoral graft spacer 340 and the femoral fixation screw 320 will remove as a single assembly, aiding in the revision process.

4. Femoral graft spacer 340 also provides strain relief. More particularly, the strain on graft 90 is distributed over the entire length of femoral graft spacer 340, rather than the abrupt strain resulting from the transition of a highly-compressed graft emerging from a standard interference screw/bone interface.

5. And, guide ribs 348 of the femoral graft spacer 340 follow notches 185 in femoral tunnel 80, ensuring that graft 90 remains centered in the femoral tunnel, evenly forcing graft 90 against the side wall of femoral tunnel 80.

2. Tibial Fixation

Tibial fixation is effected using a tibial fixation device 315 which is generally similar to the aforementioned femoral fixation device 310. Tibial fixation device 315 comprises a tibial graft spacer 410 and a tibial fixation screw 415. See FIG. 64.

Figure 66:
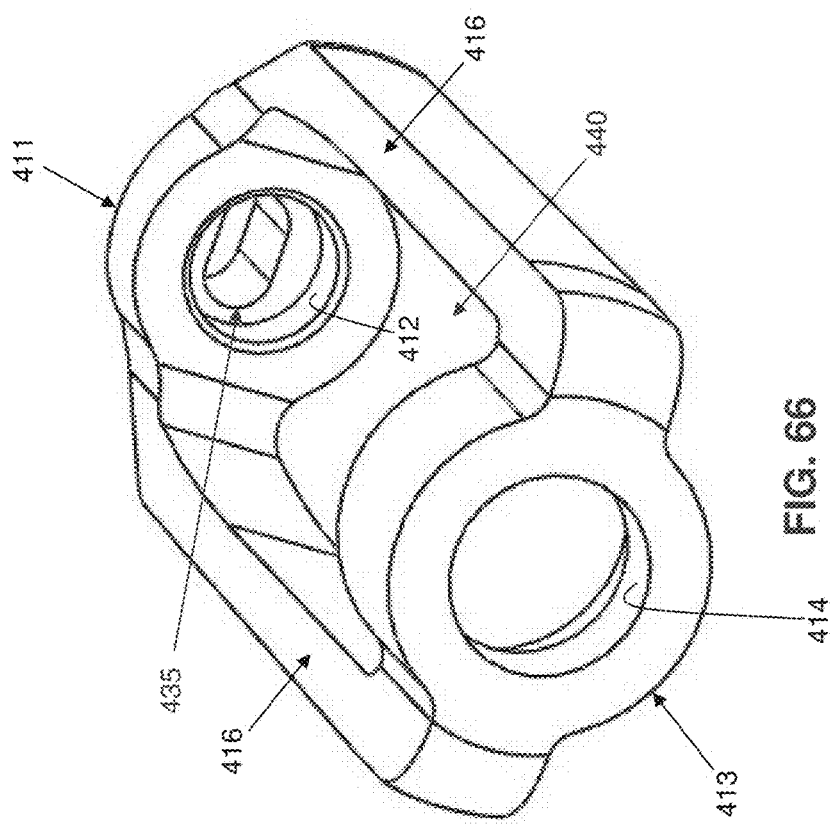

Looking now at FIG. 65, tibial graft spacer 410 has a distal end 411 having an opening 412, and a proximal end 413 having an opening 414. Guide ribs 416 extend between distal end 411 and proximal end 413 of tibial graft spacer 410. Tibial graft spacer 410 has an internal cavity 440 sized to receive tibial fixation screw 415, as will hereinafter be discussed in greater detail. It should be appreciated that tibial graft spacer 410 is generally similar to femoral graft spacer 340 previously discussed, and shares a number of common features. These common features include an angled surface 420 whereby to provide an elliptical shape (but disposed on the distal end of the tibial graft spacer 410, rather than on the proximal end as is the case with the femoral graft spacer 340), tapered lead-in surfaces 425 to aid insertion into the tibial tunnel, a contoured outer wall 430 for fixating the graft in the tibial tunnel, a slot 435 at the distal tip of distal end 411 of the tibial graft spacer 410 for, optionally, engaging with flats on a guide wire, and cannulation through the center of the tibial graft spacer (and its associated tibial fixation screw) for receiving a guide wire. See FIG. 66. If desired, guide ribs 416 can also include one or more barbs and/or one or more stepped features (analogous to barbs 350 and stepped feature 355 of femoral graft spacer 340) to grip onto the side wall of tibial notches 225 and improve holding strength.

Figure 67:
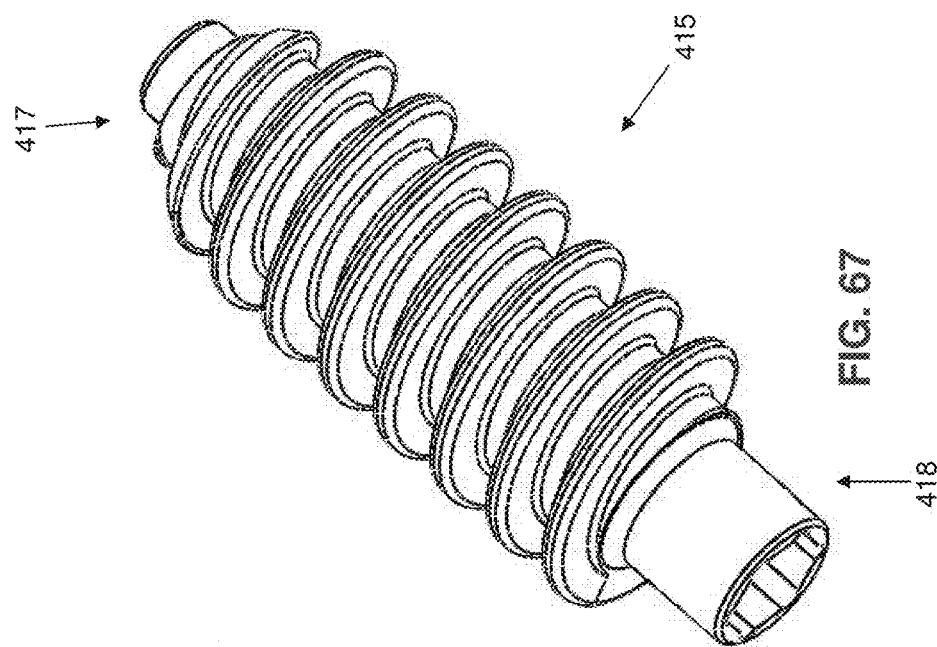

Tibial fixation screw 415 is shown in FIG. 67. Tibial fixation screw 415 has a necked down region 417 at its distal tip and a reduced-diameter proximal head (or drive end) 418. Tibial fixation screw 415 tapers or curves to a narrow distal end to facilitate starting and insertion into the tibial tunnel. With the present invention, tibial fixation screw 415 may be the same design as femoral fixation screw 320, but may be made in different lengths (i.e., 5 mm-10 mm longer) in order to utilize more of the tibial tunnel, which is typically longer than the femoral tunnel (in which case tibial graft spacer 410 has its length correspondingly adjusted).

Figure 68:
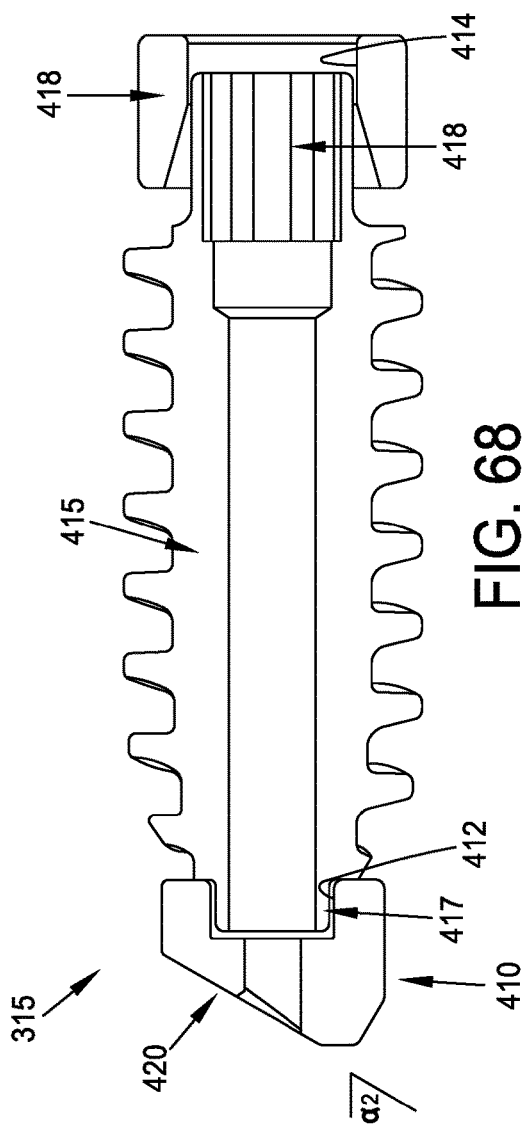

Tibial fixation device 315 is shown in cross-section in FIG. 68. The angle $\alpha_2$ is shown at the angled surface 420 at the distal tip of tibial fixation device 315.

Figure 69:
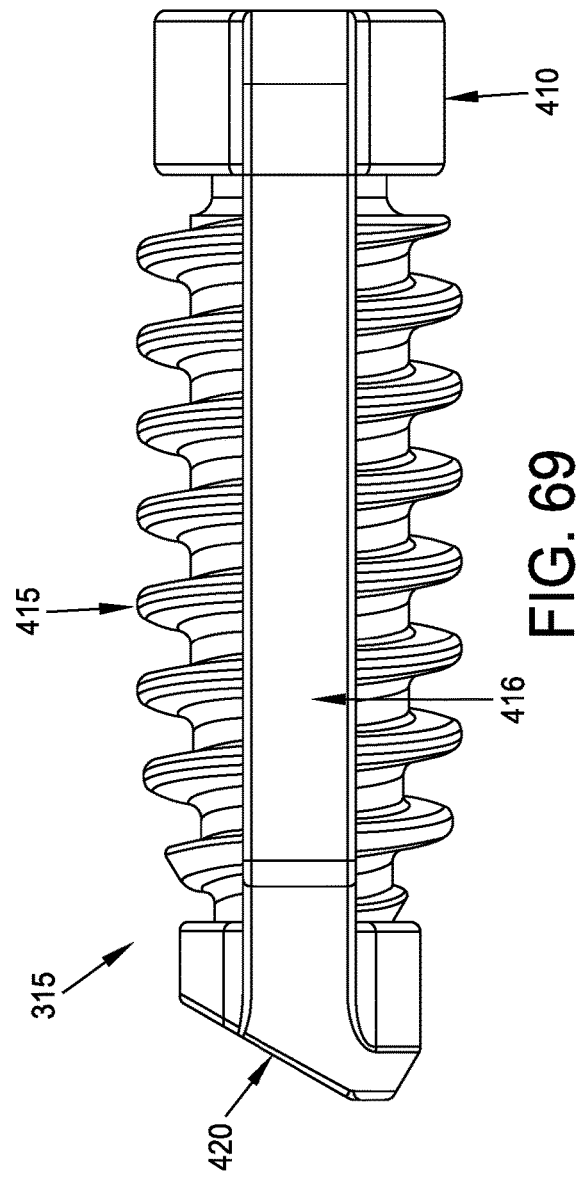

FIG. 69 illustrates tibial graft spacer 410 and the tibial fixation screw 415 in assembled form, whereby to form the complete tibial fixation device 315. It will be appreciated that tibial graft spacer 410 and tibial fixation screw 415 are assembled together in substantially the same manner as femoral graft spacer 340 and femoral fixation screw 320 are assembled, i.e., by snapping tibial fixation screw 415 into cavity 440 formed in tibial graft spacer 410 (i.e., by deforming tibial graft spacer 410 and snapping it over tibial fixation screw 415). More particularly, to assemble the two components together, the tibial graft spacer 410 is preferably aligned along the side of tibial fixation screw 415. The proximal head (or drive end) 418 of tibial fixation screw 415 is inserted into opening 414 of the proximal end 413 of tibial graft spacer 410. The distal tip of tibial graft spacer 410 is then snapped over the distal tip of tibial fixation screw 415 so that the distal tip 417 of tibial fixation screw 415 is received in opening 412 in the distal end of tibial graft spacer 410, whereby to complete assembly of the two components. It will also be appreciated that when tibial graft spacer 410 and tibial fixation screw 415 are assembled together in the foregoing manner, tibial fixation screw 415 will be free to rotate relative to tibial graft spacer 410.

The angle $\alpha_2$ at the distal tip of tibial fixation device 315 corresponds to the angle resulting from the tibial tunnel drilling technique discussed above. The angled surface 420 at angle $\alpha_2$ creates a close anatomic alignment between the bone surface (i.e., tibial plateau 50) and tibial fixation device 315, and also secures the graft bundles 95AM, 95PL in their proper anatomic positions.

Similar to the femoral fixation device 310, the tibial fixation device 315 preferably has the aforementioned contoured outer wall 430 which cooperates with guide ribs 416 to define graft recesses on the top and bottom sides of the tibial graft spacer to engage with, and provide alignment of, graft bundles 95AM, 95PL, whereby to urge graft bundles 95AM, 95PL into their anatomic positions. See FIG. 70, viewed from the distal tip of tibial fixation device 315. The recesses shown are preferably crescent-shaped (i.e., the same shape as the recesses of femoral graft spacer 340), although the recesses could have some other shape if desired.

Tibial graft spacer 410 is sized relative to tibial fixation screw 415. In one preferred form of the present invention, the graft recesses of tibial graft spacer 410 are smaller in size than tibial fixation screw 415. Guide ribs 416 of the tibial graft spacer 410 are larger than the screw diameter for alignment and graft bundle separation.

Guide ribs 416 that span the length of tibial graft spacer 410 are fit into notches 225 previously formed in tibial tunnel 70. In addition to guiding tibial fixation device 315 along tibial tunnel 70, guide ribs 416 separate the graft bundles 95AM, 95PL and organize them onto one side or the other of tibial fixation device 315. It should be appreciated that tibial graft spacer 410 can be positioned to spread the graft bundles 95AM, 95PL into their correct anatomic position, regardless of the rotational disposition of tibial fixation screw 415.

Tibial fixation screw 415 and tibial graft spacer 410 may be made from metal, plastic (e.g., PEEK) and/or a bioabsorbable material.

Figure 72:
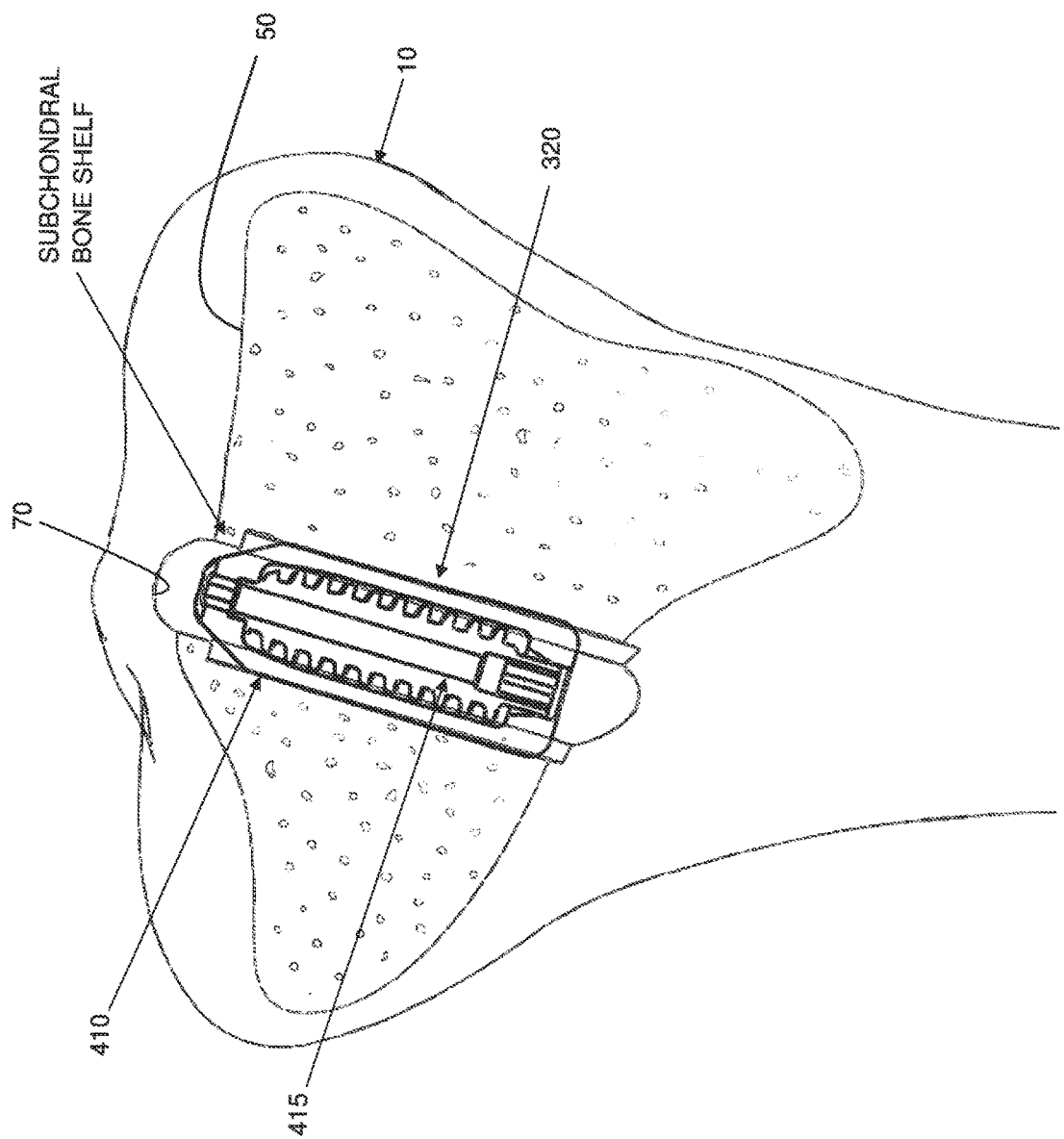

In the final step of the ligament reconstruction, tibial fixation device 315 is advanced into tibial tunnel 70 using a driver 450. FIG. 71 shows driver 450, tibial fixation device 315 and the notched tibial tunnel 70. The graft is omitted from FIGS. 71-73 in order to illustrate the alignment of the tibial fixation device 315 and the tibial tunnel 70. Tibial fixation device 315 is preferably advanced into tibial tunnel 70 in the following manner. Tibial graft separator 230 is removed from tibial tunnel 70. Tibial fixation device 315, manipulated by driver 450, is advanced between graft bundles 95AM, 95PL, brought to the anteromedial mouth of tibial tunnel 70, has its guide ribs 416 aligned with tunnel notches 225, and tibial fixation screw 415 is turned with driver 450, causing tibial fixation device 315 to advance along tibial tunnel 70, creating an interference fit between tibial fixation device 315, graft bundles 95AM, 95PL and the side wall of tibial tunnel 70. Note that as tibial fixation device 315 is advanced up tibial tunnel 70, guide ribs 416 of tibial fixation device 315 orient and separate the graft bundles 95AM, 95PL into their anatomically correct AM and PL locations. If desired, tibial fixation device 315 can be set using driver 450 alone (as shown in FIG. 71) or, if desired, tibial fixation device 315 and driver 450 can be tracked over a guide wire (which may be a guidewire such as guidewire 280 having flats 402) so that the guidewire can be used to rotate tibial fixation device 315 to a desired angular disposition (i.e., to line up with tibial notches 225 and separate graft bundles 95AM, 95PL).

In the case of tibial fixation device 315, the strength of the construct is enhanced by driving the fixation into the tibial tunnel until distal end 411 of tibial graft spacer 410 contacts the subchondral bone at the distal end of tibial notches 225 (which terminate proximal of tibial plateau 50). See FIG. 72 which is a cross-sectional view through the axis of tibial fixation device 315, in the central plane of guide ribs 416 of tibial graft spacer 410. As noted above, during the preparation of the tibial tunnel, notcher 165 is preferably driven up to the subchondral bone but then stopped, leaving a shelf for the distal end of tibial fixation device 315 to rest against. Tension in graft 90 pulls tibial fixation device 315 against the subchondral bone shelf. The combination of strong aperture fixation and the resistance of tibial fixation device 315 against the subchondral shelf creates a very strong tibial ligament construct (i.e., a very strong fixation of graft 90 to tibia 10). As tibial fixation device 315 advances up tibial tunnel 70, tibial fixation device 315 creates an interference fit between the tibial fixation device 315, graft 90 and the side walls of tibial tunnel 70, in the same manner as with the femoral fixation device. Furthermore, the fibers of graft 90 lodge between the screw threads of tibial fixation screw 415 in a manner similar to that of femoral fixation device 310, contributing to the strong aperture fixation.

Figure 73:
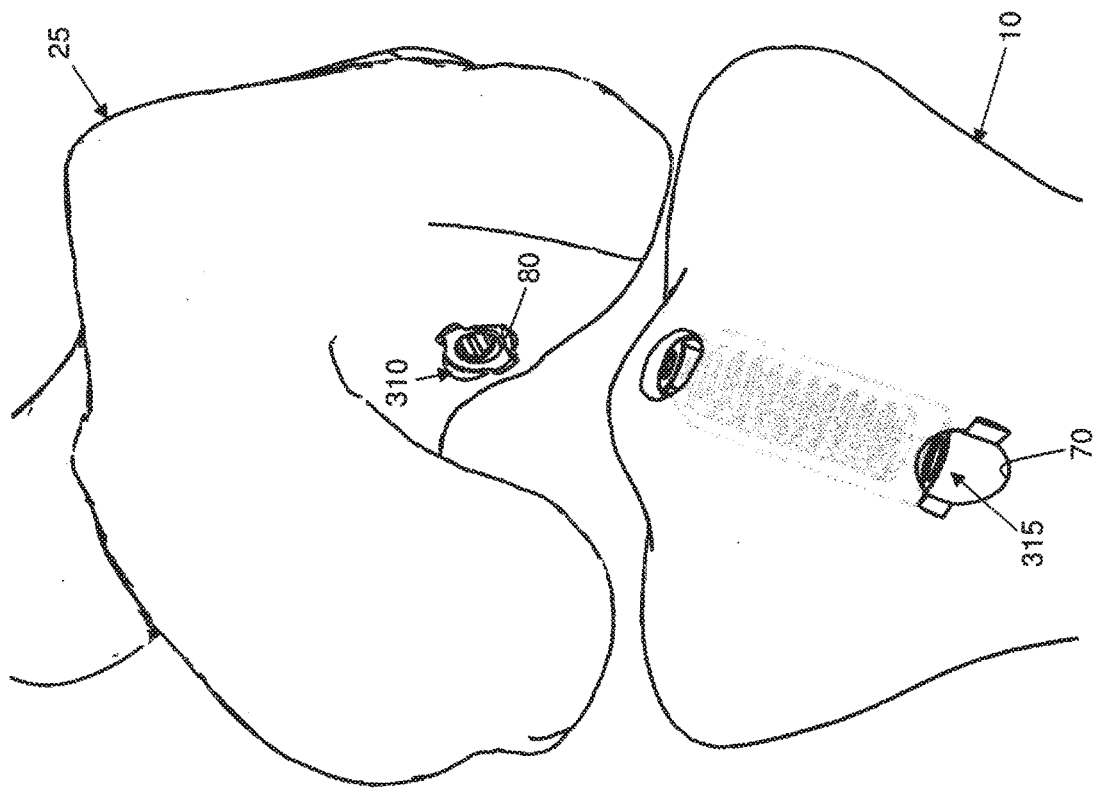

FIG. 73 shows femoral fixation device 310 and tibial fixation device 315 secured in their respective positions within femoral tunnel 80 and tibial tunnel 70, respectively. Both femoral fixation device 310 and tibial fixation device 315 lie approximately flush with the bone surfaces surrounding the mouths of their respective bone tunnels on the inside of the knee joint (i.e., with angled surface 370 of femoral graft spacer 340 disposed at the proximal end of femoral tunnel 80 proximate joint space 60, and with angled surface 420 of tibial graft spacer 410 disposed at the distal end of tibial tunnel 70 proximate joint space 60). Guide ribs 348 of femoral graft spacer 340 lie within femoral notches 185, and guide ribs 416 of tibial graft spacer 410 lie within tibial notches 225, providing definitive passageways for the AM and PL bundles 95AM, 95PL.

Figure 74:
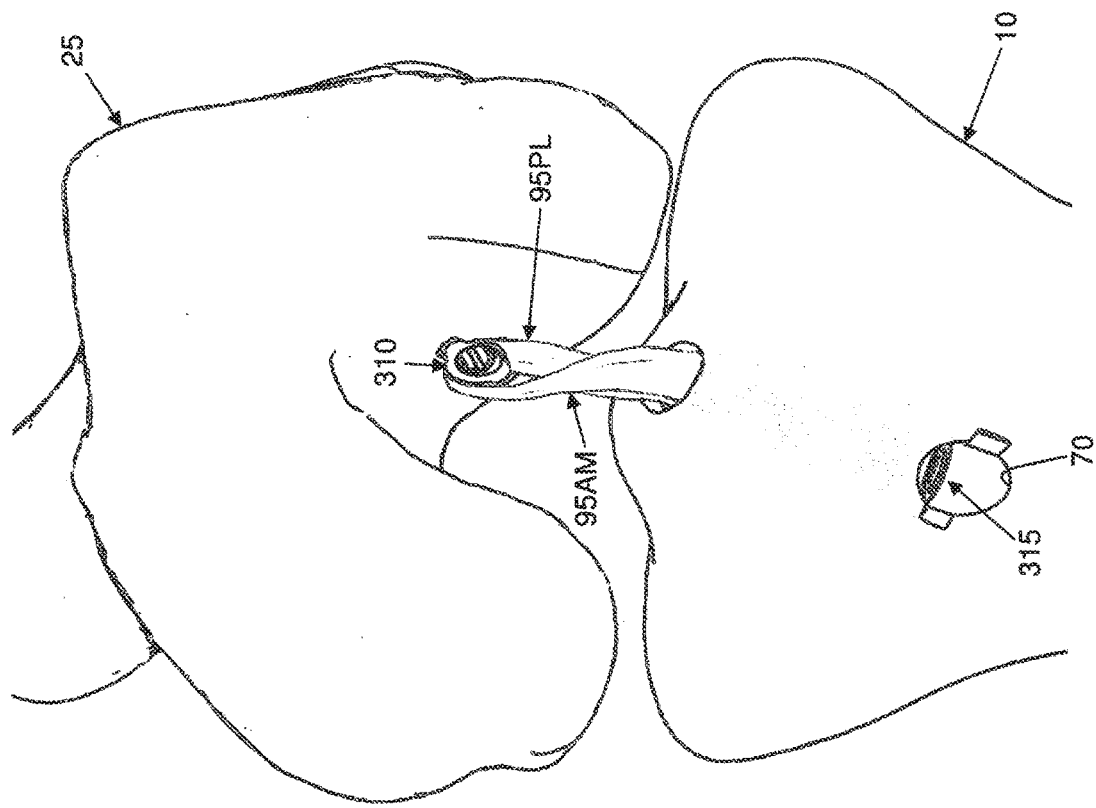
FIGS. 73 and 74 are schematic views showing a graft ligament reconstruction performed in accordance with the present invention.

The finished construct, showing the AM and PL bundles 95AM, 95PL in position, is shown in FIG. 74.

Tibial fixation device 315 provides significant advantages in tibial graft fixation:

1. The final reconstructed graft construct more closely mimics the natural anatomic footprint of the tibial ligament insertion, resulting in a biomechanically superior reconstruction. The AM and PL bundles 95AM, 95PL are spread out over the elliptical anatomic footprint, with the tibial graft spacer 410 holding the graft to the rim of tibial tunnel 70 about the periphery of the elliptical mouth of the tibial tunnel.

2. The graft is secured at the joint-side mouth of the tibial tunnel (aperture fixation), eliminating the possible "windshield wiper" action of the graft over the bone surface. This windshield wiper action can lead to wear of the graft, wear of the bone surface, widening of the tibial tunnel, and potentially a failed reconstruction.

3. The bony defect from the drilling process is filled by tibial fixation device 315.

4. Tibial graft spacer 410 ensures that tibial fixation device 315 goes in straight and follows notches 225 in tibial tunnel 70, eliminates screw divergence and enhances fixation strength by distributing forces over a larger area.

5. In the event that the graft needs to be revised at a later date, the entire construct can be easily removed by loosening tibial fixation device 315 from the tibia (e.g., by unscrewing tibial fixation screw 415 from tibial tunnel 70). Tibial graft spacer 410 and tibial fixation screw 415 will remove as a single assembly, aiding in the revision process.

6. Tibial graft spacer 410 provides strain relief to distribute the stress over the face of the tibial fixation device 310, whereby to create a smooth and gradual transition from the compression of tibial fixation screw 415.

The foregoing discussion describes the preferred embodiments of femoral fixation device 310 and tibial fixation device 315 and and their preferred method of use. However, if desired, alternative constructions may be utilized with the present invention.

By way of example but not limitation, femoral fixation device 310 and/or tibial fixation device 315 may be modified to permit the components to be manufactured using other methods such as injection molding. FIGS. 75A and 75B illustrate design modifications to tibial fixation device 315 that may permit injection molding. The proximal opening 414 of tibial graft spacer 410 is formed as a tapered slot or hole 455, such that the opening does not form an undercut surface for the purpose of molding. The taper still permits assembly of tibial fixation screw 415 inside of tibial graft spacer 410, as described above. Tibial fixation screw 415 may have a deeper, tapered drive recess 460 (formed by an alternate polygon, such as the five-sided polygon shown) formed in reduced diameter proximal head (or drive end) 415 of tibial fixation screw 415. This would provide more surface area to distribute drive forces, which can be an important consideration where the component is molded from plastic.

Similar changes may be made to the femoral fixation device 310.

Additionally, small protrusions 465 (FIG. 76) may extend longitudinally from the distal end of the femoral graft spacer 340. These protrusions capture a graft between the end of femoral fixation device 310 and the far end of the femoral tunnel, as may be commonly used in tenodesis procedures of the biceps tendon, or other soft tissue connections.

In another version of the present invention, the guide ribs 348 of the femoral graft spacer 340 may not be symmetric, but positioned asymmetrically about the femoral fixation screw. See FIG. 77. This can be useful when the graft is closely compressed on the narrow side, and more spread out on the broader side. It may also be useful when a bone block graft is to be positioned on one side.

Similar changes may be made to the tibial fixation device.

Figure 78:
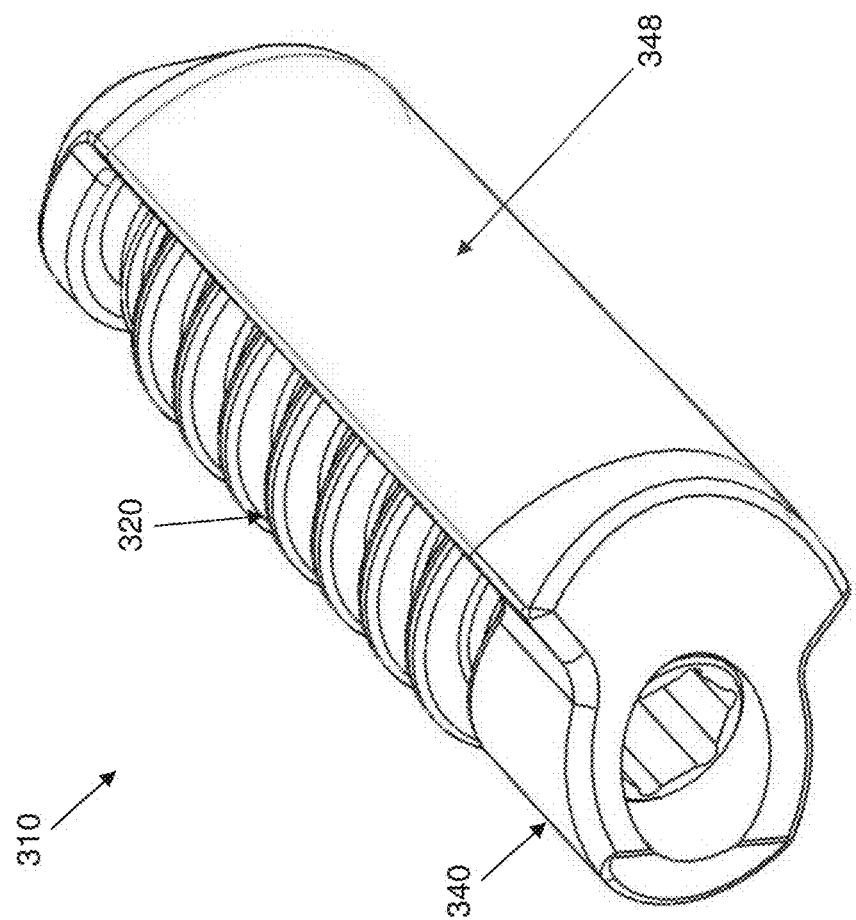

In another version of the present invention, and looking now at FIG. 78, femoral graft spacer 340 may be formed with a single guide rib 348 positioned symmetrically or asymmetrically about femoral fixation screw 320. This can be useful when the entirety of the graft is intended to be secured in one area. This may also be useful when a bone block graft is to be positioned on one side.

Similar changes may be made to the tibial fixation device.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A graft fixation device comprising:
a graft separator comprising a distal end, a proximal end, a cavity disposed between the distal end and the proximal end, and at least one guide rib disposed radially outboard of the cavity and extending longitudinally between the distal end and the proximal end, wherein the distal end of the at least one guide rib comprises a protrusion extending longitudinally from the distal end of the graft separator; and
an interference screw rotatably mountable within the cavity of the graft separator, the interference screw comprising a distal end, a proximal end, and a screw thread disposed intermediate thereof, the screw thread disposed radially outboard of the cavity of the graft separator and radially inboard of the at least one guide rib of the graft separator;
4. wherein the distal end of the graft separator comprises an opening for receiving the distal end of the interference screw; and
5. wherein the opening in the distal end of the graft separator has a diameter smaller than the diameter of the cavity.

2. A graft fixation device according to claim 1 wherein the graft separator comprises two guide ribs and two protrusions, and further wherein the two protrusions extend longitudinally from the distal end of the graft separator.

3. A graft fixation device according to claim 1 wherein the proximal end of the graft separator comprises an opening for receiving the proximal end of the interference screw.

4. A graft fixation device according to claim 2 wherein the two guide ribs are disposed symmetrically about the graft separator.

5. A graft fixation device according to claim 3 wherein the opening in the proximal end of the graft separator has a diameter smaller than the diameter of the cavity.

6. A graft fixation device comprising:
a graft separator comprising a distal end having an opening, a proximal end having an opening, a cavity disposed between the distal end and the proximal end, and at least one guide rib disposed radially outboard of said cavity and extending longitudinally between the distal end and the proximal end, wherein the opening in the distal end of the graft separator has a diameter smaller than the diameter of the cavity, and further wherein the opening in the proximal end of the graft separator has a diameter smaller than the diameter of the cavity; and
an interference screw rotatably mountable within the cavity of the graft separator, the interference screw comprising a distal end, a proximal end, and a screw thread disposed intermediate thereof, the screw thread disposed radially outboard of the cavity of the graft separator and radially inboard of the at least one guide rib of the graft separator.

7. A graft fixation device according to claim 6 wherein the distal end of the at least one guide rib comprises a protrusion extending longitudinally from the distal end of the graft separator.

8. A graft fixation device according to claim 7 wherein the graft separator comprises two guide ribs and two protrusions, and further wherein the two protrusions extend longitudinally from the distal end of the graft separator.

9. A graft fixation device according to claim 6 wherein the opening in the distal end of the graft separator is configured to receive the distal end of the interference screw.

10. A graft fixation device according to claim 6 wherein the opening in the proximal end of the graft separator is configured to receive the proximal end of the interference screw.

11. A graft fixation device according to claim 8 wherein the two guide ribs are disposed symmetrically about the graft separator.

* * * * *